US009492195B2

United States Patent
Piskun et al.

(10) Patent No.: US 9,492,195 B2
(45) Date of Patent: Nov. 15, 2016

(54) SURGICAL PORT ASSEMBLY

(71) Applicant: Covidien LP, Mansfield, MA (US)

(72) Inventors: Gregory Piskun, Morganville, NJ (US); Oleg Shikhman, Trumbull, CT (US); Christopher Battles, Seymour, CT (US); Patrick N. Gutelius, Monroe, CT (US); Mark J. DeBisschop, Harwinton, CT (US); Jeffrey H. MacDonald, Bantam, CT (US); Frank Rende, Wesport, CT (US); Michael Abrams, New York, NY (US); Anatoly Konik, Haifa (IL); Dan Rottenberg, Haifa (IL)

(73) Assignee: Covidien LP, Mansfield, MA (US)

( * ) Notice: Subject to any disclaimer, the term of this patent is extended or adjusted under 35 U.S.C. 154(b) by 86 days.

(21) Appl. No.: 14/599,611

(22) Filed: Jan. 19, 2015

(65) Prior Publication Data

US 2015/0148613 A1 May 28, 2015

Related U.S. Application Data

(60) Division of application No. 12/550,595, filed on Aug. 31, 2009, now Pat. No. 8,961,407, which is a continuation-in-part of application No. 12/079,599, filed on Mar. 27, 2008, now Pat. No. 8,888,695, said (Continued)

(51) Int. Cl.
  *A61B 1/31* (2006.01)
  *A61B 17/34* (2006.01)
  *A61B 17/02* (2006.01)

(52) U.S. Cl.
  CPC ....... *A61B 17/3423* (2013.01); *A61B 17/0218* (2013.01); *A61B 17/3421* (2013.01);
  (Continued)

(58) Field of Classification Search
  CPC ...... A61B 1/31; A61B 1/313; A61B 1/3132; A61B 1/3135; A61B 1/317; A61B 17/02; A61B 17/0206; A61B 2017/0212; A61B 17/0218; A61B 2017/0225; A61B 17/025; A61B 2017/0256; A61B 2017/0262; A61B 17/0281; A61B 17/0293; A61B 2017/0287; A61B 17/34; A61B 17/3423; A61B 17/3431; A61B 17/3439; A61B 17/3462; A61B 2017/3425; A61B 2017/3427; A61B 2017/3433; A61B 2017/3445; A61B 2017/3466; A61B 2017/348; A61B 2017/3484; A61B 2017/349; A61B 1/32; A61B 2017/3419; A61B 2017/3449; A61B 17/3421; A61B 17/3498
  See application file for complete search history.

(56) References Cited

U.S. PATENT DOCUMENTS 2,669,991 A 2/1954 Curutchet
3,299,883 A 1/1967 Rubens
(Continued)

FOREIGN PATENT DOCUMENTS

EP 0567146 A2 10/1993
EP 0592244 A2 4/1994
(Continued)

OTHER PUBLICATIONS

International Search Report for PCT/US05/24636 dated Jun. 20, 2006 (2 pages).

(Continued)

*Primary Examiner* — Lynnsy Summitt

(57) ABSTRACT

A surgical port comprising a body and first and second cannula extending from the body and movable with respect to the body via an instrument inserted through the respective cannula. The cannulas can extend distally from the body and can include one or more seals. A port assembly and first and second instruments manipulatable in a crossed configuration are also disclosed.

18 Claims, 41 Drawing Sheets

Related U.S. Application Data application No. 12/550,595 is a continuation-in-part of application No. 10/895,546, filed on Jul. 21, 2004, now Pat. No. 7,753,901.

(60) Provisional application No. 60/920,935, filed on Mar. 30, 2007, provisional application No. 61/191,734, filed on Sep. 11, 2008.

(52) U.S. Cl.
CPC ...... *A61B17/3462* (2013.01); *A61B 2017/349* (2013.01); *A61B 2017/3441* (2013.01); *A61B 2017/3447* (2013.01); *A61B 2017/3466* (2013.01)

(56) References Cited

U.S. PATENT DOCUMENTS

| | | |
|---|---|---|
| 3,583,710 A | 6/1971 | Burelle |
| 4,016,884 A | 4/1977 | Kwan-Gett |
| 4,112,932 A | 9/1978 | Chiulli |
| 4,309,994 A | 1/1982 | Grunwald |
| 4,538,594 A | 9/1985 | Boebel et al. |
| 4,608,965 A | 9/1986 | Anspach, Jr. et al. |
| 4,644,951 A | 2/1987 | Bays |
| 4,863,430 A | 9/1989 | Klyce et al. |
| 4,863,438 A | 9/1989 | Gauderer et al. |
| 5,026,366 A | 6/1991 | Leckrone |
| 5,159,921 A | 11/1992 | Hoover |
| 5,183,471 A | 2/1993 | Wilk |
| 5,241,968 A | 9/1993 | Slater |
| 5,242,409 A | 9/1993 | Buelna |
| 5,258,006 A | 11/1993 | Rydell et al. |
| 5,269,772 A | 12/1993 | Wilk |
| 5,312,391 A | 5/1994 | Wilk |
| 5,312,417 A * | 5/1994 | Wilk ............................ 606/114 |
| 5,330,486 A | 7/1994 | Wilk |
| 5,334,143 A | 8/1994 | Carroll |
| 5,366,478 A | 11/1994 | Brinkerhoff et al. |
| 5,370,647 A * | 12/1994 | Graber et al. ................ 606/127 |
| 5,375,588 A | 12/1994 | Yoon |
| 5,383,852 A | 1/1995 | Stevens-Wright |
| 5,391,156 A | 2/1995 | Hildwein et al. |
| 5,395,327 A | 3/1995 | Lundquist et al. |
| 5,395,367 A | 3/1995 | Wilk |
| 5,441,483 A | 8/1995 | Avitall |
| 5,467,763 A | 11/1995 | McMahon et al. |
| 5,480,410 A | 1/1996 | Cuschieri et al. |
| 5,490,843 A | 2/1996 | Hildwein et al. |
| 5,509,893 A | 4/1996 | Pracas |
| 5,522,791 A | 6/1996 | Leyva |
| 5,540,648 A | 7/1996 | Yoon |
| 5,545,179 A | 8/1996 | Williamson, IV |
| 5,549,563 A | 8/1996 | Kronner |
| 5,549,637 A | 8/1996 | Crainich |
| 5,569,205 A | 10/1996 | Hart et al. |
| 5,571,115 A | 11/1996 | Nicholas |
| 5,571,137 A | 11/1996 | Marlow et al. |
| 5,575,799 A | 11/1996 | Bolanos et al. |
| 5,578,048 A | 11/1996 | Pasqualucci et al. |
| 5,603,723 A | 2/1997 | Aranyi et al. |
| 5,634,911 A | 6/1997 | Hermann et al. |
| 5,634,937 A * | 6/1997 | Mollenauer et al. ......... 606/213 |
| 5,651,771 A | 7/1997 | Tangherlini et al. |
| 5,653,705 A * | 8/1997 | de la Torre ........ A61B 17/3423 606/1 |
| 5,662,662 A | 9/1997 | Bishop et al. |
| 5,672,168 A | 9/1997 | de la Torre et al. |
| 5,683,378 A | 11/1997 | Christy |
| 5,707,359 A * | 1/1998 | Bufalini ............. A61B 17/3421 604/104 |
| 5,725,536 A | 3/1998 | Oberlin et al. |
| 5,735,791 A | 4/1998 | Alexander, Jr. et al. |
| 5,782,859 A | 7/1998 | Nicholas et al. |
| 5,795,289 A * | 8/1998 | Wyttenbach ............ A61B 1/32 600/207 |
| 5,803,921 A | 9/1998 | Bonadio |
| 5,830,191 A | 11/1998 | Hildwein et al. |
| 5,836,871 A | 11/1998 | Wallace et al. |
| 5,857,461 A | 1/1999 | Levitsky et al. |
| 5,860,995 A | 1/1999 | Berkelaar |
| 5,871,474 A | 2/1999 | Hermann et al. |
| 5,904,703 A | 5/1999 | Gilson |
| 5,906,577 A | 5/1999 | Beane et al. |
| 5,916,147 A | 6/1999 | Boury |
| 5,916,198 A | 6/1999 | Dillow |
| 5,931,832 A | 8/1999 | Jensen |
| 5,957,913 A | 9/1999 | de la Torre et al. |
| 5,964,781 A | 10/1999 | Mollenauer et al. |
| 5,997,515 A | 12/1999 | de la Torre et al. |
| 6,018,094 A | 1/2000 | Fox |
| 6,024,736 A | 2/2000 | de la Torre et al. |
| 6,033,378 A | 3/2000 | Lundquist et al. |
| 6,033,426 A | 3/2000 | Kaji |
| 6,042,573 A | 3/2000 | Lucey |
| 6,077,288 A | 6/2000 | Shimomura et al. |
| 6,086,603 A | 7/2000 | Termin et al. |
| 6,099,506 A | 8/2000 | Macoviak et al. |
| 6,142,936 A | 11/2000 | Beane et al. |
| 6,162,236 A * | 12/2000 | Osada ................ A61B 17/3439 604/264 |
| 6,217,555 B1 | 4/2001 | Hart et al. |
| 6,217,590 B1 | 4/2001 | Levinson |
| 6,238,373 B1 | 5/2001 | de la Torre et al. |
| 6,254,534 B1 * | 7/2001 | Butler et al. ................... 600/208 |
| 6,264,604 B1 | 7/2001 | Kieturakis et al. |
| 6,315,770 B1 | 11/2001 | de la Torre et al. |
| 6,319,246 B1 | 11/2001 | de la Torre et al. |
| 6,440,061 B1 | 8/2002 | Wenner et al. |
| 6,440,063 B1 | 8/2002 | Beane et al. |
| 6,447,489 B1 | 9/2002 | Peterson |
| 6,454,783 B1 | 9/2002 | Piskun |
| 6,458,077 B1 | 10/2002 | Boebel et al. |
| 6,464,686 B1 | 10/2002 | O'Hara et al. |
| 6,468,292 B1 | 10/2002 | Mollenauer et al. |
| 6,488,620 B1 | 12/2002 | Segermark et al. |
| 6,488,692 B1 | 12/2002 | Spence et al. |
| 6,531,270 B1 | 3/2003 | Olson et al. |
| 6,537,209 B1 | 3/2003 | Pinkhasik et al. |
| 6,551,270 B1 * | 4/2003 | Bimbo ............... A61B 17/3421 604/167.03 |
| 6,558,371 B2 | 5/2003 | Dorn |
| 6,578,577 B2 | 6/2003 | Bonadio et al. |
| 6,582,364 B2 | 6/2003 | Butler et al. |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,706,050 B1 | 3/2004 | Giannadakis |
| 6,800,084 B2 | 10/2004 | Davison et al. |
| 6,811,532 B2 | 11/2004 | Ogura et al. |
| 6,846,287 B2 | 1/2005 | Bonadio et al. |
| 6,878,110 B2 | 4/2005 | Yang et al. |
| 6,890,295 B2 | 5/2005 | Michels et al. |
| 6,899,673 B2 | 5/2005 | Ogura et al. |
| 6,916,331 B2 | 7/2005 | Mollenauer et al. |
| 6,945,932 B1 | 9/2005 | Caldwell et al. |
| 6,958,069 B2 * | 10/2005 | Shipp ............... A61B 17/00234 606/127 |
| 6,972,026 B1 | 12/2005 | Caldwell et al. |
| 7,001,397 B2 | 2/2006 | Davison et al. |
| 7,008,377 B2 | 3/2006 | Beane et al. |
| 7,052,454 B2 * | 5/2006 | Taylor ........................... 600/114 |
| 7,056,321 B2 | 6/2006 | Pagliuca et al. |
| 7,081,089 B2 | 7/2006 | Bonadio et al. |
| 7,195,590 B2 | 3/2007 | Butler et al. |
| 7,214,185 B1 | 5/2007 | Rosney et al. |
| 7,223,257 B2 | 5/2007 | Shubayev et al. |
| 7,223,278 B2 | 5/2007 | Davison et al. |
| 7,235,084 B2 | 6/2007 | Skakoon et al. |
| 7,238,154 B2 | 7/2007 | Ewers et al. |
| 7,276,075 B1 | 10/2007 | Callas et al. |
| 7,300,399 B2 * | 11/2007 | Bonadio et al. ............. 600/208 |
| 7,316,699 B2 | 1/2008 | McFarlane |
| 7,445,597 B2 * | 11/2008 | Butler et al. ................. 600/208 |
| 7,473,221 B2 * | 1/2009 | Ewers et al. ................. 600/208 |

(56) References Cited

U.S. PATENT DOCUMENTS

| | | | |
|---|---|---|---|
| 7,559,893 B2* | 7/2009 | Bonadio et al. | 600/208 |
| 7,727,146 B2* | 6/2010 | Albrecht | A61B 17/02 |
| | | | 600/201 |
| 7,837,612 B2* | 11/2010 | Gill et al. | 600/37 |
| 8,657,740 B2* | 2/2014 | Bonadio et al. | 600/201 |
| 2002/0038077 A1 | 3/2002 | de la Torre et al. | |
| 2002/0183594 A1 | 12/2002 | Beane et al. | |
| 2003/0014076 A1 | 1/2003 | Mollenauer et al. | |
| 2003/0036748 A1 | 2/2003 | Cooper et al. | |
| 2003/0114832 A1 | 6/2003 | Kohler et al. | |
| 2003/0135091 A1 | 7/2003 | Nakazawa et al. | |
| 2003/0208122 A1 | 11/2003 | Melkent et al. | |
| 2003/0216770 A1* | 11/2003 | Persidsky | A61B 17/3423 |
| | | | 606/191 |
| 2003/0236549 A1 | 12/2003 | Bonadio et al. | |
| 2004/0049099 A1 | 3/2004 | Ewers et al. | |
| 2004/0167543 A1 | 8/2004 | Mazzocchi et al. | |
| 2004/0230100 A1 | 11/2004 | Shluzas | |
| 2005/0137609 A1 | 6/2005 | Guiraudon | |
| 2005/0209608 A1* | 9/2005 | O'Heeron | 606/108 |
| 2005/0215863 A1 | 9/2005 | Ravikumar et al. | |
| 2005/0222582 A1 | 10/2005 | Wenchell | |
| 2005/0241647 A1 | 11/2005 | Nguyen et al. | |
| 2005/0273133 A1 | 12/2005 | Shluzas et al. | |
| 2005/0288558 A1 | 12/2005 | Ewers et al. | |
| 2006/0004188 A1 | 1/2006 | Leung et al. | |
| 2006/0020241 A1 | 1/2006 | Piskun et al. | |
| 2006/0041232 A1 | 2/2006 | Stearns et al. | |
| 2006/0149306 A1 | 7/2006 | Hart et al. | |
| 2006/0241651 A1 | 10/2006 | Wilk | |
| 2006/0247498 A1 | 11/2006 | Bonadio et al. | |
| 2007/0049966 A1* | 3/2007 | Bonadio | A61B 17/00234 |
| | | | 606/206 |
| 2007/0060939 A1* | 3/2007 | Lancial | A61B 1/00154 |
| | | | 606/191 |
| 2007/0203398 A1 | 8/2007 | Bonadio et al. | |
| 2007/0208312 A1 | 9/2007 | Norton et al. | |
| 2007/0270654 A1 | 11/2007 | Pignato et al. | |
| 2007/0276430 A1 | 11/2007 | Lee et al. | |
| 2008/0027476 A1 | 1/2008 | Piskun | |
| 2008/0058590 A1* | 3/2008 | Saadat | A61B 1/00085 |
| | | | 600/109 |
| 2008/0103366 A1 | 5/2008 | Banchieri et al. | |
| 2008/0161826 A1* | 7/2008 | Guiraudon | 606/108 |
| 2008/0183044 A1* | 7/2008 | Colleran | A61B 17/02 |
| | | | 600/208 |
| 2008/0200767 A1 | 8/2008 | Ewers et al. | |
| 2008/0255519 A1 | 10/2008 | Piskun et al. | |
| 2009/0012477 A1 | 1/2009 | Norton et al. | |
| 2010/0249523 A1* | 9/2010 | Spiegal et al. | 600/206 |

FOREIGN PATENT DOCUMENTS

| | | |
|---|---|---|
| EP | 1312318 A1 | 5/2003 |
| EP | 1637086 A1 | 3/2006 |
| EP | 1870043 A2 | 12/2007 |
| EP | 2044889 A1 | 4/2009 |
| WO | 93/14801 A1 | 8/1993 |
| WO | 94/04067 A1 | 3/1994 |
| WO | 97/42889 A1 | 11/1997 |
| WO | 9901638 A1 | 1/1999 |
| WO | 02/07611 A2 | 1/2002 |
| WO | 2006/100658 A2 | 9/2006 |
| WO | 2006/113216 A2 | 10/2006 |
| WO | 2008/015566 A2 | 2/2008 |
| WO | 2008/121294 A1 | 10/2008 |

OTHER PUBLICATIONS

International Search Report for PCT/US08/03991 dated Jul. 30,m 2008 (1 page).
European Search Report for EP 09252160 dated Mar. 17, 2010 (2 pages).
European Search Report for EP 09252168 dated Mar. 19, 2010 (3 pages).

* cited by examiner

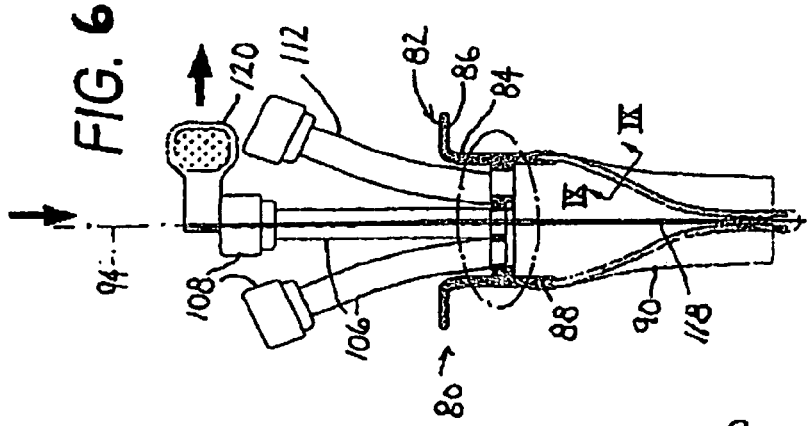
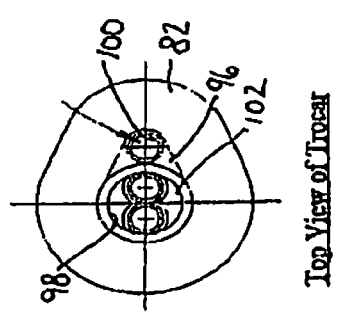
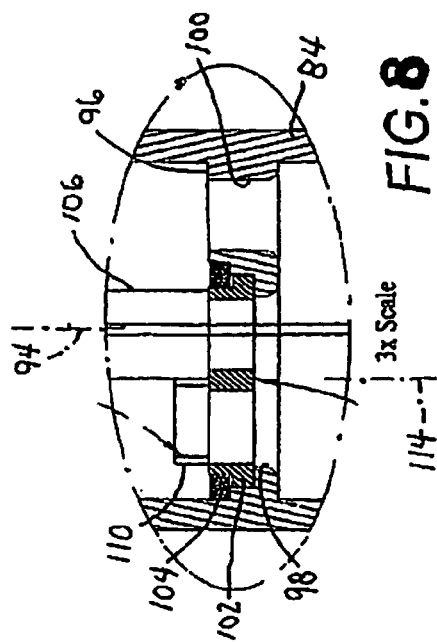

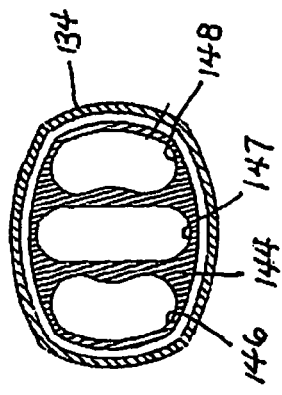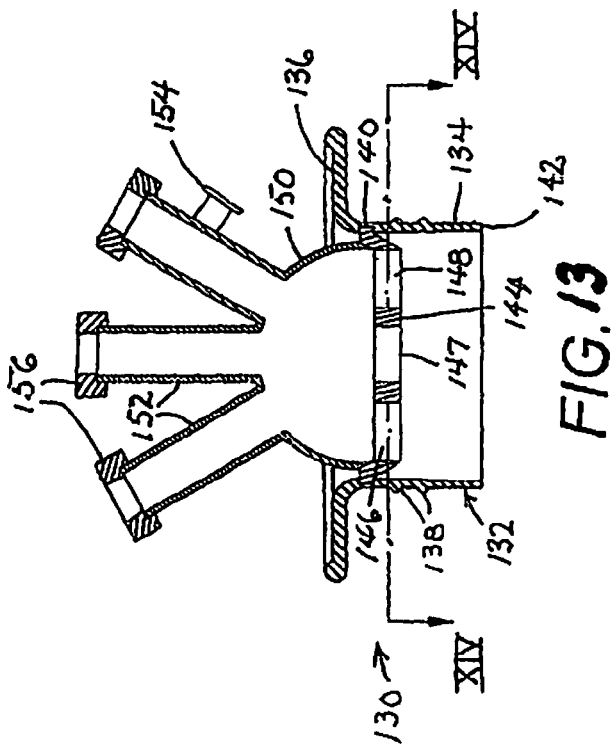

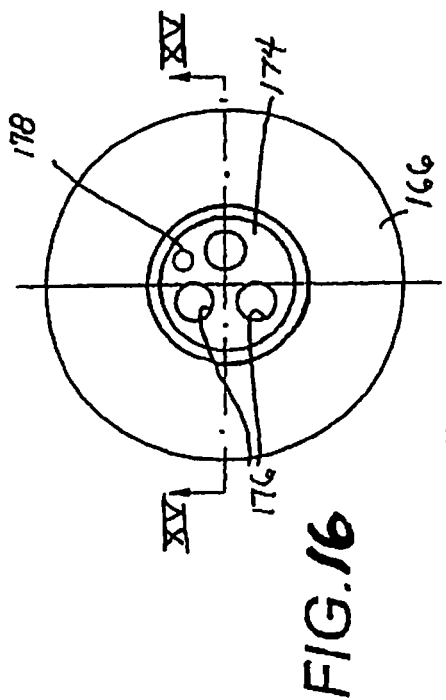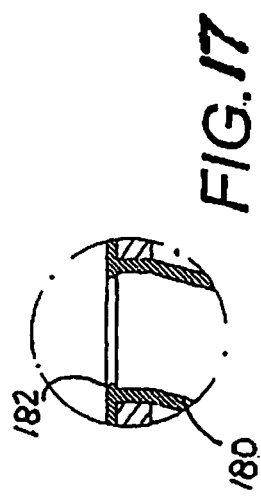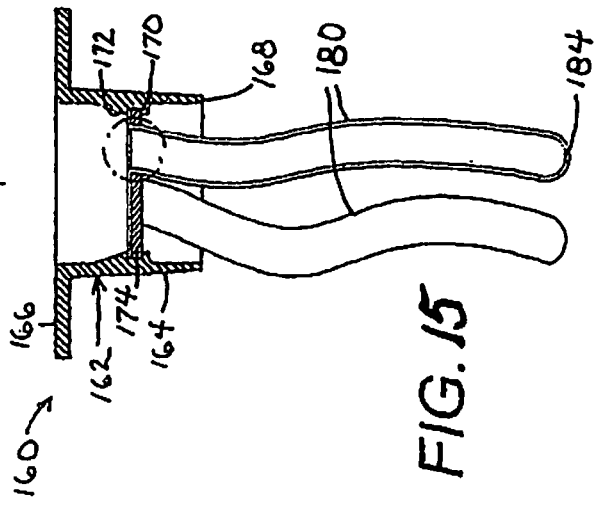

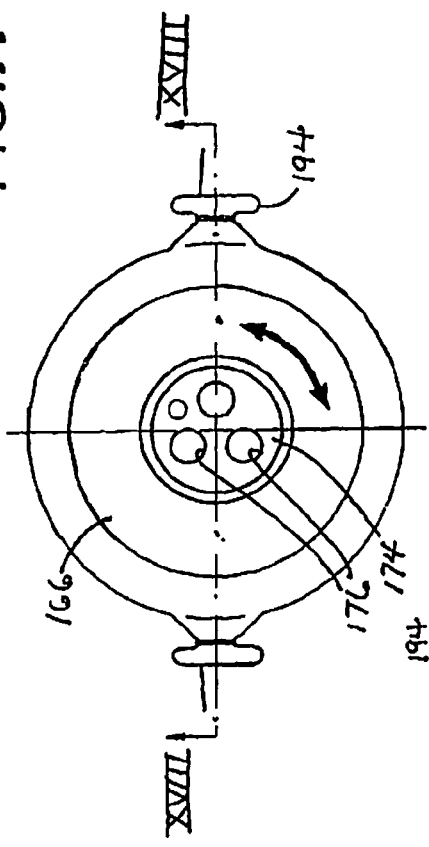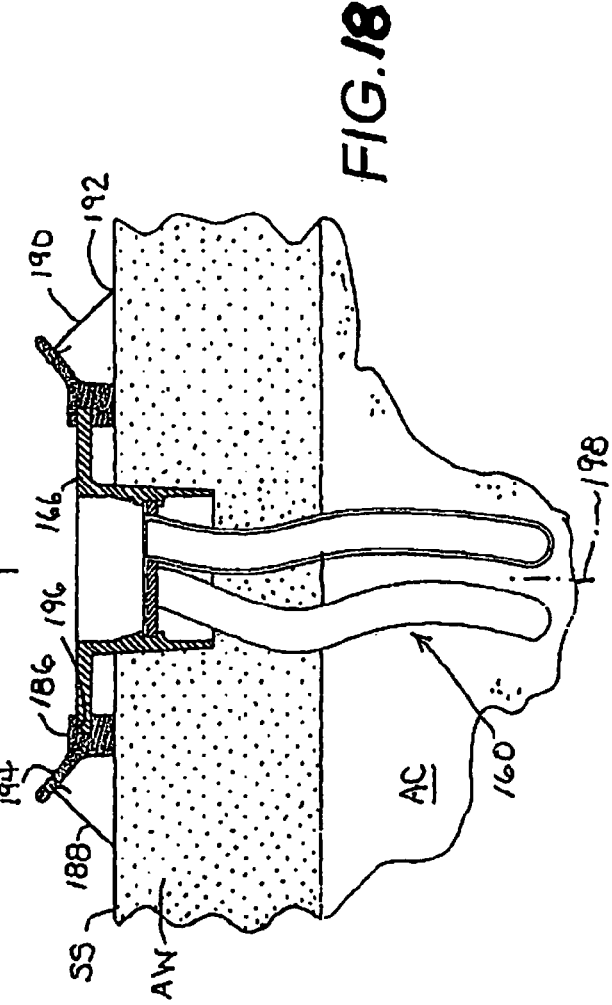

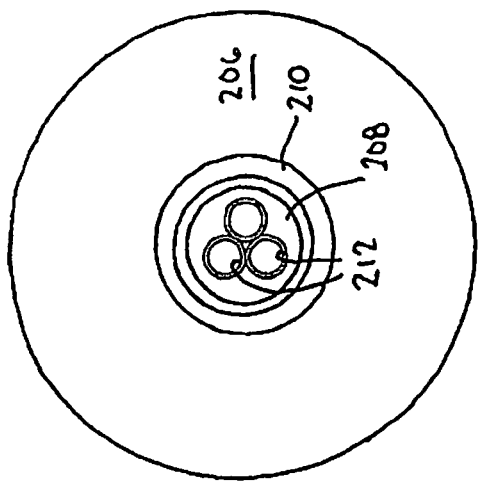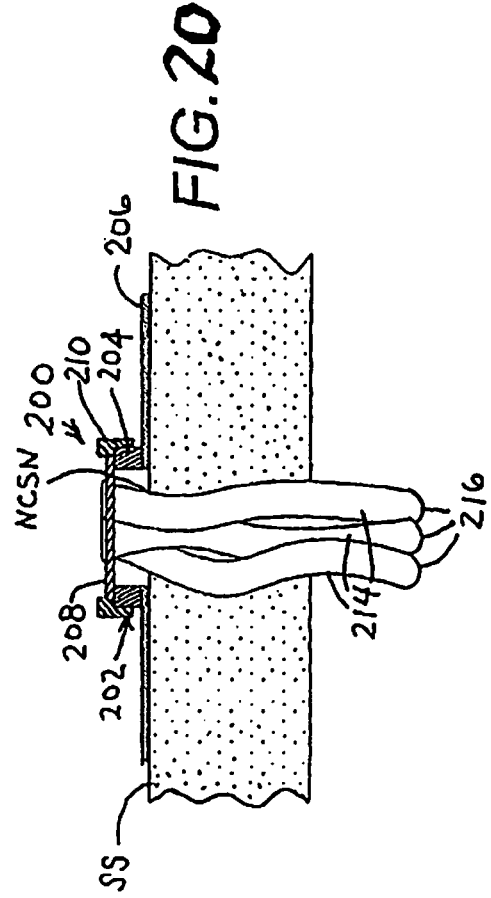

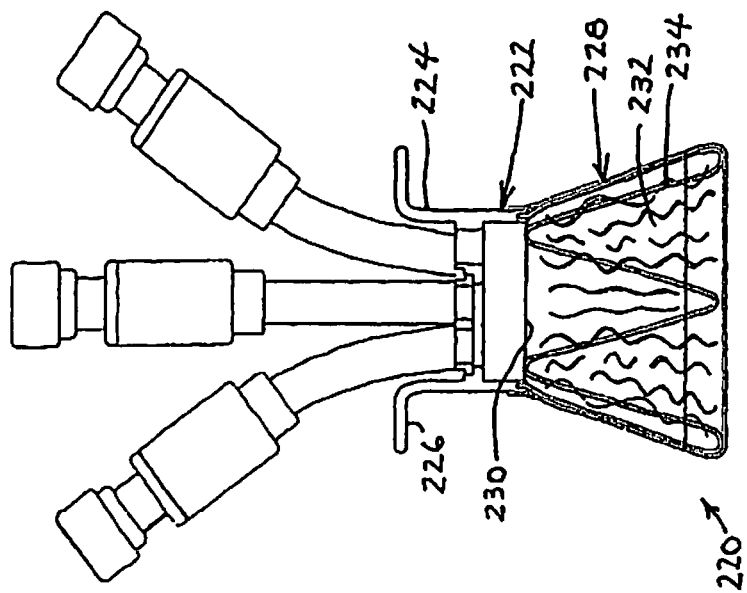
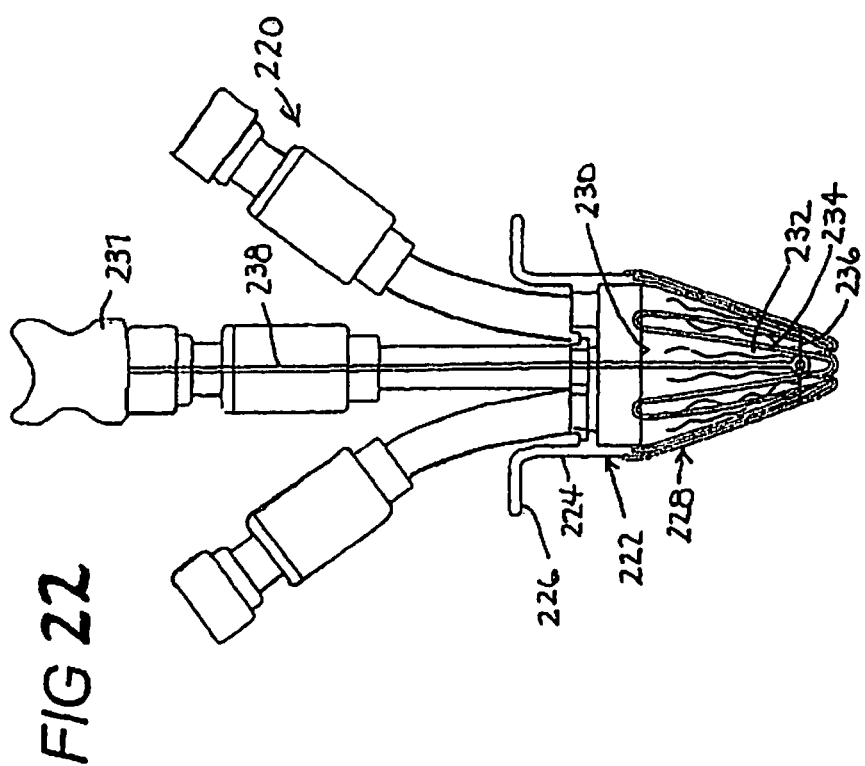

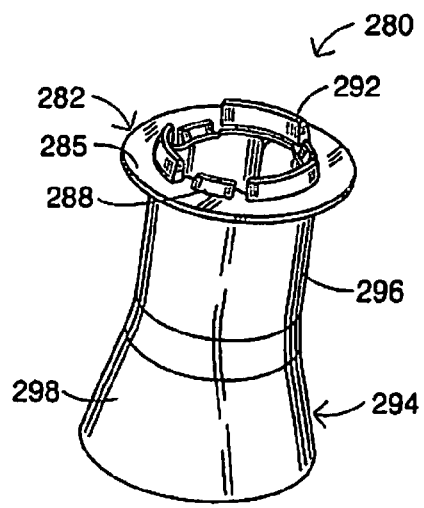
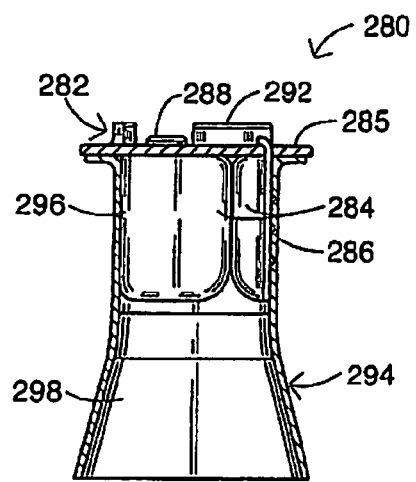
FIG. 33
FIG. 34
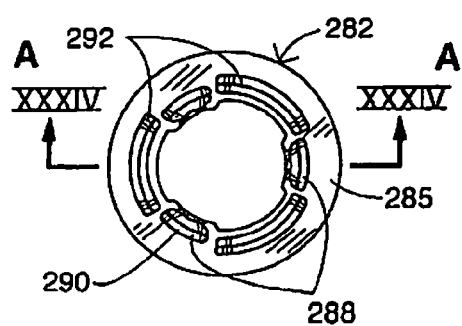
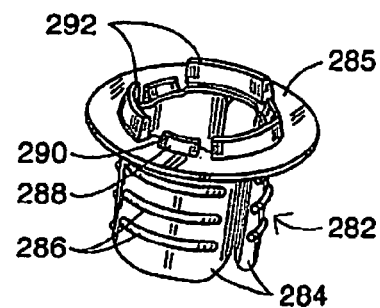
FIG. 35
FIG. 36

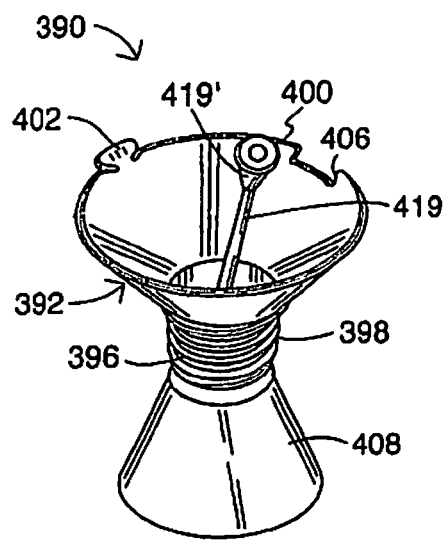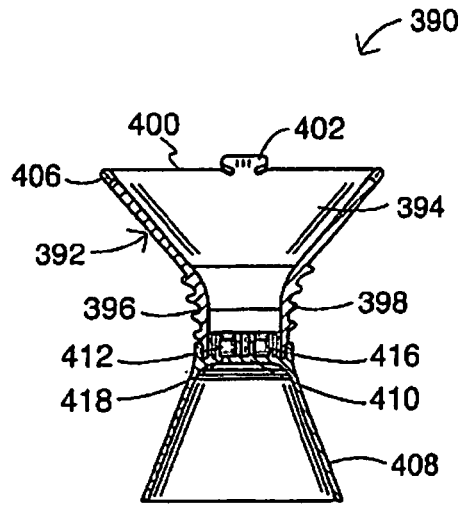
FIG. 48　　　　　　FIG. 49
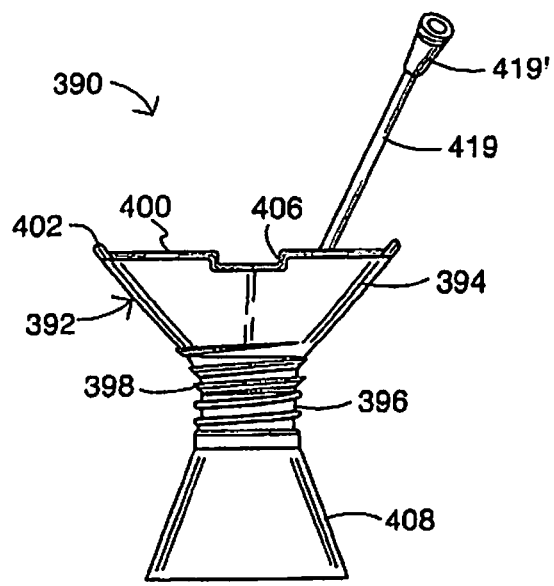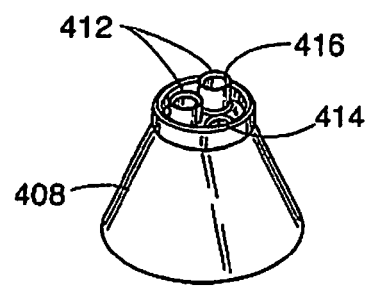
FIG. 50　　　　　　FIG. 51

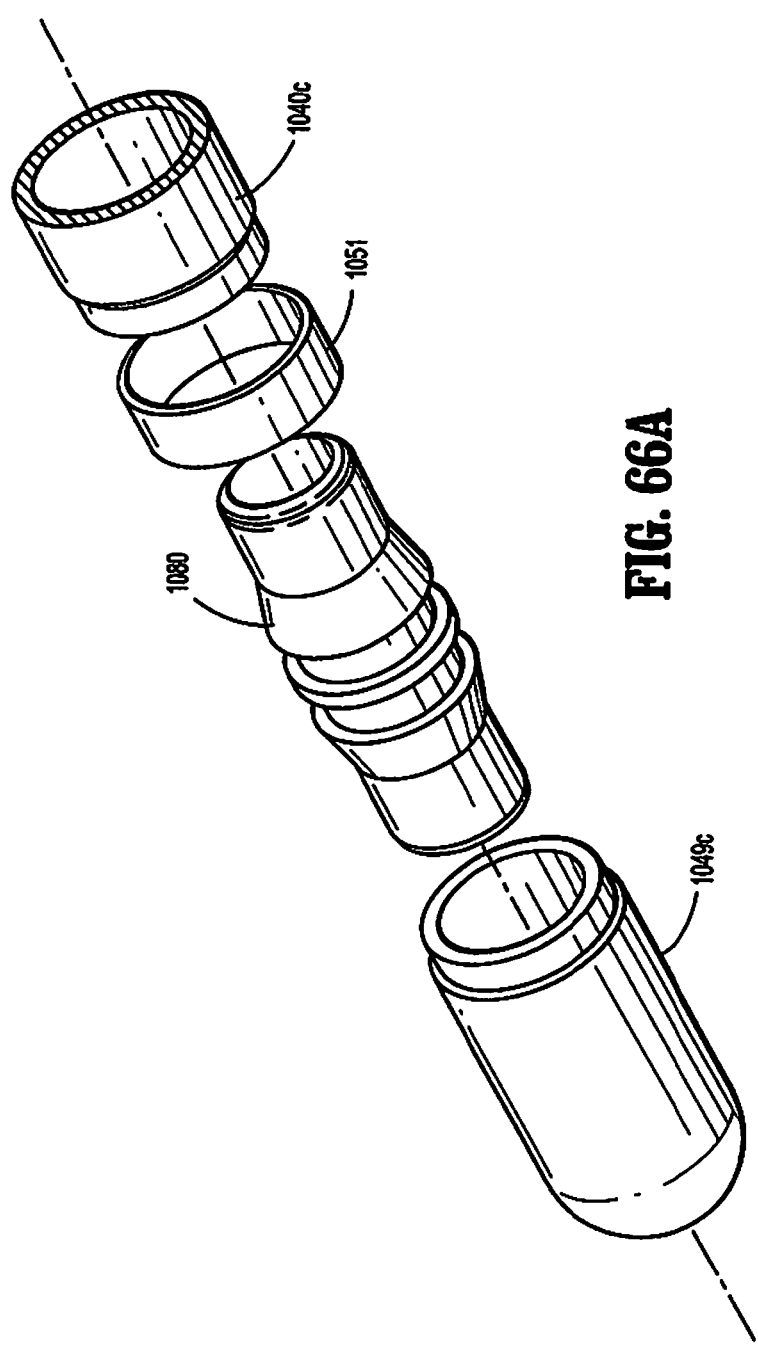

SURGICAL PORT ASSEMBLY

CROSS-REFERENCE TO RELATED APPLICATIONS

The present application is a divisional of U.S. patent application Ser. No. 12/550,595, filed on Aug. 31, 2009, published as U.S. Patent Application Publication US 2010/0113886 A1, now U.S. Pat. No. 8,961,407, which is a continuation-in-part of application Ser. No. 12/079,599 filed Mar. 27, 2008, now U.S. Pat. No. 8,888,695, which claims the benefit of U.S. Provisional Patent Application No. 60/920,935 filed Mar. 30, 2007 and is a continuation-in-part of application Ser. No. 10/895,546, filed Jul. 21, 2004, now U.S. Pat. No. 7,753,901. This application also claims the benefit of U.S. Provisional Patent Application No. 61/191,734 filed Sep. 11, 2008. The entire contents of each of these applications is incorporated herein by reference.

FIELD OF THE INVENTION

The present invention relates to surgical port assemblies. The port assemblies of the present invention are particularly useful in minimally invasive surgical procedures such as laparoscopic operations entirely through the umbilicus.

BACKGROUND OF THE INVENTION

Abdominal laparoscopic surgery gained popularity in the late 1980's, when benefits of laparoscopic removal of the gallbladder over traditional (open) operation became evident. Reduced postoperative recovery time, markedly decreased post-operative pain and wound infection, and improved cosmetic outcome are well established benefits of laparoscopic surgery, derived mainly from the ability of laparoscopic surgeons to perform an operation utilizing smaller incisions of the body cavity wall.

Laparoscopic procedures generally involve insufflation of the abdominal cavity with $CO_2$ gas to a pressure of around 15 mm Hg. The abdominal wall is pierced and a 5-10 mm in diameter straight tubular cannula or trocar sleeve is then inserted into the abdominal cavity. A laparoscope connected to an operating room monitor is used to visualize the operative field, and is placed through (one of) the trocar sleeve(s). Laparoscopic instruments (e.g., graspers, dissectors, scissors, retractors, etc.) are placed through two or more additional trocar sleeves for the manipulations by the surgeon and surgical assistant(s).

"Mini-laparoscopy has been introduced utilizing 2-3 mm diameter straight trocar sleeves and laparoscopic instruments. When successful, mini-laparoscopy allows further reduction of abdominal wall trauma and improved cosmesis. However, instruments used for mini-laparoscopic procedures are generally more expensive and fragile. Additionally, because of their performance limitations, due to their smaller diameter (e.g., weak suction-irrigation system, poor durability, decreased video quality), mini-laparoscopic instruments can generally be used only on selected patients with favorable anatomy (e.g., thin cavity wall, few adhesions, minimal inflammation, etc.). These patients represent a small percentage of patients requiring laparoscopic procedure. In addition, smaller, 2-3 mm, incisions may still cause undesirable cosmetic outcomes and wound complications (e.g., bleeding, infection, pain, keloid formation, etc.).

Since the benefits of smaller and fewer body cavity incisions are proven, it would be attractive to perform an operation utilizing only a single incision such as in the navel. An umbilicus is the thinnest and least vascularized, and a well-hidden, area of the abdominal wall. The umbilicus is generally a preferred choice of abdominal cavity entry in laparoscopic procedures. An umbilical incision can be easily enlarged (in order to eviscerate a larger specimen) without significantly compromising cosmesis and without increasing the chances of wound complications. However, the placement of two or more standard (straight) cannulas and laparoscopic instruments in the umbilicus, next to each other, creates a so-called "chopstick" effect, which describes interference between the surgeon's hands, between the surgeon's hands and the instruments, and between the instruments. This interference greatly reduces the surgeon's ability to perform a surgical procedure.

Thus, it would be advantageous to provide instruments and trocar systems which allow laparoscopic procedures to be performed entirely through the umbilicus or other single incision while at the same time reducing or eliminating the "chopstick effect." A laparoscopic procedure performed entirely through a single opening such as the umbilicus—has the benefits of accomplishing the necessary diagnostic and therapeutic tasks while further minimizing abdominal wall trauma, improving cosmesis and reducing patient recovery time.

In providing a system for such minimally invasive procedure, it would be advantageous to maximize the range of motion of the instruments extending through the port system. The greater the range of motion, the easier it is for the surgeon to perform the procedure, and, in fact, increased range of motion could also advantageously increase the types of surgical procedures able to be performed.

SUMMARY OF THE INVENTION

The present invention facilitates the performance of minimally invasive surgical procedures wherein several instruments are inserted into a patient through respective cannulas all extending through the same opening in the patient, for instance, through the umbilicus. The advantages of such an operation include, as noted above, minimizing trauma to the patient and accelerating patient recovery.

A first embodiment of a surgical port assembly in accordance with the present invention comprises a body attachable to a patient at an incision in a skin surface of the patient to facilitate deployment of instruments in the patient via the incision. The body has a main axis oriented substantially transversely to the patient's skin surface upon disposition of the body in the incision. The port assembly further comprises a main first plate, a second plate, at least one first tubular member and a second tubular member. The first plate has a first opening and a second opening and is mounted to the body substantially transversely to the axis. The second plate is rotatably disposed in the first opening for turning about an auxiliary axis preferably substantially parallel to the main axis. The first tubular member is attached to the second plate and extends in at least one direction away from the second plate. The second tubular member is attached to the first plate at the second opening and extends in at least one direction away from the first plate.

The body of the port assembly has an outer side facing away from the patient and an inner side facing inwardly of or towards the patient's skin surface during a surgical procedure. Pursuant to one alternative design of the port assembly, the first tubular member extends only upwardly or outwardly away from the second plate, on the outer side of the body. Preferably, the first tubular member is one of a plurality of first tubular members all attached to the second plate and extending only upwardly or outwardly away from the second plate, on the outer side of the body. According to a specific feature of this design, at least one of the first tubular members is flexible at least at a point of attachment to the second plate, enabling a pivoting (about a transverse axis) and/or a swiveling (about a longitudinal axis) at the second plate of a surgical instrument inserted through the at least one of the first tubular members. The first tubular members are each provided with at least one seal for maintaining pneumoperitoneum when a surgical instrument shaft longitudinally traverses such first tubular member and at least one seal for maintaining pneumoperitoneum in the absence of a surgical instrument shaft longitudinally traversing such first tubular member.

Pursuant to another alternative design of the port assembly, the first tubular member extends only downwardly or inwardly away from the second plate, on the inner side of the body. Preferably in this design, the first tubular member is one of a plurality of first tubular members all attached to the second plate and extending only downwardly or inwardly away from the second plate, on the inner side of the body. According to a specific feature of this alternative design, at least one of the first tubular members is flexible at least at a point of attachment to the second plate, enabling a pivoting (about a transverse axis) and/or a swiveling (about a longitudinal axis) at the second plate of a surgical instrument inserted through the at least one of the first tubular members. Again, the first tubular members are each provided with at least one seal for maintaining pneumoperitoneum when a surgical instrument shaft longitudinally traverses such first tubular member and at least one seal for maintaining pneumoperitoneum in the absence of a surgical instrument shaft longitudinally traversing such first tubular member.

Pursuant to additional features of the present invention, the second plate is dome-shaped and the second plate is removably attached to the first plate.

A second embodiment of a surgical port assembly in accordance with the present invention comprises a body attachable to a patient at an incision in a skin surface of the patient to facilitate deployment of instruments in the patient via the incision, the body having an outer side facing away from the patient and an inner side facing inwardly of or towards the patient's skin surface during a surgical procedure. At least one tubular member depends downwardly or inwardly from the body so that the tubular member is disposed only on the inner side of the body.

The downwardly depending tubular member is preferably one of a plurality of tubular members all depending downwardly or inwardly from the body so that the tubular members are disposed only on the inner side of the body. Each of the tubular members is preferably provided with at least one seal for maintaining pneumoperitoneum when a surgical instrument shaft longitudinally traverses such tubular member and additionally provided with at least one seal for maintaining pneumoperitoneum in the absence of a surgical instrument shaft longitudinally traversing such tubular member.

The downwardly depending tubular members may be made fully or partially of elastomeric material. Preferably, the tubular members are tiltable at least at an upper end In accordance with a further feature of the present invention, the downwardly depending tubular members are each provided along an inner surface with a rigid sleeve so arranged that the tubular members are each pivotable about a point of attachment to the body.

The body of the port assembly may have a funnel shape. In that case, the tubular members are attached to the funnel shape at an apical end thereof. The funnel shape may be a truncated cone that may have a circular, elliptical, oval or other cross-section.

In this second embodiment of the present invention, the outer side of the port assembly's body is free of upwardly or outwardly extending tubular cannula members and comprises a rim portion and a plate surrounded by the rim portion, the tubular members being connected to the plate and extending only on an inner side of the plate. The rim portion may sit on the skin surface of the patient and be attached thereto via adhesive. Alternatively, the rim portion may insert at least partially into the incision in the skin surface. In either case, the rim portion may have a circular or annular configuration.

The one or more downwardly depending tubular members may be detachably attached to the port assembly's body. In that case, the tubular member or members are fixed to a coupling member that in turn is detachably attached to the body at an aperture in the body. The port assembly may further comprise a plug to temporarily seal the aperture upon removal of the coupling member from the aperture.

Pursuant to another feature of the invention, the singular downwardly depending tubular member or one of the multiple downwardly depending tubular members carries a camera at a free end. The camera-carrying tubular member may be provided with directional cables that are actuatable from the outer or upper side of the port assembly for changing an orientation of the free end of the respective tubular member and the camera.

A third embodiment of a surgical port assembly comprise, in accordance with the present invention, a body attachable to a patient at an incision in a skin surface of the patient to facilitate deployment of instruments in the patient via the incision, the body having an outer side facing away from the patient and an inner side facing inwardly of or towards the patient's skin surface during a surgical procedure. A funnel-shaped extension is provided on the outer side of the body. The body together with the funnel-shaped extension may be made of a rigid metallic or polymeric material or a tough elastomeric material with some resilience and flexibility.

An obturator for deployment of a surgical port assembly (such as the second embodiment described above) through a skin surface comprises a body member, locking formations on the body member releasably engageable with cooperating locking formations on the port assembly, at least two finger contact surfaces on the body member, the finger contact surfaces facing in substantially opposed directions, for enabling manual application of a torque to the body member, and at least one elongate rigid member extending away from the body member on a side thereof opposite the finger contact surfaces, for penetrating through a skin surface.

The rigid member may be one of a plurality of parallel elongate rigid members extending away from the body member on a side thereof opposite the finger contact surfaces, for penetrating through a skin surface. The multiple rigid members of the obturator insert into respective downwardly depending tubular members of the second port assembly embodiment described above. The rigid members of the obturator thus serve to stiffen and hold the tubular members when the port assembly is being deployed at the onset of a minimally invasive surgical procedure, for example, a laparoscopic or thoracoscopic operation.

Accordingly, it is contemplated that the obturator is a component of a surgical access assembly or kit that further comprises a surgical port assembly including (a) a port assembly body attachable to a patient at an incision in a skin surface of the patient to facilitate deployment of instruments in the patient via the incision, the body having an outer side facing away from the patient and an inner side facing inwardly of or towards the patient's skin surface during a surgical procedure, and (b) a plurality of elastomeric tubular members all depending downwardly or inwardly from the port assembly body so that the tubular members are disposed only on the inner side of the body, the tubular members receiving respective ones of the elongate rigid members.

The locking formations may include projections on the body member or the obturator and recesses on the port assembly. The body member may take the form of a disk, which is provided with at least one cutout for enabling passage of an insufflation tube.

A surgical port assembly in accordance with one embodiment of the present invention comprises a body member and a skirt member. The body member is attachable to a patient at an incision in a skin surface of the patient to facilitate deployment of instruments in the patient via the incision, the body having an outer side facing away from the patient and an inner side facing inwardly of or towards the patient's skin surface during a surgical procedure. The skirt member is at least partially flexible and is attached to the body on the inner side thereof.

This embodiment of a surgical port assembly in accordance with the present invention may further comprise a trocar member insertable through the body and traversing the body during a deployment procedure. The skirt member has a collapsed or folded-in insertion configuration, wherein the skirt member is releasably attached to the trocar member during the deployment procedure. A portion of the skirt member may be removably inserted into a slot in the trocar member, to hold the skirt member in the folded-in configuration.

The skirt member may have a tapered expanded configuration wherein a free end of the skirt member, opposite the body member, has a larger transverse dimension that an end of the skirt attached to the body member.

The skirt member may include a flexible web member and a resilient support wire connected to the web member for expanding the web member from a folded-in insertion configuration to an expanded use configuration.

The skirt member may include flexible strip areas interleaved or alternating with more rigid areas.

Pursuant to additional specific features of the present invention, the body member may include a cylindrical portion, a dome on an upper or proximal side of the cylindrical portion, and a circumferential or annular disk-shaped flange, the dome being formed with a plurality of openings for passage of laparoscopic or thoracoscopic instrument shafts and a laparoscope or endoscope. The skirt member includes a cylindrical section engaging the cylindrical portion of the body and further includes a tapered or conical portion.

A related surgical port element in accordance with the present invention comprises a skirt made at least partially of flexible material and means for attaching the skirt to a cannula or instrument holder in turn removably attachable to a patient at an opening in a skin surface. The skirt has a folded-in insertion configuration and an expanded use configuration.

A surgical port component comprises, in accordance with the present invention, a body including a cylindrical portion formed by a plurality of cylindrical sections or flaps. The body further includes a ring-shaped base member, the cylindrical sections or flaps being swingably coupled to the base member. The cylindrical sections or flaps are made of at least a substantially rigid material, and the base member is provided with at least one upwardly or proximally extending arcuate flange section receivable into a distal or lower end of a cylindrical body of a flexible-cannula port member. An at least partially flexible skirt may be coupled to the body of the port component, for instance, by a cylindrical proximal sleeve section of the skirt fitting over the cylindrical sections or flaps.

Another surgical port assembly in accordance with the present invention comprises a body member and a flexible scope arm. The body member is attachable to a patient at an incision in a skin surface of the patient to facilitate deployment of instruments in the patient via the incision, the body member having an outer side facing away from the patient and an inner side facing inwardly of or towards the patient's skin surface during a surgical procedure. The flexible scope arm is connected to the body member and extends from an underside of the body member. The scope arm incorporates a digital camera at a distal end, the camera being maneuverable via cables in the scope arm, the scope arm being operatively connectable at a proximal end to an endoscope functional module enabling operation of the camera.

A thoracoscopic surgical port assembly in accordance with the present invention comprises (a) a downwardly tapering, substantially flexible, upper or proximal part, and (b) an upwardly tapering, substantially flexible lower or distal part connected to the upper or proximal part. The lower or distal part is extendable in between the ribs of a patient into a pleural space. A substantially rigid ring-like structure is disposed proximate a junction between the upper or proximal part and the lower or distal part. The ring structure is locatable, during use of the port assembly, on top of a patient's ribs. A flexible membrane is provided proximate the ring structure, the membrane having a plurality of openings for passage of the instruments.

A surgical port assembly comprises, in accordance with another embodiment of the present invention, a rigid mounting ring, a body member and a cannula unit. The ring is disposable on and releasably attachable a patient's skin surface. The body member is attachable to the ring to depend downwardly therefrom through an incision in the patient's skin surface to facilitate deployment of instruments in the patient via the incision. The body member has an outer side facing away from the patient and an inner side facing inwardly of or towards the patient's skin surface during a surgical procedure. The body member is rotatably attachable to the ring for turning about an axis oriented perpendicularly to a plane defined by the ring. The cannula unit is attachable to the body member and carries a plurality of cannulas.

Yet another surgical port assembly in accordance with the present invention comprises a body attachable to a patient at an incision in a skin surface of the patient to facilitate deployment of instruments in the patient via the incision, the body having an outer side facing away from the patient and an inner side facing inwardly of or towards the patient's skin surface during a surgical procedure. The port assembly also comprises a cannula unit including an elastomeric dome-shaped base and a plurality of upwardly extending tubular members or cannulas each provided with a cap housing a plurality of seals.

The present invention provides in one aspect a surgical port comprising a body composed at least in part of a first material and a membrane composed at least in part of a second different material and supported by the body, wherein at least portion of the membrane is flexible. First and second cannulas extend from the membrane and are movable with respect to the body via movement of an instrument inserted therethrough.

In one embodiment, the membrane is composed of stretchable material, enabling pivoting and twisting of the cannnulas to alter the position of instruments inserted therethrough. Preferably, the body has a transverse dimension at a proximal portion greater than a transverse dimension at a distal portion. The body can include a tissue engaging portion having an irregular outer surface portion to enhance gripping of the tissue adjacent the opening for retention of the body.

The body can be composed of a rigid material. In some embodiments, the body can include an expandable flexible wire embedded in the wall.

In some embodiments, the cannulas have a proximal opening adjacent the membrane and a distal opening extending distally of the body. A stiffening member can be positioned in one or more of the cannulas. One or more seals can be provided in the cannulas.

The present invention also provides in another aspect a surgical port comprising a body and a cannula support. The cannula support extends substantially transversely to the body and a plurality of cannulas are connected to the cannula support by a pivotable joint to enable pivoting of the cannulas with respect to the support.

In some embodiments, the support comprises a rigid plate and the joint is a ball joint. In some embodiments, a proximal end of the cannulas extends from the pivotable joint. In other embodiments, a distal end of the cannnulas extends from the pivotable joint.

The present invention also provides in another aspect a surgical port comprising a body portion, a support mounted within the body portion, and first and second cannulas extending from the support at a respective first and second juncture, wherein the first and second cannulas are flexible with respect to the support at the respective first and second juncture.

The present invention also provides in another aspect a surgical port comprising a body, first and second members movable with respect to the body, and first and second cannulas extending from the body. The first and second members are independently movable to change the orientation of the respective cannula(s).

Preferably, the first and second members are plates composed at least in part of metal wherein the first plate is positioned distally of the second plate.

In another aspect, the present inventions provides a surgical port comprising a body having a wall, first and second cannulas extending from the body and being movable with respect to the body via movement of an instrument inserted therethrough. At least portions of the body wall are deformable by pressure exerted by the instrument thereon. A support is engagable with the body to increase the rigidity of at least portions of the body.

The present invention also provides in another aspect in combination a surgical port having first and second cannulas extending therefrom and first and second instruments for performing a surgical procedure. The cannulas are mounted to the port to provide at least a pivoting range of motion such that the orientation of the cannulas is changeable. A first instrument is insertable through the first cannula and a second instrument is insertable through the second cannula. The first and second instruments each have a distal shaft portion angled with respect to a more proximal shaft portion and the instruments are insertable and manipulatable in a crossed configuration with the distal ends of the instruments pointable toward each other.

In a preferred embodiment, the port has a body and the cannulas extend distally from the body. In some embodiments, the first and second instruments each have a first and second jaw, wherein at least the first jaw is movable with respect to the second jaw and the jaws are rotatable with respect to the more proximal shaft portion by an actuator remote from the jaws.

The present invention also provides in another aspect in combination a surgical port, a first instrument, and a flexible endoscope for performing a surgical procedure. The port has first and second cannulas extending therefrom, the cannulas mounted to the port to provide at least a pivoting range of motion such that orientation of the cannulas is changeable. A first instrument is insertable through the first cannula for performing an operative step on tissue and a flexible endoscope is insertable through the second cannula for visualization of the surgical site.

The combination may further include a rigid member at least partially positioned within the second cannula to angle the cannula to thereby angle the scope. In some embodiments, the rigid member is secured to the port at an angle to maintain the angled position of the second cannula.

The present invention also provides in another aspect a method for performing a minimally invasive surgical procedure, the method comprising the steps of: positioning a port with respect to a patient, the port having first and second cannulas extending therefrom, inserting a first instrument through the first cannula; inserting a second instrument through the second cannula, wherein at least during a portion of the surgical procedure a distal tip of the second instrument points toward a distal tip of the first instrument; and moving at least the first instrument to change the orientation of the cannulas and to position the first and second instruments in a crossed configuration. The method may further comprise the step of inserting a flexible endoscope through a third cannula of the port and securing the third cannula in an angled position.

BRIEF DESCRIPTION OF THE DRAWINGS

FIG. 6 is a schematic longitudinal cross-sectional view of a modified trocar or surgical port assembly in accordance with the present invention, showing a trocar body with a perforated plate therein.

FIG. 7 is a top plan view of the trocar or surgical port assembly of FIG. 6, showing three instrument ports.

FIG. 8 is a partial schematic cross-sectional view, on a larger scale, of the modified trocar or surgical port assembly of FIGS. 6 and 7.

FIG. 9 is a partial cross-sectional view taken along line IX-IX in FIG. 6.

FIG. 13 is a schematic longitudinal cross-sectional view of another trocar or surgical port assembly in accordance with the present invention.

FIG. 14 is a cross-sectional view taken along line XIV-XIV in FIG. 13.

FIG. 15 is a schematic longitudinal cross-sectional view of a further trocar or surgical port assembly in accordance with the present invention.

FIG. 16 is a top plan view of the trocar or surgical port assembly of FIG. 15, showing three instrument ports and an insufflation port. The cross-sectional view of FIG. 15 is taken along line XV-XV in FIG. 16.

FIG. 17 is a partial cross-sectional view, on a larger scale, of a detail XVII of FIG. 15.

FIG. 18 is a schematic longitudinal cross-sectional view of the trocar or surgical port assembly of FIGS. 15-17, showing the port assembly rotatably supported via a mounting ring on a patient's abdomen.

FIG. 19 is a top plan view of the trocar or surgical port assembly and mounting ring of FIG. 16. The cross-sectional view of FIG. 18 is taken along line XVIII-XVIII in FIG. 19.

FIG. 20 is a schematic longitudinal cross-sectional view of a further trocar or surgical port assembly in accordance with the present invention, showing the port assembly deployed in an abdominal wall of a patient.

FIG. 21 is a top plan view of the trocar or surgical port assembly of FIG. 20, showing three instrument ports. The cross-sectional view of FIG. 20 is taken along line XX-XX in FIG. 21.

FIG. 22 is a schematic side elevational view, partially in cross-section, of a further trocar or surgical port assembly in accordance with the present invention, showing a skirt in a collapsed insertion configuration.

FIG. 23 is partially a side elevational view similar to FIG. 22, showing the skirt in an expanded use configuration.

FIG. 33 is a schematic top perspective view of a body member of a hinged trocar or port assembly in accordance with the present invention.

FIG. 34 is a longitudinal cross-sectional view of the port assembly body member of FIG. 33, showing the body member together with a skirt.

FIG. 35 is a top plan view of the port assembly of FIG. 33. The longitudinal cross-sectional view of FIG. 34 is taken along line XXXIV-XXXIV in FIG. 35.

FIG. 36 is a perspective view of the port assembly of FIGS. 34 and 35.

FIG. 48 is a schematic top perspective view of another trocar or port assembly in accordance with the present invention.

FIG. 49 is a longitudinal cross-sectional view of the port assembly of FIG. 48.

FIG. 50 is a side elevational view of the port assembly of FIGS. 48 and 49.

FIG. 51 is a perspective view of a lower portion of the port assembly of FIGS. 40-43, showing multiple insufflation port elements.

FIG. 66A is an exploded perspective view of a distal region of one of the cannula portions of the port assembly of FIG. 60 and which is shown in the cross-sectional view of FIG. 66;

DETAILED DESCRIPTION

Figure 1:
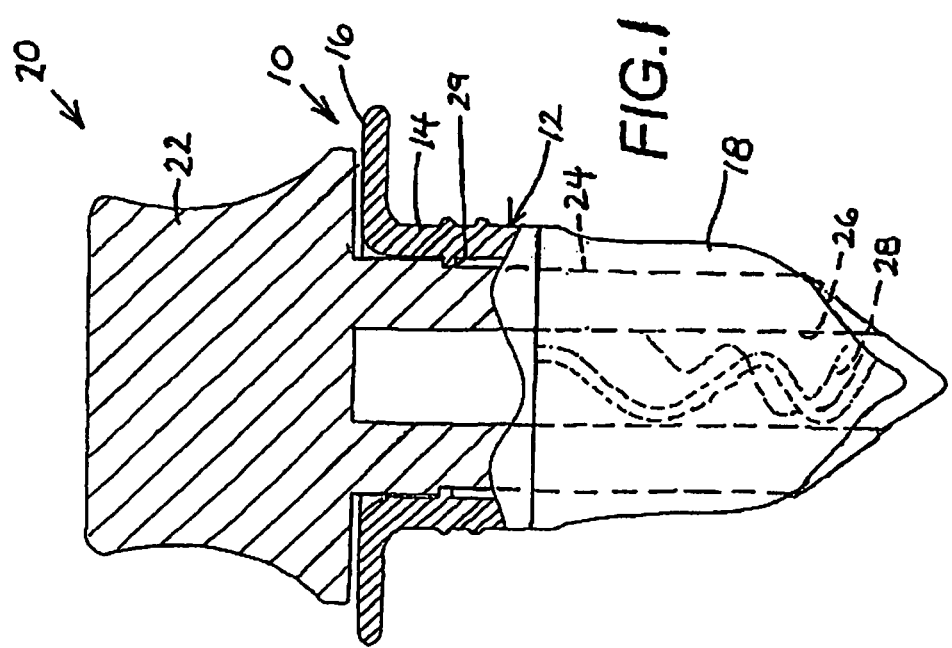
FIG. 1 is partially a schematic side elevational view and partially a schematic longitudinal cross-sectional view of a trocar or surgical port assembly in accordance with the present invention, showing a skirt folded into an obturator for deployment.

As shown in the drawings and as described throughout the following description, the term "proximal" refers to the end which is closer to the user and the term "distal" refers to the end which is further from the user.

Figure 3:
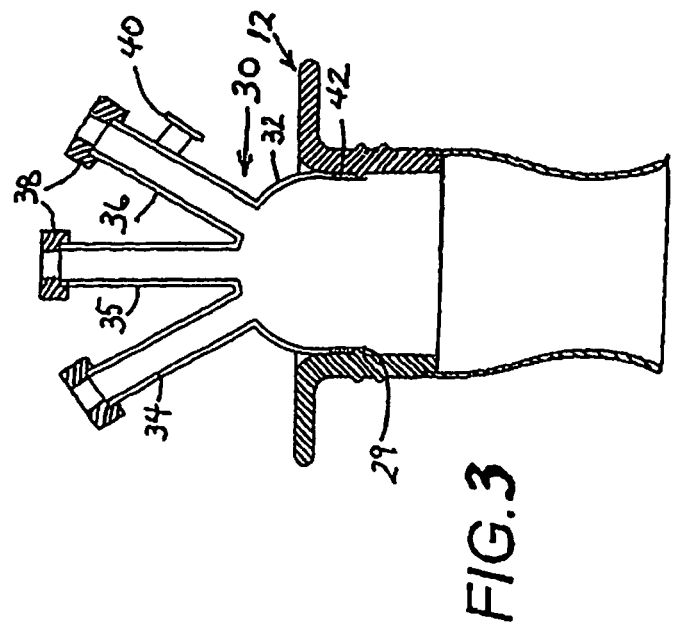
FIG. 3 is a schematic cross-sectional view of the trocar or port assembly of FIGS. 1 and 2, showing a dome with finger or seal members attached to a body member in the port assembly.
Figure 2:
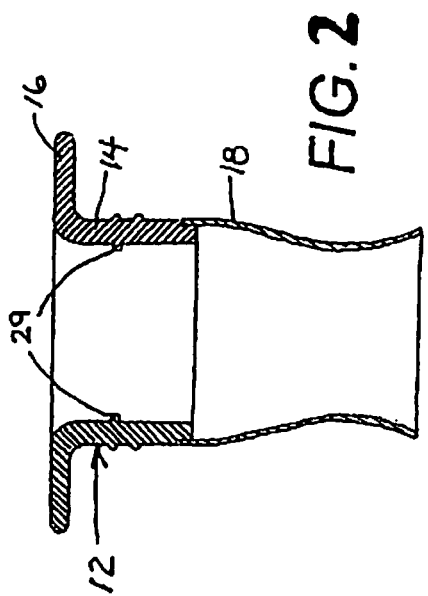
FIG. 2 is a schematic cross-sectional view of the trocar or port assembly of FIG. 1, showing the skirt in a free depending configuration.

As depicted in FIG. 1, a trocar or surgical port assembly 10 useful for laparoscopic or thoracoscopic surgery includes a rigid annular trocar body 12 having a cylindrical portion 14 and a circular flange 16 at a proximal or outer end of the cylindrical portion. Surgical port assembly 10 further includes a fabric or elastomeric skirt 18 attached to a distal end of cylindrical portion 14. An obturator 20 includes a knob or handle 22 and a rigid insertion portion 24 slidably insertable through cylindrical portion 14 of trocar body 12. Rigid insertion portion 24 is provided with a longitudinal slot 26 into which a portion 28 of skirt 18 is folded and secured for facilitating deployment of the port assembly at the onset of a minimally invasive surgical procedure. After insertion of the assembly into an incision, obturator 20 is removed, freeing the skirt, as shown in FIG. 2. Subsequently, a pneumoperitoneum maintenance component 30 (FIG. 3) is attached to trocar body 12 for enabling the passage of instrument shafts through port assembly 10 and into a patient. Cylindrical portion 14 of trocar body 12 is formed internally with an annular rib or a plurality of inwardly extending nubs 29 defining a shoulder on which obturator 20 and component 30 alternatively rest.

Component 30 comprises an elastomeric dome-shaped base 32 and a plurality of upwardly extending tubular members or cannulas 34-36 each provided with a cap 38 housing a plurality of seals (not shown). These seals include a valve (e.g., a tricuspid valve) to prevent air leakage when no instrument is inserted through the tubular member or cannula 34-36. The seals further include an instrument seal exemplarily in the form of a resilient ring or bead fixed to the internal wall of the cannula 34-36 or respective cap 38. Upon insertion of an instrument shaft through a cannula 34-36, the ring or bead hugs the instrument and prevents or minimizes the leakage of insufflation gas. Additional ring or other seals may be incorporated, particularly where the ring or bead seals are provided along a flexible portion of a tubular port member or cannula 34-36. The multiple seals prevent loss of pneumoperitoneum through a cannula 34-36 when an instrument extending therethrough is being manipulated during a procedure.

Generally, in a laparoscopic operation, one of the fingers or cannulas 34-36 receives a laparoscope, while laparoscopic instrument shafts traverse the other two. All three cannulas 34-36 extend away from trocar body 12 only on an outer or upper side thereof, facing away from a patient during a surgical procedure. The underside of the trocar body 12 is free of cannulas. One of the fingers or cannulas 36 is provided with a luer fitting 40 for enabling insufflation of a patient's abdominal cavity during laparoscopic surgery. The fitting is not needed in many thoracoscopic procedures.

Dome-shaped base 32 is provided along a lower periphery with a sealing ring 42 that engages rib or shoulder 29 on cylindrical portion 14. Sealing ring 42 has a sliding engagement with an inner surface (not labels) of cylindrical portion 14 to facilitate a rotation of component 30 about an axis 46 of body member 12. Along an outer surface (not designated), cylindrical portion 14 is formed with a plurality of outwardly extending circumferential ribs or beads 44 for inhibiting slippage in an incision.

Figure 4:
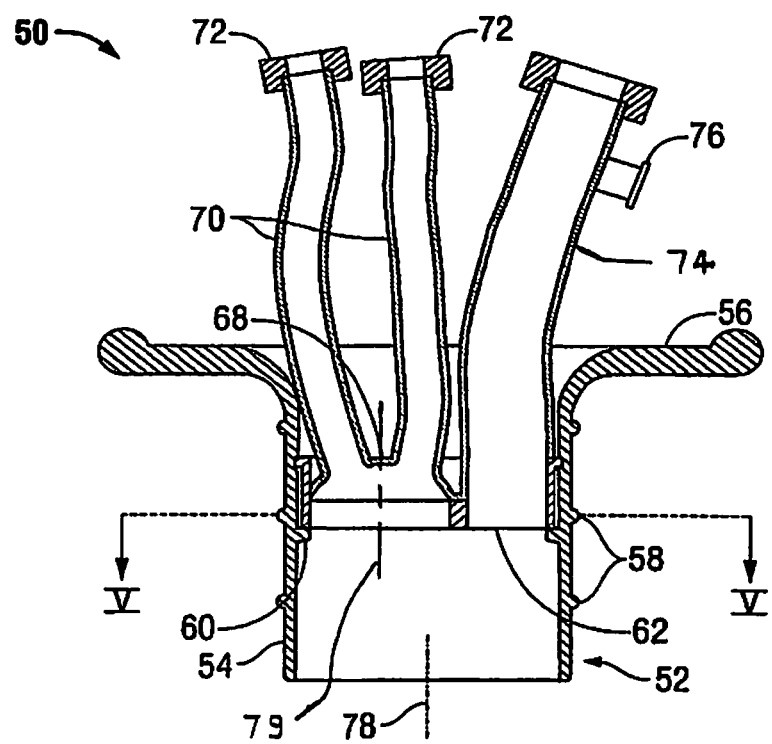
FIG. 4 is a schematic longitudinal cross sectional view of another trocar or surgical port assembly in accordance with the present invention, showing a trocar body with an apertured plate therein.
Figure 5:
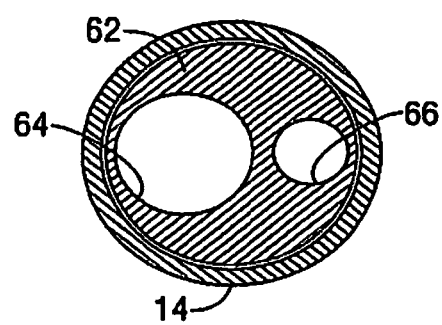
FIG. 5 is a top plan view of the plate of FIG. 4, showing a pair of openings.

As depicted in FIGS. 4 and 5, a surgical port assembly 50 comprises an annular body 52 attachable to a patient at an incision in a skin surface of the patient to facilitate deployment of instruments in the patient via the incision. More particularly, annular body 52 includes a cylindrical insert portion 54 and a flange 56 surrounding a proximal (closer to the surgeon) or outer end of the cylindrical insert portion. Insertion portion 54 is provided along an outer surface with a plurality of longitudinally spaced circular beads 58 and along an inner surface with a circular shoulder 60 (or at least three inwardly extending nubs defining a ledge). Shoulder 60 supports a rigid plate 62 formed with an instrument opening 64 and a scope opening 66. Plate 62 may be rotatably or rigidly secured to cylindrical insert portion 54 of annular body 52. An ancillary second plate 68 having a dome shape is rotatably and removably attached to the main plate 62 over opening 64. Ancillary plate 68 carries a pair of integrally formed tubular members or cannulas 70 made of a flexible material and provided at free ends with respective sealing caps 72. A third tubular sealing member or cannula 74 is attached to main plate 62 over scope opening 66 for enabling the introduction of a distal end portion of a laparoscope or other endoscope into a patient through port assembly 50. Scope cannula 74 has a luer fitting 76 for insufflation purposes. Tubular fingers or cannulas 70 and 74 extend in an upper direction away from plates 62 and 68 and are disposed only on an upper or outer side thereof, facing away from a patient during a surgical procedure. The lower or inwardly facing side of port assembly 50 is free of cannula parts.

Plate 68 is rotatably disposed in or at opening 64 for turning about an axis 78 preferably substantially parallel to a main axis 79 of port assembly 50.

Tubular fingers or cannulas 70 and 74 are flexible at least at a point of attachment to plates 68 and 62, respectively, enabling a pivoting (about a transverse axis) and/or a swiveling (about a longitudinal axis) of surgical instruments (or an endoscope) inserted through the tubular fingers or cannulas 70, 74. Fingers or cannulas 70, 74 are each provided with at least one seal for maintaining pneumoperitoneum when a surgical instrument shaft longitudinally traverses such finger or cannula and at least one seal for maintaining pneumoperitoneum in the absence of a surgical instrument shaft longitudinally traversing such finger or cannula.

FIGS. 6-8 illustrate a modified version 80 of the trocar or surgical port assembly of FIGS. 4 and 5. Surgical port assembly 80 comprises an annular body 82 attachable to a patient at an incision in a skin surface of the patient to facilitate deployment of instruments in the patient via the incision. More particularly, annular body 82 includes a cylindrical insert portion 84 and a flange 86 surrounding a proximal or outer end of the cylindrical insert portion. Insertion portion 84 is provided at a distal or inner end with an annular slot 88 that receives en edge of a skirt 90. Skirt 90 is an elastomeric annular or slotted web member in which a plurality of longitudinal support wires 92 are embedded (see FIG. 9). At least some of the wires 92 extend generally parallel to a longitudinal axis 94 of trocar body 82. Wires 92 serve to form skirt 90 into an expanded funnel shape upon deployment of the surgical port assembly 80 in a patient.

Trocar body 82 is formed along an inner surface with a ledge or plate 96 defining an instrument opening 98 and a scope opening 100. Plate 96 is rigidly secured to cylindrical insert portion 84 of annular body 82. An ancillary second plate or disk 102 is rotatably and removably attached to the main plate 96 over opening 98. A locking ring 104 may be provided (FIG. 8) for releasably holding plate or disk 102 to plate 96 at opening 98. Ancillary plate or disk 102 carries a pair of tubular fingers or cannulas 106 made of a flexible material and provided at free ends with respective sealing caps 108. Fingers or cannulas 106 may be removably attached to plate or disk 102. To that end, plate or disk 102 may be formed with a pair of outwardly extending sleeves 110 (FIG. 8) insertable into tubular fingers or cannulas 106. A third tubular sealing finger or cannula 112 is attached to main plate 96 over scope opening 100 for enabling the introduction of a distal end portion of a laparoscope or other endoscope into a patient through port assembly 80. Scope cannula 112 may have a luer fitting (not shown) for insufflation purposes. Tubular fingers or cannulas 106 and 112 extend in an upper direction away from plates 96 and 102 and are disposed only on an upper or outer side thereof, facing away from a patient during a surgical procedure. The lower or inwardly facing side of port assembly 80 is free of cannula parts.

Plate or disk 102 serves as a cannula carrier that is rotatably disposed in or at opening 98 for turning about an axis 114 preferably substantially parallel to main axis 94 of port assembly 80.

Tubular fingers or cannulas 106 and 112 are flexible at least at a point of attachment to plates 102 and 96, respectively, enabling a pivoting (about a transverse axis) and/or a swiveling (about a longitudinal axis) of surgical instruments (or an endoscope) inserted through the ports formed by tubular fingers or cannulas 106, 112. Fingers or cannulas 106, 112 are each provided with at least one seal for maintaining pneumoperitoneum when a surgical instrument shaft longitudinally traverses such finger or cannula and at least one seal for maintaining pneumoperitoneum in the absence of a surgical instrument shaft longitudinally traversing such finger or cannula.

FIG. 6 shows an obturator shaft 118 and skirt 90 folded and tucked into a slot along shaft 118. A knob (not shown) at the proximal or outer end of obturator shaft 118 is pushed to release skirt 90 from obturator shaft 118. The obturator is then pulled out and discarded. A release and discard safety tab is shown at 120.

Figure 10:
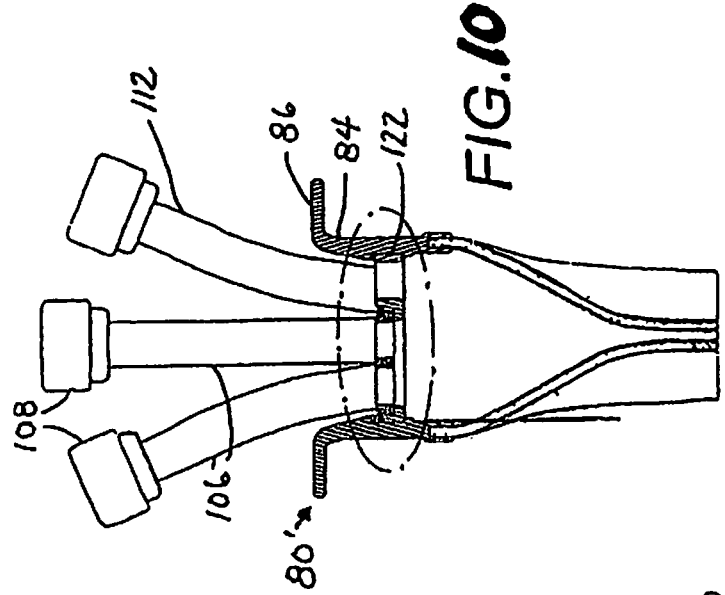
FIG. 10 is a schematic longitudinal cross-sectional view of another modified trocar or surgical port assembly in accordance with the present invention, largely similar to the port assembly of FIGS. 6-8.
Figure 11:
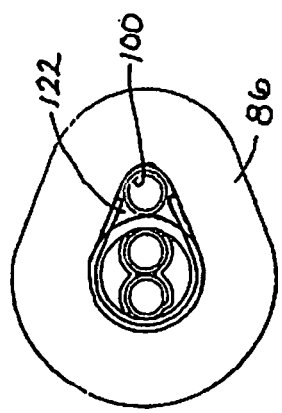
FIG. 11 is a top plan view of the trocar or surgical port assembly of FIG. 10, showing three instrument ports.
Figure 12:
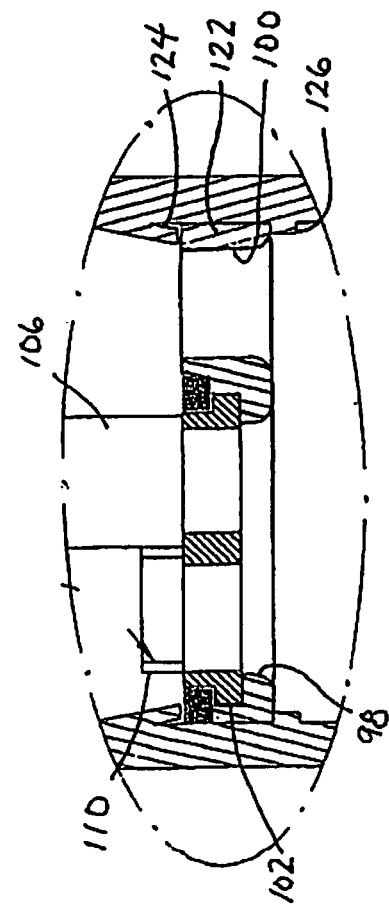
FIG. 12 is a partial schematic cross-sectional view, on a larger scale, of the modified trocar or surgical port assembly of FIGS. 10 and 11.

FIGS. 10-12 depict a port assembly 80' that is a modified version of port assembly 80 of FIGS. 6-8. The same reference numerals are used in FIGS. 10-12 to designate the same parts as shown in FIGS. 6-8. Instead of integral or unitary main plate 96, port assembly 80' has a removable main plate 122 that is releasably secured to cylindrical insertion portion 84 via a plurality of spring-loaded detents 124. Main plate 122 sits on an inwardly extending shoulder 126 (or series of nubs) and is held thereto in a snap lock fit by the plurality of spring-loaded detents 124.

As shown in FIGS. 13 and 14, another trocar or surgical port assembly 130 comprises an annular body 132 attachable to a patient at an incision in a skin surface of the patient to facilitate deployment of instruments in the patient via the incision. Annular body 132 includes a substantially oval insert portion 134 and a flange 136 at a proximal (closer to the surgeon) or outer end of the cylindrical insert portion. Insertion portion 134 is provided along an outer surface with a plurality of longitudinally spaced circular beads 138 and along an inner surface with a substantially annular or endless groove 140. A skirt (not shown) may be attached to an inner or distal end 142 of cylindrical insert portion 134.

Groove 140 receives an outer end of a rigid support or base plate 144 provided with three slots 146-148. Central slot 147 is intended for insertion of a laparoscope in an abdominal operation, while lateral slots 146 and 148 are intended for the passage of instrument shafts. An ancillary second plate 150 made of elastomeric material having a dome shape is attached to the support or base plate 144 over opening slots 146-148. Base plate 144 and ancillary plate 150 have a generally elongate or oval cross-section, as seen in FIG. 14. Ancillary plate 150 carries three integrally formed tubular members or cannulas 152 (one provided with a luer fitting 154 for insufflation) made of flexible elastomeric material and provided at free ends with respective sealing caps 156. Tubular fingers or cannulas 152 extend in an upper direction away from plates 144 and 150 and are disposed only on an upper or outer side thereof, facing away from a patient during a surgical procedure. The lower or inwardly facing side of port assembly 130 is free of cannula parts.

Tubular fingers or cannulas 152 are flexible at least at a point of attachment to plate 150, enabling a pivoting (about a transverse axis) and/or a swiveling (about a longitudinal axis) of surgical instruments (or an endoscope) inserted through the tubular fingers or cannulas. Fingers or cannulas 152 are each provided (for instance, in caps 156) with at least one seal for maintaining pneumoperitoneum when a surgical instrument shaft longitudinally traverses such finger or cannula and at least one seal for maintaining pneumoperitoneum in the absence of a surgical instrument shaft longitudinally traversing such finger or cannula.

As shown in FIGS. 15-17, a further trocar or surgical port assembly 160 comprises an annular body 162 attachable to a patient at an incision in a skin surface of the patient to facilitate deployment of instruments in the patient via the incision. Annular body 162 includes a cylindrical insert portion 164 and a flange 166 at a proximal or outer end of the cylindrical insert portion. A skirt (not shown) may be attached to an inner or distal end 168 of cylindrical insert portion 164.

A groove 170 provided in a widened section 172 of cylindrical insertion portion 164 permanently receives an outer periphery of a perforated support or base plate 174. Plate 174 may be made of a rigid (e.g. metallic) or elastomeric material and is formed with three instrument openings 176 and a smaller insufflation opening 178. Three elastomeric tubular fingers or cannulas 180 are connected to plate 174 and communicate with respective openings 176. In the case of an elastomeric base plate 174, cannulas 180 are formed integrally therewith. Tubular fingers or cannulas 180 are flexible at least at a point of attachment to plate 174, enabling a pivoting and/or swiveling of surgical instruments (or an endoscope) inserted through the tubular fingers or cannulas. Fingers or cannulas 152 are each provided with at least one inner ring seal 182 for maintaining pneumoperitoneum when a surgical instrument shaft longitudinally traverses such finger or cannula and at least one seal (e.g., a tricuspid valve at a lower end 184) for maintaining pneumoperitoneum in the absence of a surgical instrument shaft longitudinally traversing such finger or cannula.

Tubular fingers or cannulas 180 serve to seal the abdominal cavity during pneumoperitoneum and further serve to protect the patient's internal tissues, such as the abdominal wall tissues. Fingers or cannulas 180 extend only downwardly or inwardly away from support or base plate 174, on the inner side of the trocar body 162.

FIGS. 18 and 19 show a scheme for deploying the port assembly 160 of FIGS. 15-17. A rigid mounting ring 186 is disposed on a skin surface SS over a patient's abdominal cavity AC and attached to the skin via sutures 188 and 190. Sutures 188 and 190 are sewn at one end 192 to the patient and are tied at opposing ends to respective dual-hook members 194 that are upwardly inclined from mounting ring 186. An outer periphery (not labeled) of flange 166 is slidably inserted into an annular groove 196 provided on an inner surface of mounting ring 186. Cylindrical portion 164 of port assembly body 162 depends downwardly into the abdominal wall AW of a patient during a surgical procedure. Fingers or cannulas 180 extend through a portion of abdominal wall AW and into an abdominal cavity AC of the patient. Trocar body 162 may be turned about a longitudinal axis 198 of port assembly 160, while mounting ring 186 remains stationary relative to the patient, to facilitate the manipulation of laparoscopic instruments (not shown) whose shafts are inserted through respective fingers or cannulas 180.

FIGS. 20 and 21 depict an alternative surgical access port assembly 200 comprising an annular body 202 attachable to a patient at an incision NCSN in a skin surface SS of the patient to facilitate deployment of instruments in the patient via the incision. Annular body 202 includes a mounting ring 204 fixed to an adhesive pad 206 that in turn is releasably adhered to skin surface SS about incision NCSN. Port assembly 200 further comprises a rigid plate 208 rotatably or rigidly secured to mounting ring 204 via a locking ring 210. Plate 208 may be made of a rigid (e.g. metallic) or elastomeric material and is formed with three instrument openings 212 and a smaller insufflation opening (not shown). Three elastomeric tubular fingers or cannulas 214 are connected to plate 208 and communicate with respective openings 212. In the case of an elastomeric base plate 208, cannulas 214 are formed integrally therewith. Tubular fingers or cannulas 214 are flexible at least at a point of attachment to plate 208, enabling a pivoting and/or swiveling of surgical instruments (or a scope) inserted through the tubular fingers or cannulas. Fingers or cannulas 214 are each provided with at least one inner ring seal (not sown) for maintaining pneumoperitoneum when a surgical instrument shaft longitudinally traverses such finger or cannula and at least one seal (e.g., a tricuspid valve at a lower end 216) for maintaining pneumoperitoneum in the absence of a surgical instrument shaft longitudinally traversing such finger or cannula.

Tubular fingers or cannulas 214 serve to seal the abdominal cavity AC during pneumoperitoneum in a laparoscopic procedure and further serve to protect the patient's internal tissues, such as the tissues of abdominal wall AW. Fingers or cannulas 214 extend only downwardly or inwardly away from support or base plate 208, on the inner side of the body 202. Fingers or cannulas 214 can accommodate instrument shafts that are fully flexible as well as instruments shaft that have preformed rigid shapes, including C-shaped and S-shaped portions.

As illustrated in FIGS. 22 and 23, another trocar or surgical port assembly 220 comprises an annular body 222 attachable to a patient at an incision in a skin surface of the patient to facilitate deployment of instruments in the patient via the incision. Annular body 222 includes a cylindrical insert portion 224 and a flange 226 at a proximal or outer end of the cylindrical insert portion. A skirt 228 is attached to an inner or distal end 230 of cylindrical insert portion 224. Skirt 228 includes a flexible web 232 and a stent wire 234 attached to the web (e.g., inserted into a cavity or pocket, not shown, formed in the web). Wire 234 has a zig-zag or snaking configuration and serves to spring-bias web 232 into a conical or funnel-shaped open configuration shown in FIG. 23. Trocar or surgical port assembly 220 additionally comprises a purse-string closure element 236 disposed about a distal or free end of skirt 228 for the skirt in a closed or pointed insertion configuration (FIG. 22) in opposition to the opening force exerted by wire 234. Purse string closure element 236 is connected to a deployment knob or button 237 via an obturator shaft 238. Upon insertion of folded or pointed skirt 228 (FIG. 22) and cylindrical insert portion 224 into an abdominal wall of a patient, the user actuates knob or button 237 to release purse-string closure element 236, thereby enabling the opening of skirt 228 into the opened funnel-shaped use configuration (FIG. 23) under the biasing force exerted by wire 234.

Trocar or surgical port assembly 220 of FIGS. 22 and 23 comprises additional structure described hereinabove with reference to FIGS. 10-12. The same reference numerals are used in FIGS. 10-12 and 22, 23 to designate identical structures. In FIGS. 22 and 23, fingers or cannulas 106 and 112 are additionally shown with sealing structures 239.

Figure 25:
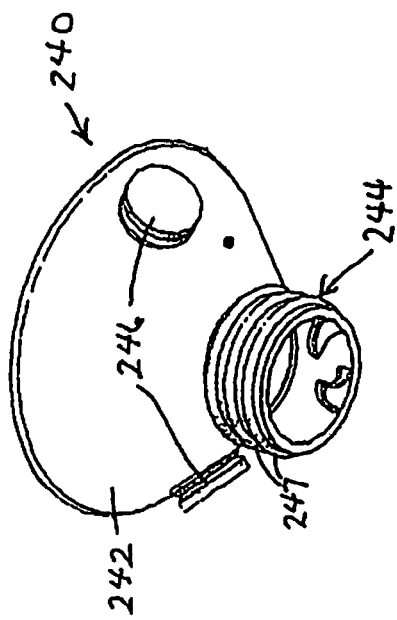
FIG. 25 is a schematic perspective bottom view of the surgical port assembly of FIG. 24.
Figure 24:
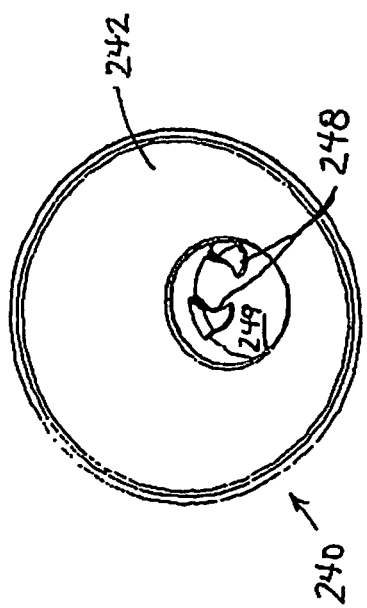
FIG. 24 is a schematic perspective top view of another surgical port assembly in accordance with the present invention.

As shown in FIGS. 24 and 25, another trocar port assembly 240 comprises a body member (not separately designated) including a funnel-shaped upper or proximal portion 242 and a cylindrical lower or distal portion 244. Upper or proximal portion 242 is provided along a conical outer surface (not separately labeled) with a plurality of laterally grooved cylindrical posts 246 for receiving tie-down sutures (not shown) to anchor the trocar port assembly 240 to a patient at an incision site (such as the umbilicus). Cylindrical portion 244 is provided along an outer surface with a plurality of annular ribs 247 for enhancing a seating of the cylindrical portion in an incision. On an inner surface and at a bottom or distal end, cylindrical portion 244 is provided with a pair of opposing generally arcuate teeth or prongs 248 that serve to hold or lock a laparoscope or other endoscope in a position at the outlet end of cylindrical portion 244. During a surgical procedure, laparoscopic instrument shafts (not shown) longitudinally traverse flexible fingers or cannulas (not shown) that pass through an open area 249 in the bottom or distal end of cylindrical portion 244.

Figure 26:
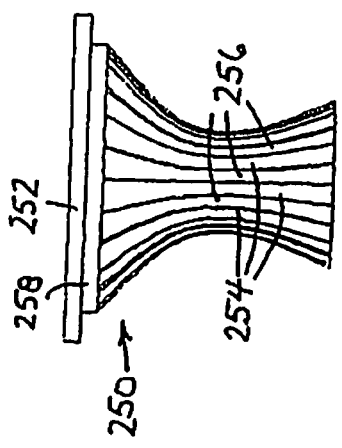
FIG. 26 is a schematic top perspective view of an expandable skirt utilizable in a surgical port assembly in accordance with the present invention.
Figure 27:
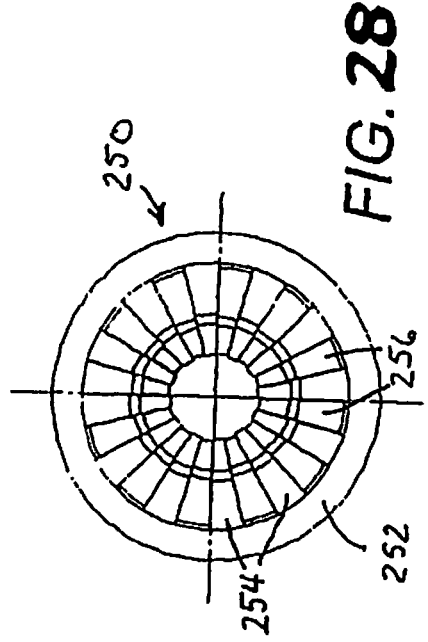
FIG. 27 is a side elevational view of the skirt of FIG. 26.
Figure 28:
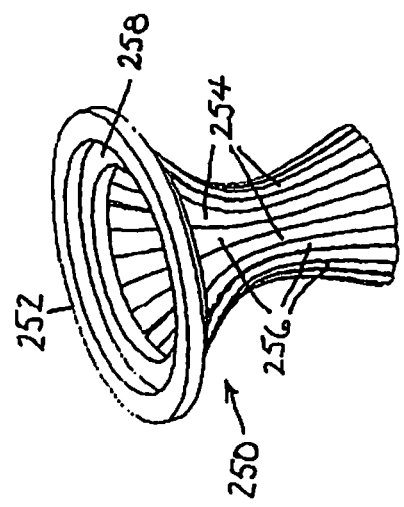
FIG. 28 is a top view of the skirt of FIGS. 26 and 27.
Figure 29:
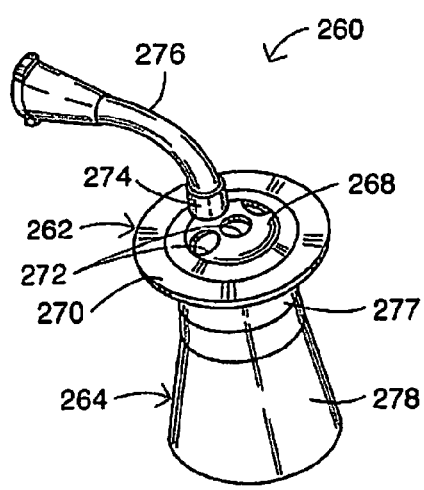
FIG. 29 is a schematic top perspective view of an elastomeric two-shot domed trocar or port assembly in accordance with the present invention.
Figure 30:
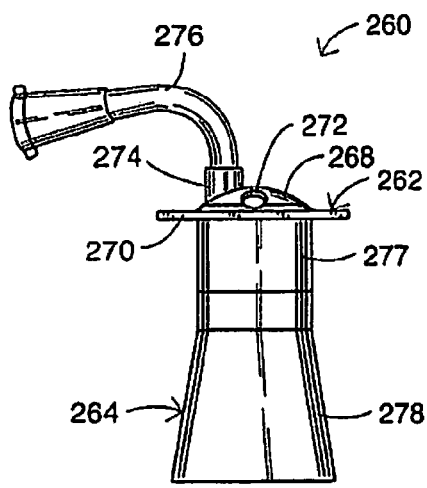
FIG. 30 is a side elevational view of the port assembly of FIG. 29.
Figure 31:
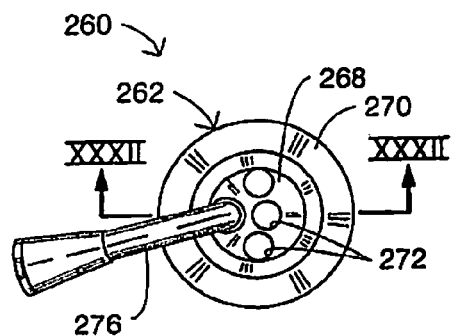
FIG. 31 is a top plan view of the port assembly of FIGS. 29 and 30.
Figure 32:
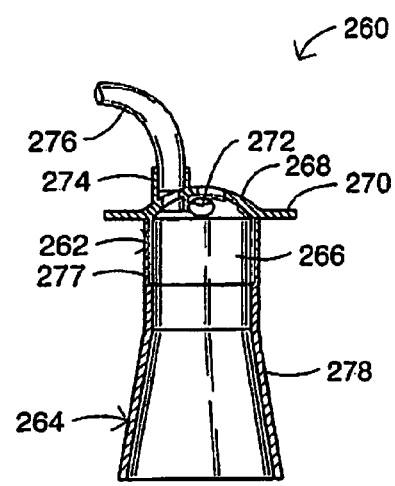
FIG. 32 is a longitudinal cross-sectional view taken along line XXXII-XXXII in FIG. 31.

FIGS. 26-28 illustrate a trocar skirt 250 comprising a rigid support ring 252, a multiplicity of substantially rigid strips or bands 254 connecting to one another via elastomeric sections 256. Rigid strips 254 are arranged in an annular configuration and are concave in a radially outward direction. Elastomeric sections 256 may be angularly or circumferentially spaced portions of a single web or separate strips. Rigid strips or bands 254 are pivotably attached at an upper or proximal end to a mounting ring 258 in turn fastened to support ring 252. The pivotable attachment of strips or bands 254 to mounting ring 258 may take the form of a so-called living hinge, for example, wherein mounting ring 258 and strips or bands 254 are integrally made of a substantially rigid polymeric material that is sufficiently thin at connecting points to enable a pivoting and/or swiveling motion.

Elastomeric sections 256 of trocar skirt 250 are capable of stretching sufficiently to permit a full range of instrument and scope motion during a surgical procedure while protecting a patient's abdominal tissues. Trocar skirt 250 has a corset shape, with a waist diameter that may alternately increase and decrease during instrument manipulation.

Trocar skirt 250 is attached to an underside of a trocar assembly such as the port assemblies described hereinabove with reference to FIGS. 1-14.

As shown in FIGS. 29-32, a trocar or surgical port assembly 260 comprises an upper or proximal body 262 and a skirt 264. Body 262 is made of a flexible elastomeric material and includes a cylindrical portion 266, a dome 268 and a circumferential or annular disk-shaped flange 270. Dome 268 is formed with a plurality of openings 272 for the passage of laparoscopic or thoracoscopic instrument shafts (not shown) and a laparoscope or endoscope (not shown). Openings 272 are formed with slit-type seals for preventing the loss of pneumoperitoneum both when instruments shafts pass through the openings and when there are no instruments traversing the openings. Dome 268 is further formed with a tubular stub 274 that receives a distal end of an insufflation tube 276. Skirt 264 includes a cylindrical proximal sleeve 277 that fits over and is functionally connected to cylindrical portion 266. Skirt 264 further includes a resilient frusto-conical portion 278 that is folded and preferably held to an obturator shaft during insertion through an incision.

FIGS. 33-36 depict a trocar or surgical port assembly 280 including a body 282 having a cylindrical portion (not separately designated) formed by a plurality of cylindrical sections or flaps 284 swingably connected to a ring-shaped base member 285 in the nature of a flange to the cylindrical portion. Flaps 284 are made of at least a substantially rigid material and each include plural longitudinally spaced arcuate ribs 286 along a respective outer surface. Flaps 284 each have a hinge projection 288 that is inserted through a slot 290 in base member 285. Projections 288 are hooked, to prevent a disassociation of flaps 284 from base member 285. Base member 285 is provided with a plurality of upwardly or proximally extending arcuate flange sections 292 that are received into a distal or lower end of a cylindrical body of a flexible-cannula port member such as the domed members of FIGS. 3 and 13, 14.

Surgical port assembly 280 further comprises a skirt 294 including a cylindrical proximal sleeve 296 that fits over flaps 284 and is thereby functionally connected to body 282. Skirt 294 further includes a resilient frusto-conical portion 298 that is folded and preferably held to an obturator shaft during insertion through an incision.

Figure 37:
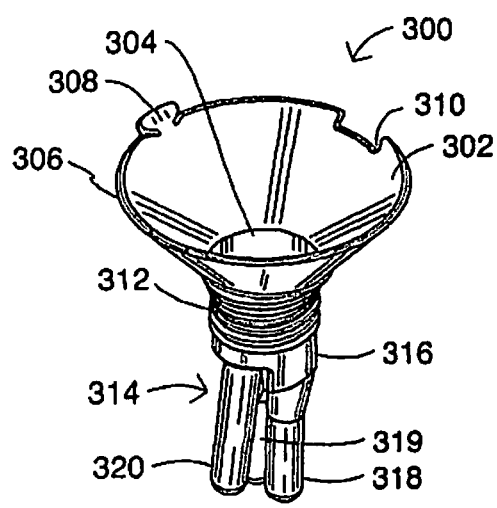
FIG. 37 is a schematic top perspective view of yet another trocar or port assembly in accordance with the present invention.
Figure 38:
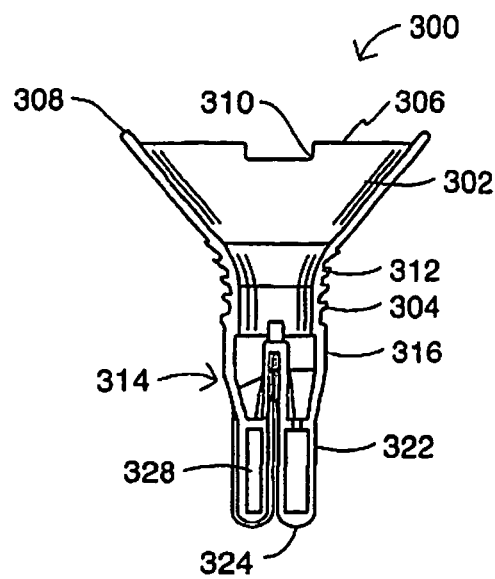
FIG. 38 is a longitudinal cross-sectional view of the port assembly body member of FIG. 37.
Figure 39:
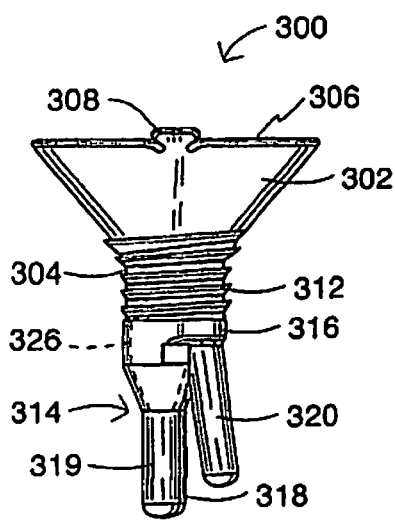
FIG. 39 is a side elevational view of the port assembly of FIGS. 37 and 38.

As shown in FIGS. 37-39, yet another trocar port assembly 300 comprises a body member (not separately designated) including a funnel-shaped upper or proximal portion 302 and a cylindrical lower or distal portion 304. Upper or proximal portion 302 is provided along a circular rim 306 with a plurality of suture anchors 308 in the form of substantially flat, generally triangular upwardly inclined posts for receiving tie-down sutures (not shown) to anchor the trocar port assembly 300 to a patient at an incision site (such as the umbilicus). Upper or proximal portion 302 is additionally provided along circular rim 306 with a plurality of rectangular recesses 310 for receiving mating projections on an obturator (see FIGS. 45-47). Cylindrical portion 304 is provided along an outer surface with a helical thread or one or more outwardly extending ribs 312 for enhancing a sealed seating of the cylindrical portion in an incision.

Figure 40:
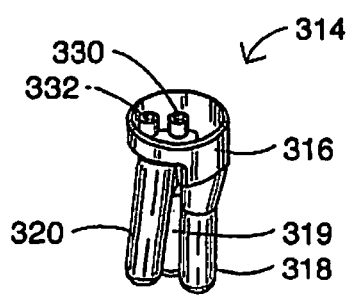
FIG. 40 is a perspective view of a lower portion of the port assembly of FIGS. 37-39, showing multiple insufflation port elements.

Port assembly 300 further includes, at a bottom or distal end (not separately enumerated) of cylindrical portion 304, an elastomeric "pants" member 314 illustrated separately in FIG. 40. Pants member 314 includes a cannula carrier 316 and cannula members in the form of three elastomeric legs or downwardly depending fingers 318, 319, 320 that are each provided with an inwardly extending ring seal 322 and a tricuspid seal 324. Leg 320 is dedicated to the passage of a scope (not shown), while the remaining two legs 318, 319 have a wider and deeper entrance space or antechamber 326 allowing an increased range of instrument motion and an easier crossing of the instrument shafts (not shown).

Legs or fingers 318-320 are provided internally with polytetrafluorethylene stiffening tubes 328 that provide strength and rigidity and reduce friction. Stiffening tubes 328 facilitate the withdrawal of laparoscopic instrument shafts (including scopes) by preventing the entrainment of the instrument shafts to the legs or fingers 318-320. Accordingly, stiffening tubes 328 prevent a turning inside-out of legs or fingers 318-320.

Figure 45:
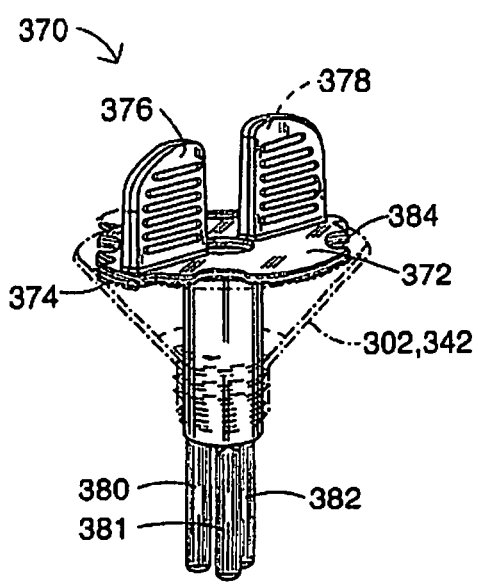
FIG. 45 is a schematic top perspective view of a three-fingered obturator, in accordance with the present invention, exemplarily for use in deploying the trocar or port assembly of FIGS. 37-40 or FIGS. 41-44 in a patient at the onset of a minimally invasive laparoscopic or thoracoscopic surgical procedure.
Figure 46:
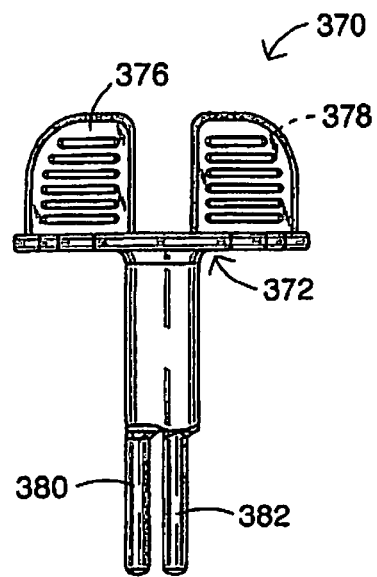
FIG. 46 is a side elevational view of the obturator of FIG. 45.
Figure 47:
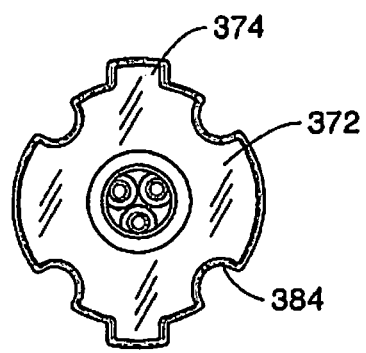
FIG. 47 is a top plan view of the obturator of FIGS. 45 and 46.

Legs, fingers or cannulas 318-320 are flexible in a region of attachment to domed cannula carrier 316, whereby the legs/fingers/cannulas may be temporarily bent into a parallel configuration for insertion into a patient through an incision with the aid of an obturator (see FIGS. 45-47).

As shown in FIG. 40, cannula carrier 316 of pants member 314 includes multiple insufflation ports 330 and 332 providing an option of connecting insufflation hoses (not shown) at a center (330) or a periphery (332).

As depicted in FIGS. 41-44, a similar trocar port assembly 340 comprises a body member 341 including a rigid conical upper or proximal portion 342 and a cylindrical lower or distal portion 344. Upper or proximal portion 342 is provided along a circular rim 346 with a plurality of suture anchors 348 in the form of substantially flat, generally triangular upwardly inclined posts for receiving tie-down sutures (not shown) to anchor the trocar port assembly 340 to a patient at an incision site (such as the umbilicus). Upper or proximal portion 342 is additionally provided along circular rim 346 with a plurality of rectangular recesses 350 for receiving mating projections on an obturator (see FIGS. 45-47). Cylindrical portion 344 is provided along an outer surface with a helical thread or one or more outwardly extending ribs 352 for enhancing a sealed seating of the cylindrical portion in an incision.

Figure 44:
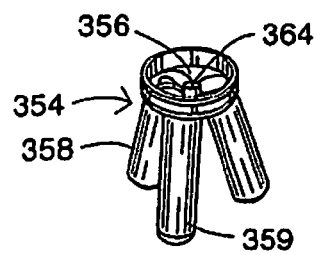
FIG. 44 is a perspective view of a lower portion of the port assembly of FIGS. 40-43, showing multiple insufflation port elements.

Port assembly 340 further includes, at a bottom or distal end (not separately enumerated) of cylindrical portion 344, an elastomeric "pants" member 354 illustrated separately in FIG. 44. Pants member 354 includes a domed cannula carrier 356 and cannula members in the form of three elastomeric legs or downwardly depending fingers 358, 359, 360 that are each provided with (i) a ring seal 322 in the form of an annular bead and (ii) a tricuspid insufflation seal 324. Legs 358-360 are identical and interchangeably used for the passage of a scope (not shown) or surgical instrument shafts (not shown). Legs 358-360 are circumferentially equispaced and outwardly inclined in a mutually flared configuration.

Legs or fingers 358-360 are lined with polytetrafluorethylene stiffening tubes 362 that strengthen and rigidify the major portions of the legs and additionally reduce friction between the instrument shafts and the legs. During the withdrawal of laparoscopic instrument shafts (including scopes) from legs or fingers 358-360, stiffening tubes 362 prevent the entrainment of the instrument shafts to the legs or fingers. Thus, stiffening tubes 362 prevent legs or fingers 358-360 from turning inside out.

Legs, fingers or cannulas 358-360 are flexible in a region of attachment to domed cannula carrier 356, thereby enabling a temporary deformation of the cannulas into a parallel configuration for insertion into a patient through an incision with the aid of an obturator (see FIGS. 45-47). Legs, fingers or cannulas 358-360 are provided at an upper or proximal end with circumferential rind seals 361 and at a lower or distal end 363 with tricuspid seals.

Figure 41:
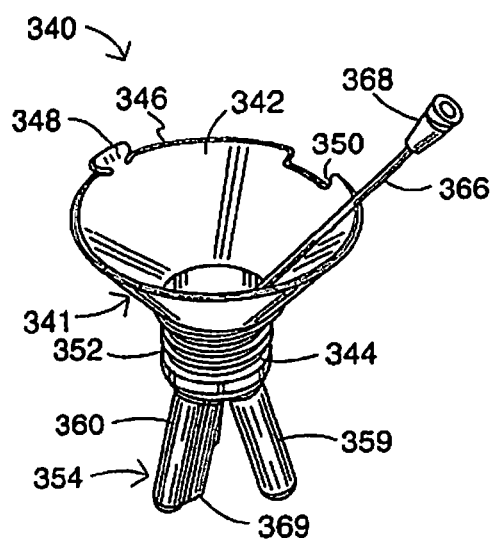
FIG. 41 is a schematic top perspective view of another trocar or port assembly in accordance with the present invention, similar to the trocar or port assembly of FIGS. 37-39.
Figure 42:
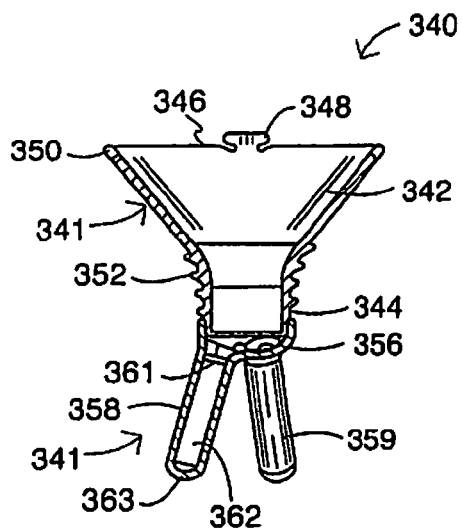
FIG. 42 is a longitudinal cross-sectional view of the port assembly of FIG. 41.
Figure 43:
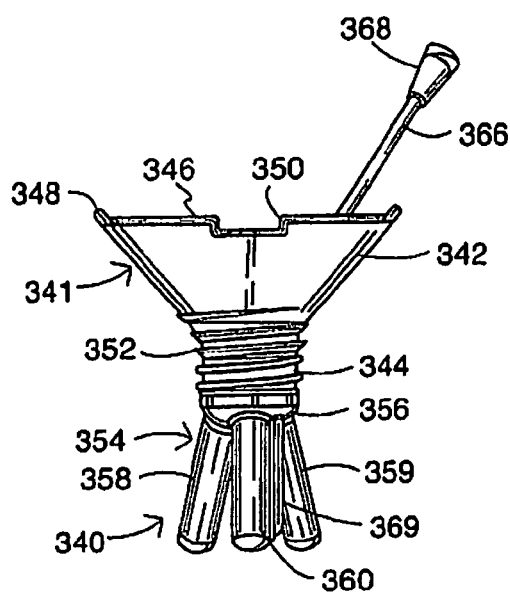
FIG. 43 is a side elevational view of the port assembly of FIGS. 41 and 42.

As depicted in FIG. 44, cannula carrier 356 of pants member 354 may include a central insufflation port 364 with an outlet (not shown) on an outer or distal surface (not separately designated) of domed cannula carrier 356. Alternatively or additionally, as depicted in FIGS. 41 and 43, an insufflation tube 366 with a luer lock 368 may extend through domed carrier 356 and alongside a leg 360, as indicated at 369.

FIGS. 45-47 illustrate an obturator 370 for deployment of a surgical port assembly such as assembly 300 or 340 through a skin surface of a patient. Obturator 370 comprises a disk-shaped body member 372, locking formations 374 in the form of generally rectangular keys projecting radially outwardly from body member 372 and releasably engageable with cooperating locking formations on port assembly 300 or 340, namely rectangular recesses 310 or 350. At least two finger contact surfaces 376 and 378 are provided on body member 372, the finger contact surfaces facing in substantially opposed directions, for enabling manual application of a torque to the body member. In the illustrated embodiment, finger contact surfaces 376 and 378 are formed on respective upstanding tabs (not separately designated) disposed along a diameter of body member 372. Obturator 370 further comprises at least one elongate rigid member 380 extending away from the body member on a side thereof opposite finger contact surfaces 376 and 378, for penetrating through a skin surface of a patient.

In the illustrated embodiment, rigid penetrating member 380 is one of three parallel elongate rigid members 380, 381, 382 extending away from body member 372 on a side thereof opposite finger contact surfaces 376 and 378, for penetrating through a skin surface. Rigid members 380-382 insert into respective downwardly depending tubular leg or finger members 318-320 or 358-360 of port assembly 300 (FIG. 37-40) or 340 (FIGS. 41-44). Rigid members 380-382 serve to stiffen and hold tubular leg or finger members 318-320 or 358-360 when port assembly 300 or 340 is being deployed at the onset of a minimally invasive surgical procedure, for example, a laparoscopic or thoracoscopic operation.

Disk or body member 372 is formed along a periphery with one or more cutouts 384 serving as insufflation tube exit paths.

Obturator 370 allows for easy insertion of any trocar or port assembly having three distal leg or finger seals. After the trocar or instrument port assembly is in place, the obturator is simply pulled out of the port assembly and the minimally invasive laparoscopic or thoracoscopic procedure can begin.

As shown in FIGS. 48-51, a surgical port assembly 390 comprises a body member 392 that includes a rigid conical upper or proximal portion 394 and a cylindrical lower or distal portion 396. Cylindrical portion 396 is formed along an outer surface with a helical sealing thread or one or more outwardly extending ribs 398.

Upper or proximal portion 394 is provided along a circular rim 400 with a plurality of suture anchors 402 in the form of substantially flat, upwardly inclined posts for receiving tie-down sutures (not shown) to anchor the trocar port assembly 390 to a patient at an incision site (such as the umbilicus). Upper or proximal portion 394 is additionally provided along circular rim 400 with a plurality of rectangular recesses 406 for receiving mating projections or keys 374 on obturator body member 372 (see FIGS. 45-47).

Surgical port assembly 390 further comprises an elastomeric skirt 408 attached to a distal edge of cylindrical portion 396. Skirt 408 provides a protective barrier between laparoscopic instrument shafts (as well as their operative tips) and abdominal wall tissues. At an upper or proximal end, skirt 408 is formed with a transverse membrane 410 provided with a pair of upwardly extending sleeves 412 for receiving laparoscopic instruments. A downwardly extending third sleeve 414 is provided for the passage of a scope. Sleeves 412 and 414 are provided at upper ends with circumferential ring seals 416 engageable with instrument shafts during an operation. In addition, membrane 410 is formed with tricuspid seals 418 at the lower ends of sleeves 412. Sleeve 414 also has a tricuspid seal at a lower end.

An insufflation tube 419 with a luer lock 419' extends inside conical upper portion 394 and is attached to membrane 410 so as to provide a fluid communication pathway therethrough.

Figure 52:
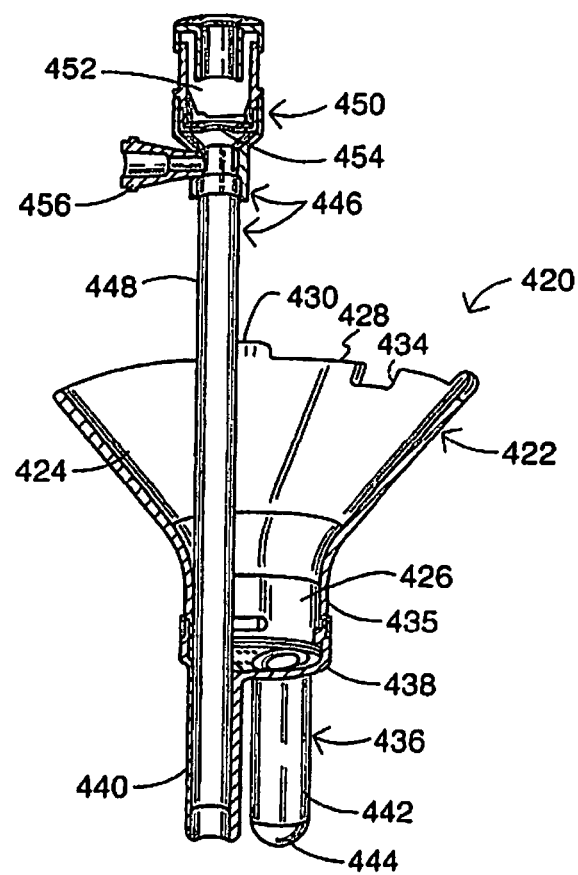
FIG. 52 is a schematic perspective view, partially cut away, of yet another trocar or port assembly in accordance with the present invention.

As depicted in FIG. 52, a laparoscopic trocar or port assembly 420 comprises a body member 422 including a funnel-shaped upper or proximal portion 424 and a cylindrical lower or distal portion 426. Upper or proximal portion 424 is provided along a circular rim 428 with a plurality of suture anchors 430 in the form of substantially flat, upwardly inclined posts with clamping slots or indentations 432 at rim 428 for receiving tie-down sutures (not shown) to anchor the trocar port assembly 420 to a patient at an incision site (such as the umbilicus). Upper or proximal portion 424 is additionally provided along circular rim 428 with a plurality of rectangular recesses 434 for receiving projections or keys 374 of obturator 370 (see FIGS. 45-47). Cylindrical portion 426 is provided along an outer surface with a helical thread or one or more outwardly extending ribs 435 for enhancing a sealed seating of the cylindrical portion in an incision.

Port assembly 420 further includes, at a bottom or distal end (not separately enumerated) of cylindrical portion 426, an elastomeric "pants" member 436. Pants member 436 includes a base or cannula carrier 438 and tree cannula members in the form of elastomeric legs or downwardly depending fingers 440 and 442 (only two shown). Two legs 442 are each provided with an inwardly extending ring seal (not shown) and a tricuspid seal at a lower or distal end 444. Leg 440 is dedicated to the passage of a scope (not shown) and is provided with a dedicated cannula 446 having a tubular member 448 that is inserted into leg 440 and rests at a lower end against a shoulder 448 on an inner surface (not designated) of leg 440. At an upper or proximal end, cannula 446 has a valve assembly 450 including a tricuspid seal 452, a ring seal 454, and an insufflation port 456. Cannula 446 may be removably inserted into leg 440 and held there by a friction fit.

Legs or fingers 442 may be provided internally with stiffening tubes (not shown) that provide strength and rigidity and reduce friction. Legs 442 are flexible at least in a region of attachment to carrier 438, whereby the legs/fingers/cannulas may be temporarily bent into inclined attitudes in response to forces exerted via laparoscopic instruments shafts during a surgical procedure.

As illustrated in drawings described hereinabove, a skirt for a trocar or surgical port assembly for minimally invasive surgery has a 360.degree. circumferential extent. However, it is possible for a trocar or port assembly skirt to extend less than 360.degree. around. This can be particularly useful where the trocar or port assembly is purposefully or inadvertently dislodged from a fully inserted position. In that event, a partial skirt with a longitudinal gap or slot can contract and close the slot, thereby permitting further instrument movements while still providing protection to abdominal wall tissues.

A partial skirt may provide for a better range of motions than a full skirt. When instruments are at their extreme lateral positions, a full skirt may restrict the instruments' movements, while partial skirt will not. Moreover, in practice the skirt must be attached (glued, etc.) to the rigid portion of the port. A full skirt will occupy the entire circumference of the cylindrical portion of the port assembly body member, while a partial skirt will occupy only a section of the cylindrical portion. The consequential spatial reduction may be significant when a small cavity wall incision is necessary or desirable. Finally, a partial skirt might be less expensive to manufacture.

As disclosed herein, a skirt may be used in combination with seal-containing cannulas or fingers that extend either above or below the body of a surgical port assembly. In the latter case, one or more downwardly depending cannulas or leg members may be used in combination with a full or partial skirt. The cannulas or fingers may be shortened while still carrying the sealing elements, while the skirt serves the tissue protection function.

A cannula module pursuant to the present disclosure may comprise a cannula-carrying member and a plurality of cannulas, fingers, or legs attached thereto. As discussed hereinabove, the carrier member may be dome-shaped above or below the body member of a surgical port assembly. The cannula module may be removably attached to a port assembly body member to enable switching of one cannula module with another during a surgical procedure, depending on specific exigencies as they arise. Thus, an "octopus" module with two legs (for a scope and one larger instrument) could replace a module with three legs or cannulas. When a cannula module is removed, the opening in the body member could be used for tissue evacuation or other procedure that requires a large access opening. Pneumoperitoneum is quickly re-established upon connection of a new cannula module. A temporary port plug fitting into the opening of the body member (e.g., into a cylindrical portion) may be provided to minimize this inconvenience. A plug minimizes or eliminates gas leakage from the abdomen of the patient during an exchange of the instruments.

Figure 53:
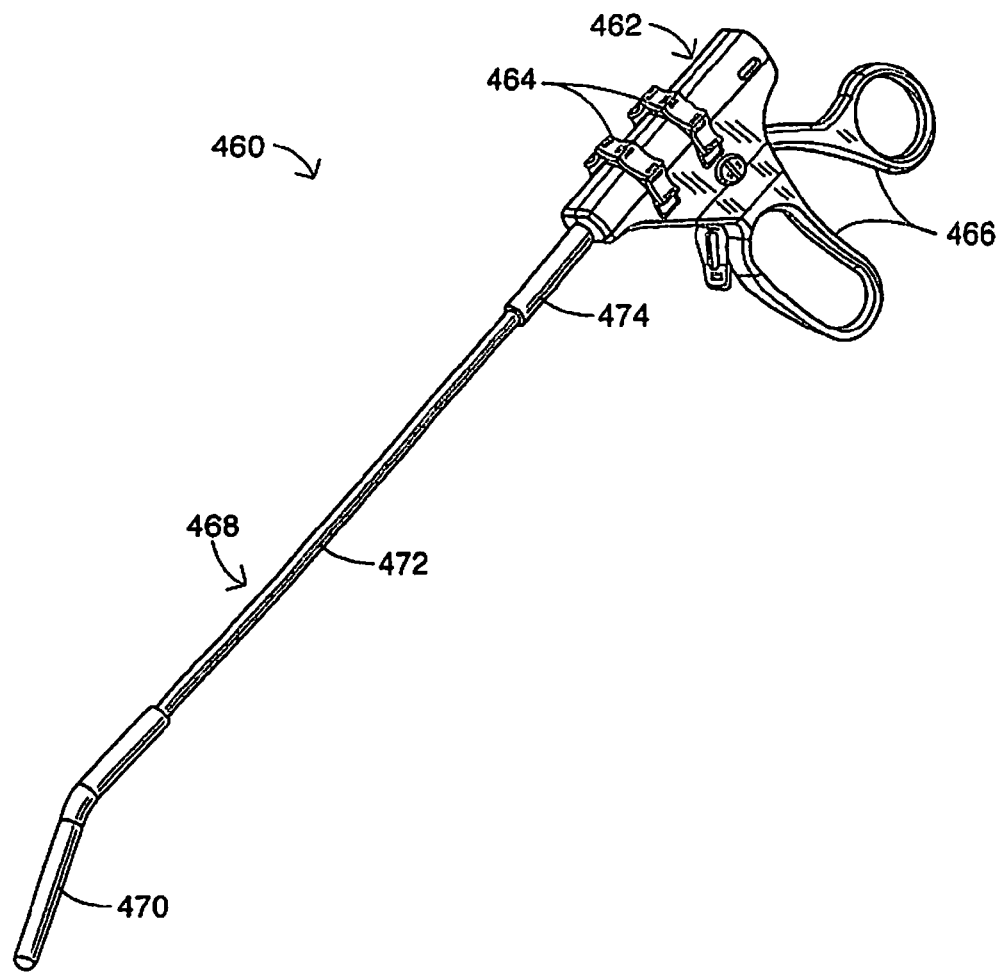
FIG. 53 is a schematic perspective view of a laparoscopic instrument for use with a surgical port assembly in accordance with the present invention.

The present invention can accommodate special hand instruments where the portion of the instrument shaft traversing the port assembly has a smaller diameter than the distal and/or proximal portion. As illustrated in FIG. 53, a laparoscopic instrument 460 includes a handle 462 with actuators or controls 464 and 466 and an elongate shaft 468. Shaft 468 includes an enlarged distal end portion 470 incorporating operative components (not shown), a thin middle section 472 and an enlarged proximal portion 474 connected to handle 462. Such a terminally enlarged instrument 460 can function with a detachable "octopus" with a special "C-shaped" channel. The instrument shaft 468 is sealed between the "C" and the internal wall of the funnel. The smaller diameter cross-section of middle section 472 allows one to maximize the range of motion that is limited by the port's internal diameter. Such an instrument 460 can serve to free up as much space in the restricted area as possible. The longitudinal cross-section of the instrument shaft 468 has an hour-glass (thin waist) configuration. A seal is established by the instrument seal(s)—one or several—which are located inside the cannula and hug the instrument tightly. Since the seals are very flexible, these would not restrict (seals will be deflected) the movements of the larger diameter sections (distal and proximal), but will not allow for gaps between the seals and the central or middle section 472 of the instrument shaft 468.

Figure 54:
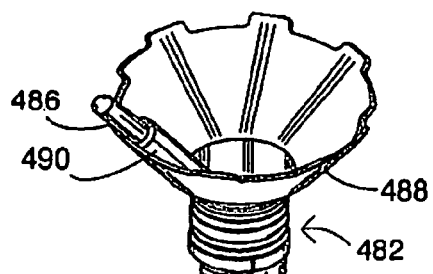
FIG. 54 is a schematic perspective view of a surgical port assembly with an integrated endoscope shaft or arm, in accordance with the present invention.
Figure 55:
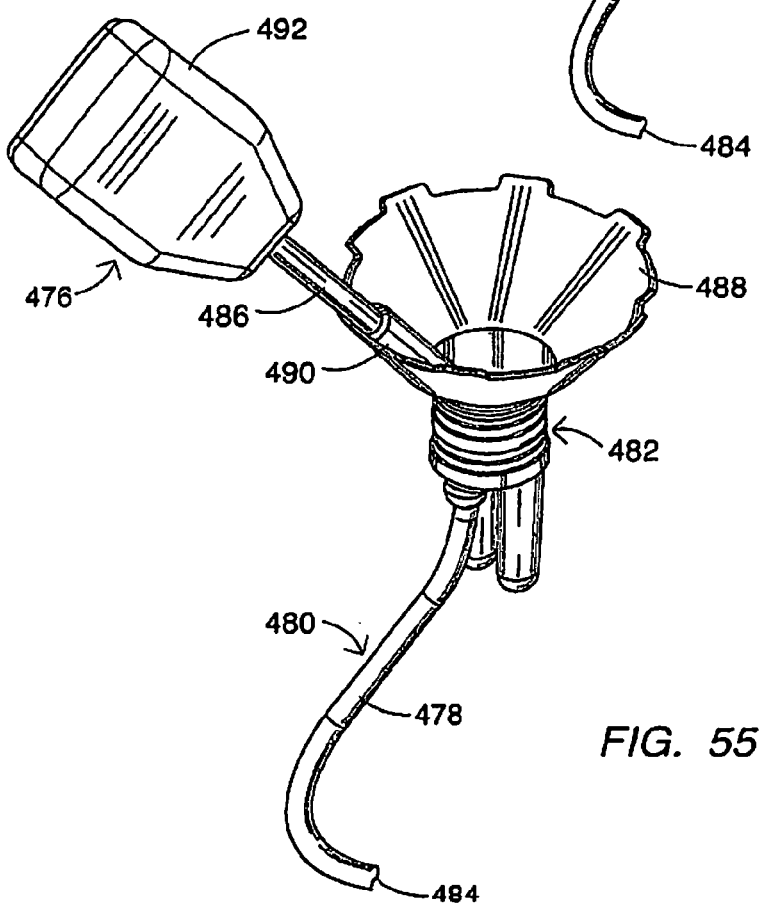
FIG. 55 is a schematic perspective view, similar to FIG. 54 but on a larger scale, showing a functional housing component on a proximal end of the endoscope shaft or arm of FIG. 54.
Figure 56:
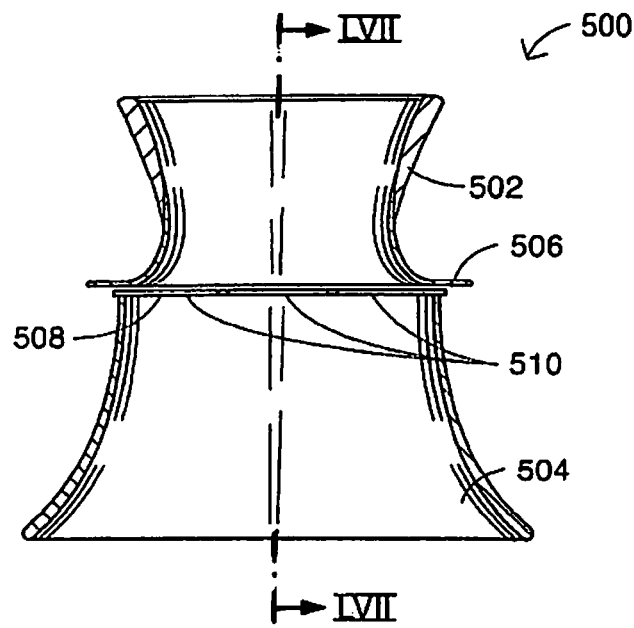
FIG. 56 is a schematic cross-sectional view of a thoracic surgical port in accordance with the present invention, taken along a wide dimension of the port, line LVI-LVI in FIG. 57.
Figure 57:
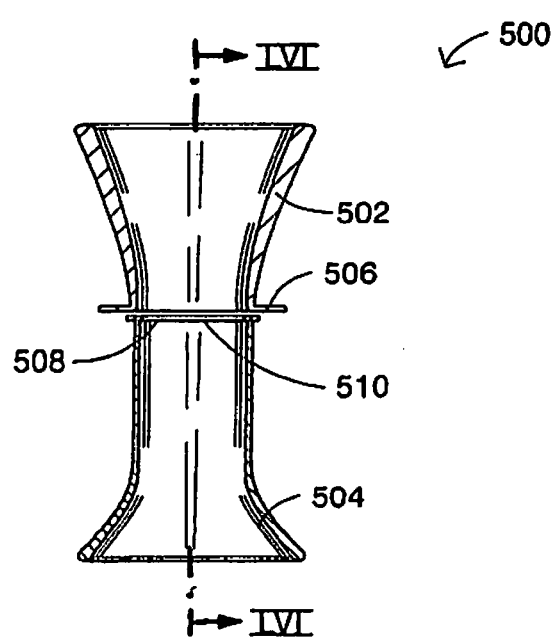
FIG. 57 a schematic cross-sectional view of a thoracic surgical port, taken along a narrow dimension of the port, line LVII-LVII in FIG. 58.
Figure 58:
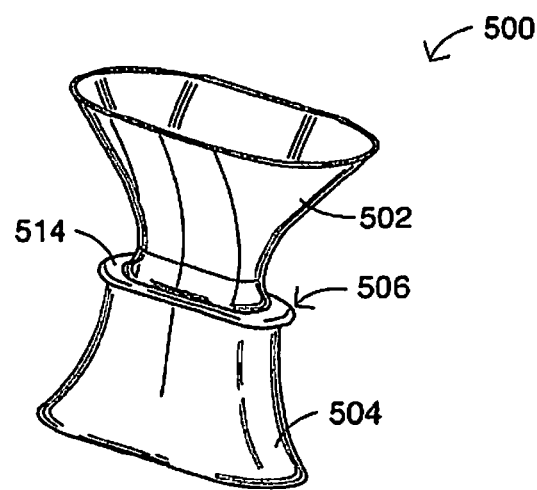
FIG. 58 is a schematic perspective view of the thoracic surgical port of FIGS. 56 and 57.

A surgical port assembly as described herein may be provided with a built-in or integrated endoscope 476, as depicted in FIGS. 54 and 55. A distal portion 478 of a scope arm 480 extending from an underside of a port assembly body member 482 is flexible and incorporates digital chip technology such as a charge-coupled device (not shown) at a distal end 484. In this design, only a small electrical cable need pass through the body member 482 of the surgical port assembly at the patient interface or skin surface, thereby reducing the scope's impact on the "effective" cross-section of the port and improving on the degree of motion. The built-in camera is maneuverable via cables (not shown) in the bendable shaft or arm 480. The cables may extend through the port's body member 482 to the proximal side thereof. Alternatively, orientation control may be effectuated wirelessly. In the latter case, a wireless receiver (not shown) may be integrated into the port body member 482 or the distal end portion 478 of scope arm or shaft 480. Motors (not shown) may be provided in scope arm 480 for bending distal end portion 478 in response to incoming wireless control signals.

As shown in FIGS. 54 and 55, scope arm or shaft 480 has a proximal end portion 486 that extends along a funnel-shaped portion 488 of body member 482 and is permanently or removably connected thereto. Specifically, proximal portion 486 passes through a sleeve 490 attached to funnel-shaped body portion 488. Alternatively, proximal shaft portion 486 may be partially or completely embedded in the wall of funnel-shaped body portion 488. Proximal shaft portion 486 is connected or connectable to an endoscope functional module 492 that may carry bending actuators or control knobs (not illustrated), a light source (not illustrated), electrical cables (not illustrated) for connecting to a video monitor, etc.

An integrated scope as shown in FIGS. 54 and 55 provides the required image using as little space as possible in the space-restricted area, that is, at the patient interface or skin surface. It is to be noted that rigid laparoscopes with all their straight proximal shafts substantial occupy space above the cannula holder or port assembly and thus interfere with the manipulation of "working" instruments. Existing flexible endoscopes do not provide sufficient visualization and are too fragile and too expensive. The design described above with respect to FIGS. 54 and 55 overcome these drawback.

As depicted in FIGS. 56-59, a thoracic surgical port 500 comprises a downwardly tapering, substantially flexible, upper or proximal part 502 and an upwardly tapering, substantially flexible lower or distal part 504. During use, upper part 502 is located subcutaneously, while lower part 504 extends in between the ribs of a patient into a pleural space. A substantially rigid ring-like structure 506 is located, during use of surgical port 500, on top of the patient's ribs (not shown). Ring structure 506 surrounds an interface or junction between upper part 502 and lower part 504. Upper part 502 is smaller than lower part 504. This allows one to make a smaller skin incision. Lower part 504 is larger and is accommodated in a slightly larger muscle-splitting incision (not shown) between ribs. A flexible membrane 508 is located inside the port at the level of ring structure 506.

Membrane 508 must be located in the proximity of the ribs—the restriction zone—in order to maximize the range of instrument freedom. Membrane 508 carries a variety of openings 510 for passage of the instruments (not shown). Membrane 508 and multiple openings 510 are needed (instead of one big opening) to provide the instruments with individual pivot points and individual compartments. This configuration improves surgeon ergonomics and minimizes the interference of instruments with each other. Rigid ring structure 506, sitting atop the ribs, provides stability of the port 500. Ring structure 506 does not slide into the chest and provides pivot points for the instruments. Ring structure 506 sits in a soft tissue pocket created by a surgeon with gentle finger dissection just above the patient's ribs. Also, in combination with a smaller skin incision, ring structure 506 eliminates the need for fixing the port 500 to the patient's chest. Port 500 is mobile but stable in the deployed location.

Ring structure 506 is a part of the entire thoracic port unit 500 and does not become detached from the rest of the unit when the unit is inserted in place. Ring structure 506 can be attached to upper part 502 and/or lower part 504 or to neither of those parts (attached instead to horizontal membrane 508), depending on manufacturing needs.

Upper part 502 and lower part 504 can have different durometer values. Upper and lower parts 502 and 504 can have the same flexibility, a similar flexibility, or a substantially different flexibility depending on the needs of the operator and the procedure. Upper and lower parts 502 and 504 can be permanently glued to one another during manufacture or could be manufactured (molded) as a single integral unit. Upper and lower parts 502 and 504 can be slidably attached to each other. For example, (1) lower part 504 may slide into upper part 502, which carries the rigid ring 506, (2) upper part 502 may slide into lower part 504, which carries the rigid ring 506, (3) upper and lower parts 502 and 504 may slide into a horizontal plate (a rigid membrane 508) that has openings 510 for the instruments and is surrounded by the rigid ring 506.

In any event, the rigid ring structure 506 sits on top of the patient's ribs. There is no need to fix the port 500 to the surrounding tissues, either with sutures of some other connectors. The port assembly 500 will stay in place.

Figure 59:
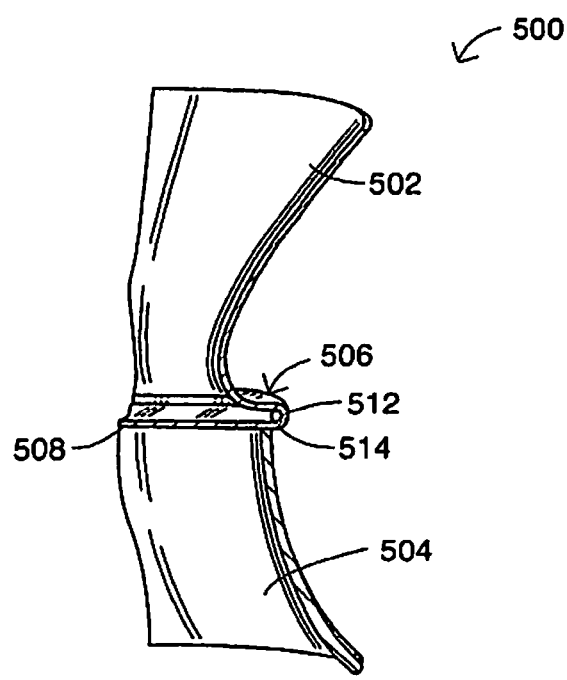
FIG. 59 is a broken-away schematic perspective view, on a larger scale, of the thoracic surgical port of FIGS. 56-58.

As depicted in FIG. 59, a rigid ring 512 seated inside a hollow flange 514 may form ring structure 506. Flange 514 is continuous with upper part 502 and membrane 508.

Turning now to FIGS. 60-73A, the surgical port assemblies disclosed therein are designed for minimally invasive surgery and are configured for insertion through a single opening in the patient, e.g. through the umbilicus, or placement adjacent such incision to provide access for surgical instrumentation through the incision. The port assemblies provide for freedom of movement of the instruments inserted through the port to facilitate the minimally invasive surgical procedure conducted in a limited space in the patient. Such minimally invasive procedures include, for example, laparascopic and thorascopic procedures, as well as other endoscopic procedures.

Turning first to FIGS. 60-63, an embodiment of yet another port assembly of the present invention is disclosed. The port assembly 1010 includes a substantially cylindrical lower or distal body portion 1012, an outwardly flared upper or proximal portion 1030 having a substantially conical or funnel shape body, and a cannula unit 1040 comprising a flexible membrane 1041 and cannula sleeves or trocars 1040a, 1040b and 1040c extending distally from the membrane forming the "legs" or "fingers" of the unit 1040. The cannulas 1040a-1040c have lumens formed therein (see e.g. 1044a of FIG. 60A) configured to receive surgical instruments as described below. An obturator 1060, described in more detail below, is removably positioned within the port assembly during insertion to facilitate placement of the port assembly 1010.

More specifically, body portion 1012 of port assembly 1010 comprises an annular body 1014, a part of which is preferably positioned within an opening in a patient such as an incision in the umbilicus. Body 1014 preferably has a series of annular ribs 1016 on the outer surface to enhance the frictional engagement of the body 1014 with the tissue T adjacent the incision (see e.g. FIG. 65) to enhance the seating and reduce the slippage of the port assembly 1010 during use. The ribs 1016 can be, for example, in the form of a helical thread to provide frictional engagement (and to provide for rotational insertion of the port assembly) or can be in the form of raised projections or roughened surfaces. The body 1014 is preferably substantially rigid and preferably composed of polycarbonate, although other materials can be utilized. It is also contemplated that in alternate embodiments the body portion, or portions thereof, can be composed of more flexible material which could stretch during manipulation of the instruments within the cannulas, while still providing sufficient support for the assembly. For example, portions of the body 1014 can be composed of different materials or different hardness of the same material.

Supported on the body 1014 is flexible membrane 1041 which serves as a cannula carrier or support. A swaged attachment ring 1017 secures (clamps) the cannula carrier 1041 to a distal portion of the outer surface of body 1014, although the carrier can be attached by other methods such as gluing. The carrier 1041 is preferably in the form of a transversely extending flexible membrane, preferably composed of an elastomeric material such as silicone, polyisoprene or thermoplastic elastomers, but other materials can be utilized. The material is preferably flexible and stretchable to provide increased range of motion of the cannulas (legs/fingers) 1040a-1040c as the cannula is pivoted (with respect to an axis parallel to a longitudinal axis of the body 1014) and swiveled (about the longitudinal axis) by manipulation of the surgical instrument inserted therethrough. That is, the increased range of motion of the cannulas 1040a-1040c translates into increased range of motion of the instruments inserted therethrough to facilitate the surgical procedure as well as allow for additional procedures to be performed which might otherwise not be achievable in a limited space provided in the patient if instrument mobility is limited.

By being composed of flexible material, the cannulas are flexible in their region extending from the membrane. It is also contemplated that portions of the cannulas and/or portions of the cannula carrier are more rigid, provided they are at least flexible (or movable) in a region of attachment to the carrier, enabling the cannulas (legs/fingers) to be temporarily bent to various angles as well as twisted in rotational movements in response to forces exerted by manipulation of the surgical instrument shafts during a surgical procedure. Thus, the flexibility enables a pivoting and/or a swiveling of the surgical instruments (or an endoscope) inserted through the cannulas. It should be appreciated that the transversely extending cannula carrier, although preferably flexible in its entirety, could alternatively be configured that some sections are flexible, e.g. those sections adjacent the cannula interface, and some sections more rigid or even substantially rigid. Different rigidity can be achieved for example by using different hardness or thickness of the same material or by utilizing different material. In the illustrated embodiment, the port body and flexible membrane are composed at least in part of different materials, with the membrane having more flexible portions and the port body having more rigid portions.

Preferably the carrier 1041 and cannulas 1040-1040c extending therefrom are composed of (e.g. molded from) the same material, although it is also contemplated that alternatively the cannulas be composed of a different material and attached to the carrier (membrane) 1041 by gluing, for example, or other methods.

It is also contemplated that the opposing surfaces, i.e., the interface between the cannulas 1040a-1040c and the carrier 1041, can be made of a variety of materials and shapes (congruent or not congruent) which would facilitate a substantial range of motion of one part in relation to the other parts. At the same time, by creating some additional friction between the opposing surfaces, e.g. by choosing less lubricious material or irregular surfaces, the movement of the parts becomes more controlled by the surgeon, creating a somewhat micro-ratchet effect in all directions.

Attached to the cannulas 1040a-1040c are distal cannula extensions 1049a-1049c. These cannula extensions 1049a-1049c are attached to the respective cannulas 1040a-1040c, respectively by a swaged ring 1051. The stiffening tubes 1080 (described below) positioned within the cannulas 1040a-1040c provide a base for the swaged ring 1051.

In the illustrated embodiment, the cannulas 1040a-1040c extend distally from the membrane 1041 such that a proximal opening (see e.g. 1040e, 1040f of FIG. 66) in the cannulas 1040a-1040c is adjacent a surface of the membrane 1041. As shown, cannulas 1040a-1040c, extend distally from the membrane 1041 beyond the distal end 1019 of the body portion 1014, and in the illustrated embodiment, the cannulas 1040b and 1040c do not extend proximally of the carrier 1041 or of the body 1014. However, in alternate embodiments, one or more of the cannulas can also extend proximally. Alternatively, cannulas can extend predominantly proximally or only proximally.

Cannulas 1040a-1040c may each have a stiffening tube 1080 (see FIG. 66) positioned in their respective lumen to provide increased strength and rigidity, reduce friction during instrument insertion and removal, and reduce the likelihood of inversion of the cannulas. The tubes 1080 can be made of a variety of materials, including for example polytetrafluorethylene. The tubes also, as noted above, provide a base for swaging of the cannula extension attachment ring 1051, as best shown in the exploded perspective view illustrated in FIG. 66A.

Figure 64:
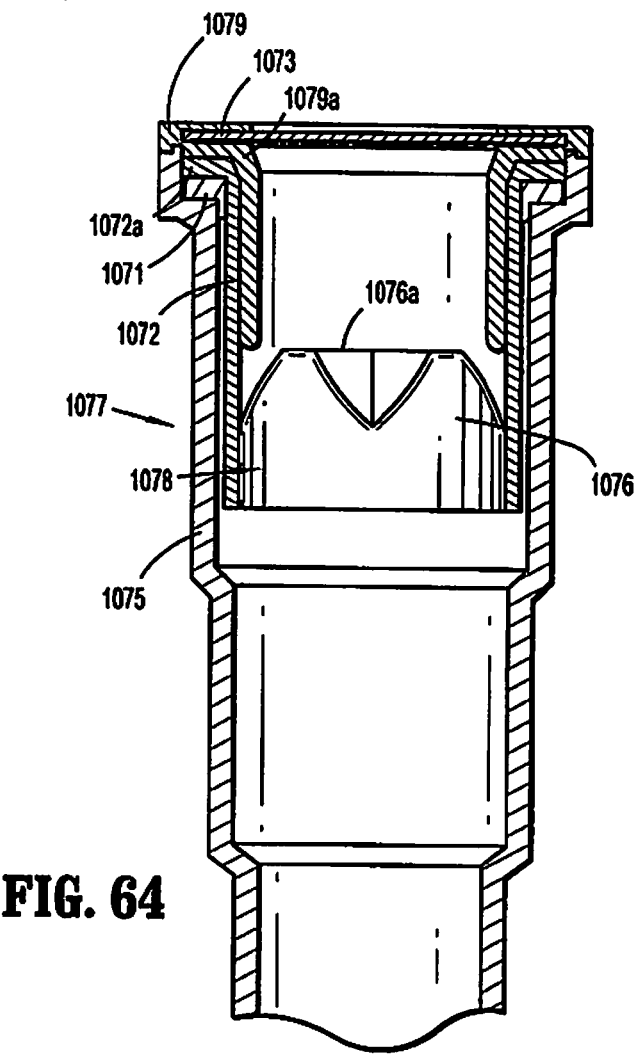
FIG. 64 is a cross-sectional view of a portion of the port assembly taken along line 64-64 of FIG. 60.

In a preferred embodiment, mounted within cannula 1040a is a dedicated tube 1075, extending proximally beyond the proximal rim 1052 of upper portion 1030 and preferably designed for the introduction of insufflation gas. For this purpose, tube 1075 has a valve assembly 1078, including a quad-seal 1076 at a lower portion 1074 and a ring seal 1073 supported within cap 1079, as shown in FIG. 64. The quad seal 1076 is shown in the enlarged view of FIG. 64A and is formed of two crossed rectangular surfaces 1076a, 1076b. These rectangular surfaces each have a slit 1076c intersecting at center 1076d. The seal functions as a valve to prevent loss of pneumoperitoneum when instruments are not inserted through the port. Seal 1073, in the form of a flexible membrane with a central hole 1072, is secured to shoulder 1079a of cap 1079 which is secured to sleeve 1072 and is seated atop shoulder 1072a of sleeve 1072. Shoulder 1072a of sleeve 1072 is seated atop and secured to support ring 1071. Seal 1073 functions to prevent loss of pneumoperitoneum when an instrument is inserted within the cannula.

An insufflation tube 1074, having a luer lock communicates with the lumen of tube 1075. The tube (cannula) 1075 is preferably permanently attached as shown, but alternatively can be removably connected e.g. releasably frictionally fit, within one of the distally extending cannulas. Tube 1075 can also be used to receive a scope or other imaging device or other surgical instruments, with the seals maintaining pneumoperitoneum during instrument insertion and removal.

Figure 64A:
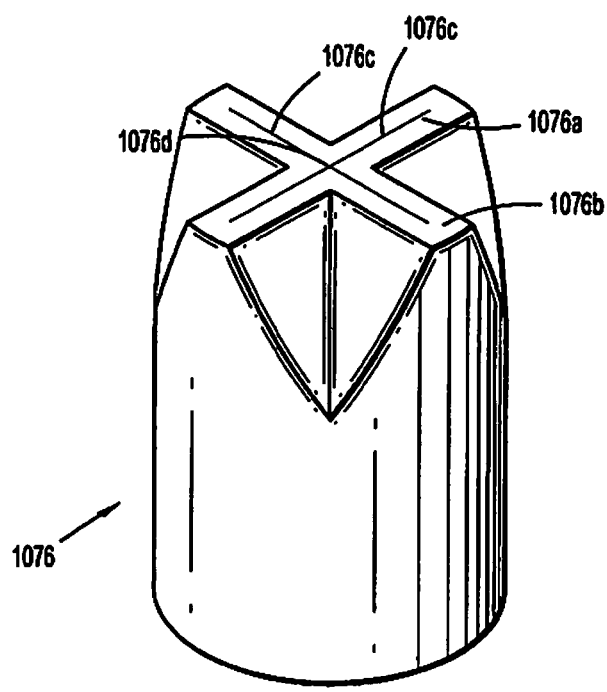
FIG. 64A is an enlarged view of the valve of FIG. 64.

The cannula units 1040a-1040c preferably have a seal (valve) at their distal end for maintaining pneumoperitoneum when a surgical instrument shaft is inserted therethrough and a seal at a more proximal region for maintaining pneumoperitoneum when there is no instrument inserted. In a preferred embodiment, a quad valve similar to valve 1076 of FIG. 64A is positioned within each of the distal cannula extensions 1049a, 1049b and 1049c and a seal 1042a, 1042b and 1042c, in the form similar to seal 1073, i.e. with a flexible membrane and a stretchable central opening, is positioned within a proximal portion of the respective cannulas 1040a-1040c. For clarity, the distal valves are not shown in the cross-section of FIG. 66. The valves are preferably molded with cannula extensions 1049a-1049c and seals 1042a-1042c seals are preferably molded with the cannulas 1040a-1040c (and cannula carrier 1041). Other types of seals are also contemplated, such as a tricuspid seal or other ring or bead seals. Additionally, although preferably molded with the unit, the seals can be separate structure attached to the respective cannula/cannula extensions.

Although three cannulas are shown, it is also contemplated that only two cannulas could be provided. It is also contemplated that more than three cannulas could be provided. One or more of the cannulas could extend proximally from the carrier 41.

In one embodiment, all three cannulas 1040-1040c are of substantially the same diameter. In alternate embodiments, such as the illustrated embodiment where cannula 1040b (and its cannula extension 1049b) has a larger diameter (and a larger lumen) than the diameter (and lumen) of cannulas 1040a, 1040c, (and their cannula extensions 1049a, 1049c), the cannulas/cannula extensions can be of different diameters. By way of example, one cannula/cannula extension could be 12 mm in diameter and the other two cannulas/cannula extensions could be 5 mm in diameter to accommodate instruments of different sizes.

One or more of the cannulas can have a wider and deeper entrance space or antechamber to allow an increased range of instrument motion and an easier crossing of the instrument shafts. Cannulas 1040a-1040c are shown as substantially circumferentially equidistantly spaced, but other spacings are also contemplated.

In one embodiment, the cannula unit (module) 1040 (see FIG. 60) may be removably attached to a port assembly body member to enable switching of one cannula module with another. Thus, for example an "octopus" module with two cannulas (e.g. one for a scope and one for another instrument) could replace a unit with three cannulas. When a cannula unit is removed, the opening in the body member could be used for tissue evacuation or other procedure that requires a large access opening. Pneumoperitoneum can be quickly re-established upon connection of a new cannula module by use of temporary port plug fitting into the opening of the body member (e.g., into a cylindrical portion) during an exchange of the cannula units.

Referring back to FIGS. 60, 60A and 65, upper or proximal portion 1030 of port assembly 1010 has a body 1050 having a circular rim 1052 with a plurality of suture anchors 1054 (only a few of which are labeled for clarity). Suture anchors 1054 are illustratively in the form of upwardly inclined posts for receiving tie-down sutures (not shown) to anchor the trocar port assembly to a patient at an incision site (such as the umbilicus). Body 1050 is additionally provided along circular rim 1052 with a plurality of rectangular recesses 1055 between anchors 1054 for receiving projections or keys of obturator 1060 described below. Body 1050 is flared to create additional space for instrument insertion, with the transverse dimension of body 1050 being greater than a transverse dimension of body 1014 and a proximal region of body 1050 having a greater transverse dimension than a distal region.

Obturator 1060 comprises a rectangular shaped body member 1062 having engagement tabs 1064 in the form of generally rectangular keys or tabs projecting radially outwardly from body member 1062 and adapted to be seated in cooperating rectangular recesses 1055 of port assembly 1010. A curved gripping ridge 1066 projects upwardly from the body member 1062 to facilitate grasping of the obturator 1060 by the user. Elongate rigid members 1068 extend distally from the body member 1062 on a side opposite finger contact ridge 1066. Although two rigid members are shown, a different number can be provided.

In use, the obturator 1060 is mounted to the port assembly 1010 such that each of the rigid members 1068 extends at least partially into one of the cannulas to stiffen the cannula for insertion of the port assembly. The engagement tabs 1064 of the obturator can be placed on any of the opposing recesses of the port assembly to position and rest the obturator 1060 on port assembly 1010. After insertion of and placement of the port assembly, the obturator 1060 is removed from the port assembly 1010 for subsequent insertion of surgical instruments to perform the surgical procedure. It is also envisioned that the rigid members of the obturator can be elongated to extend beyond the distal end of the cannulas and have a blunt or penetrating tip for penetrating through a skin surface and underlying tissue of a patient for certain surgical applications of the port assembly. It is also contemplated that the recesses of the port can be smaller and dimensioned to mate with the tabs so the obturator can be interlocked with the port assembly 1010. The obturator can also used with other port assemblies.

Figure 65:
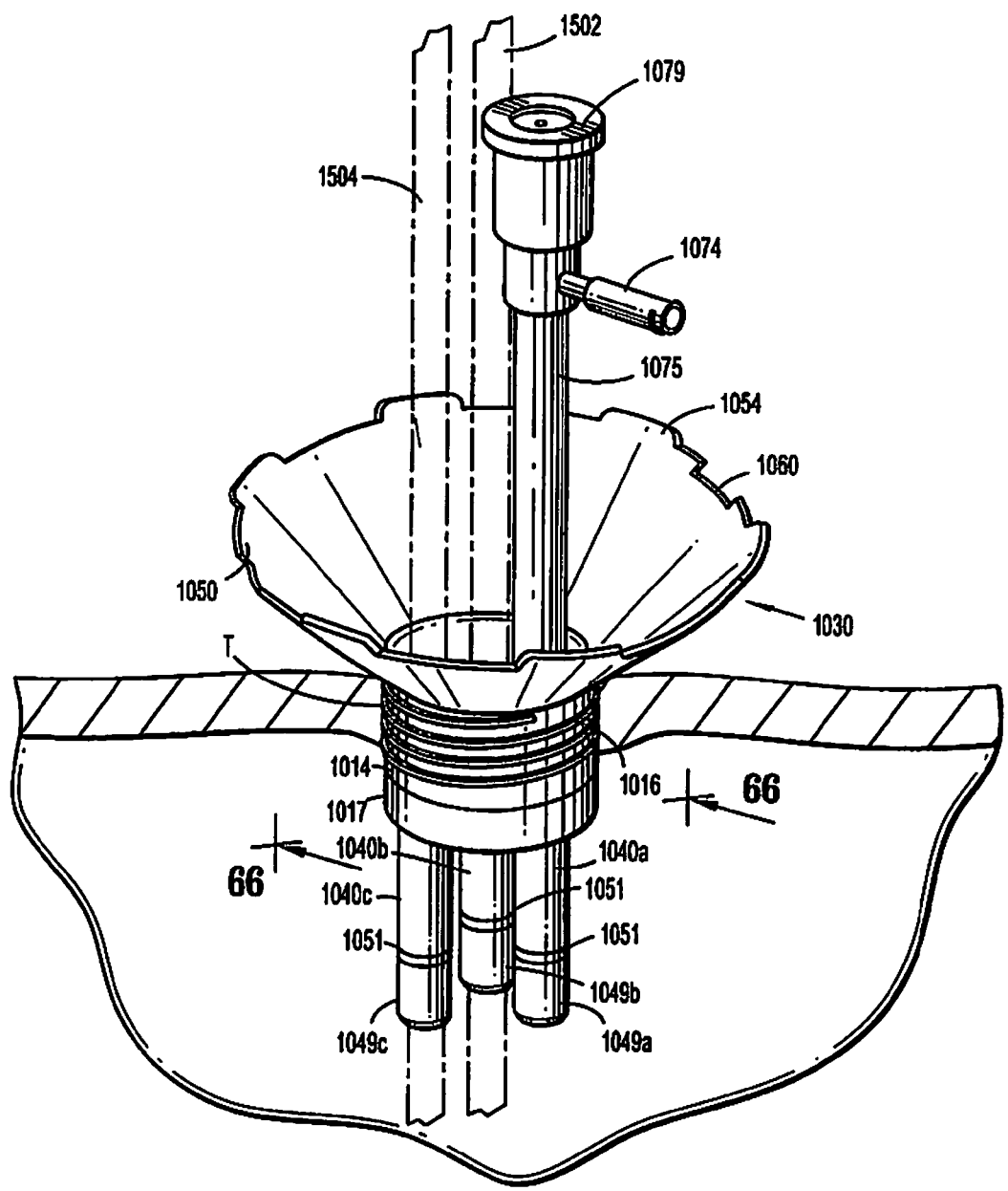
FIG. 65 is a perspective view of the port assembly of FIG. 60 showing in phantom a surgical instrument inserted through two of the cannula members.
Figure 66:
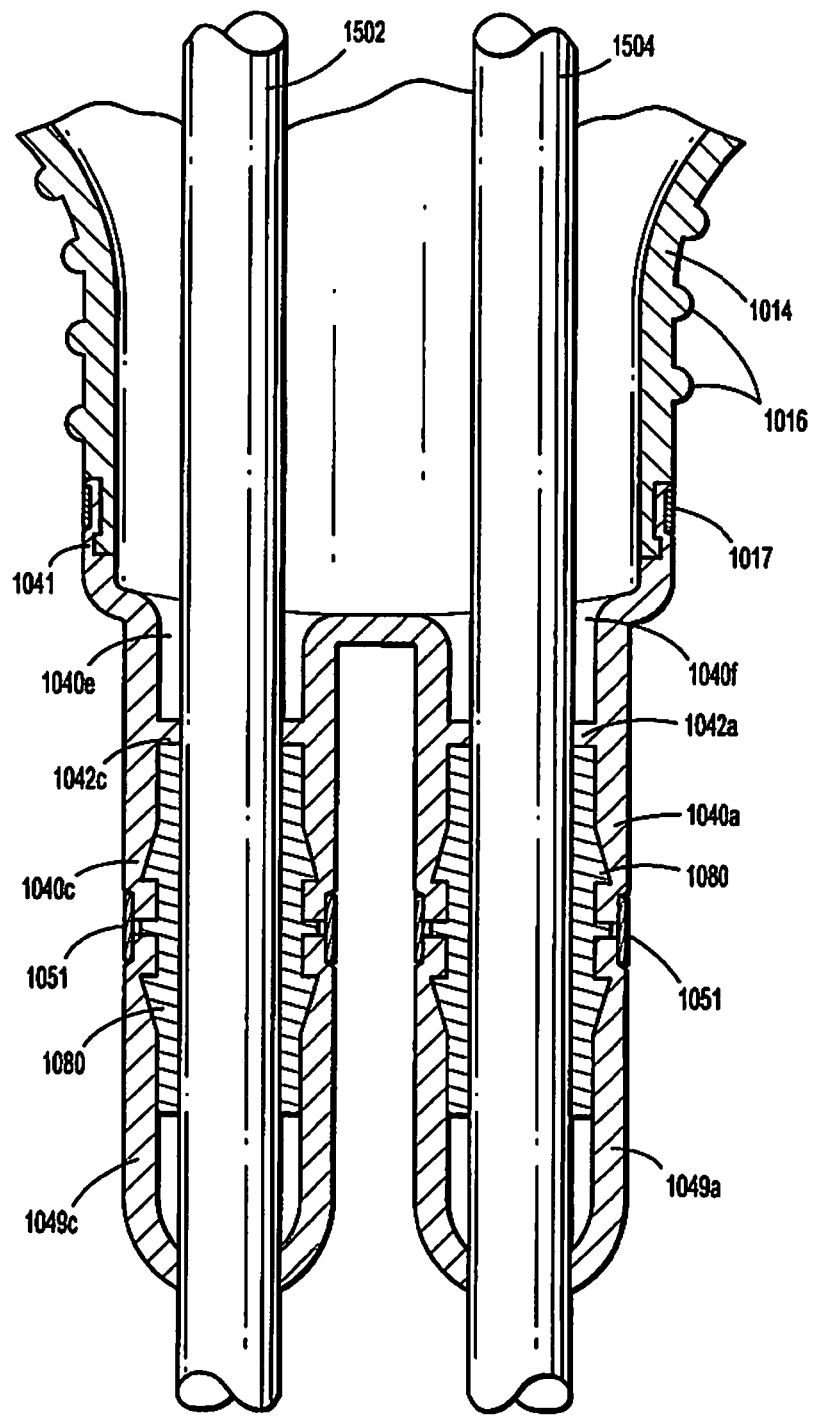
FIG. 66 is an enlarged cross-sectional view of a portion of the port assembly of FIG. 60 showing two instruments extending distally of the cannula members.
Figure 67:
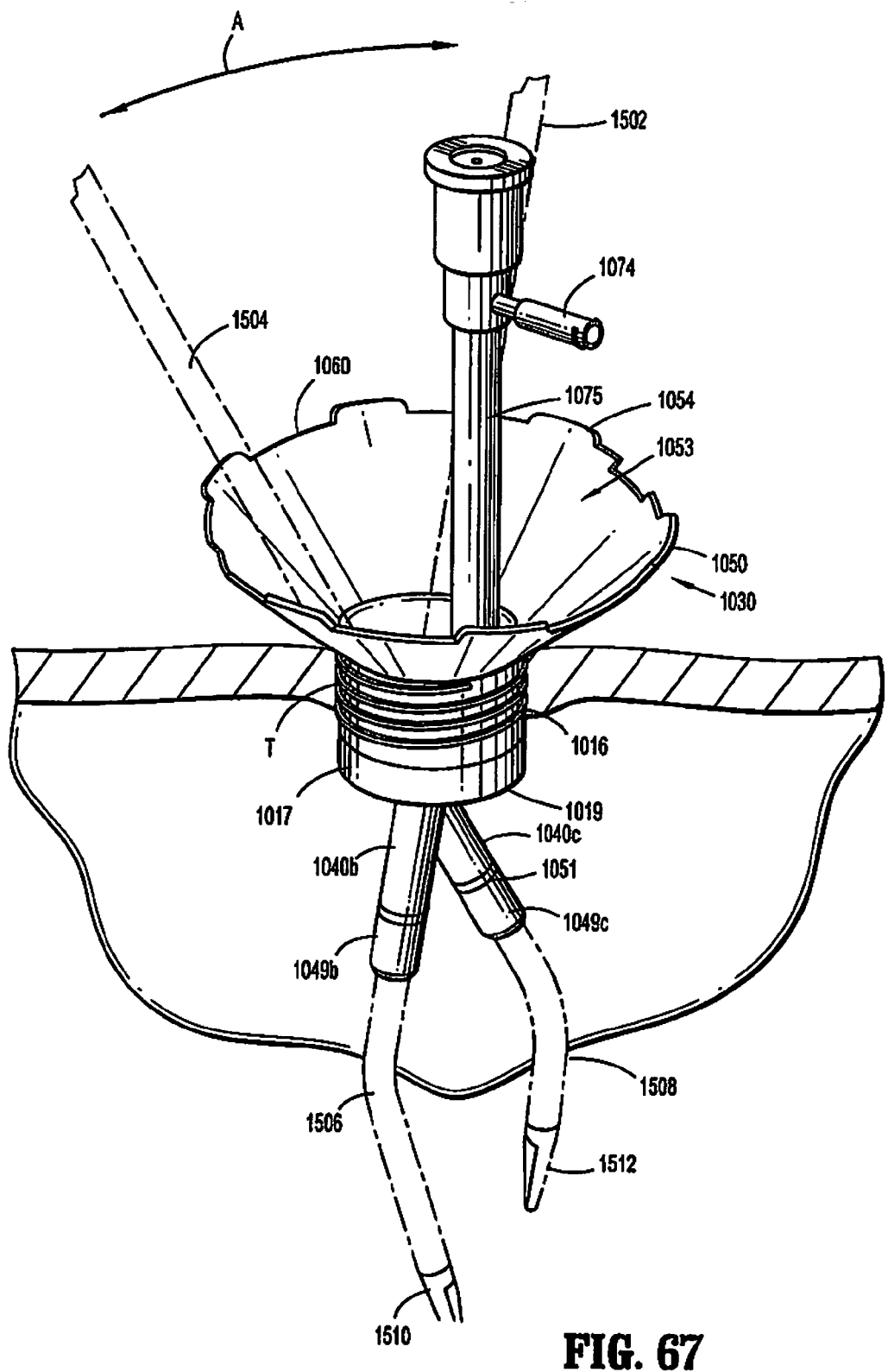
FIG. 67 is a perspective view similar to FIG. 66 showing movement of the instruments to a crossed configuration and further showing the operative tips pointing toward the target site.

FIGS. 65 and 67 illustrate use of the port assembly 1010. The port is placed in an incision in tissue T to provide access to a body cavity, with ridges 1016 frictionally engaging the tissue edges. As shown, a first instrument 1502 is inserted through cannula 1040b and a second instrument 1504 is inserted through cannula 1040c. Generally, in a laparoscopic operation, one of the cannulas, e.g. cannula 1040a receives a laparoscope for visualization. For clarity, cannula 1040a and extension 1049a are removed from FIG. 67. (It should be noted that, also for clarity, although FIG. 66 is a partial cross-sectional view of FIG. 65 where the instruments 1502, 1504 are shown in phantom, in FIG. 66, instruments 1502, 1504 are shown as solid tubular members, rather than in phantom or as cut-away views showing the interior of the instruments.)

The instruments 1502, 1504 are utilized in a crossed configuration as shown to increase the separation of the surgeon's hands. As the instrument 1502 and/or 1504 is moved to change its orientation, as shown by the double arrow A, it forces the respective cannula and cannula extensions to this new orientation (position). The cannulas 1040a-1040c can accommodate various types of hand instruments. The instruments 1502, 1504 shown in FIG. 67 have a curved shaft 1506, 1508 so that the distal tips (instrument jaws 1510, 1512) can point toward each other and/or the target site for performance of the surgical procedure. The jaws as shown have at least one jaw movable with respect to the other jaw. Other instruments that can be used also include, for example, those described in commonly assigned copending application Ser. No. 61/191,733, entitled "LAPAROSCOPIC INSTRUMENT AND RELATED SURGICAL METHOD", filed on Sep. 11, 2008, which is now co-pending U.S. patent application Ser. No. 12/550,617 filed on Aug. 31, 2009. Both of the foregoing applications are hereby incorporated by reference herein. The cannulas can also accommodate other instrument shafts, including those that are fully flexible as well as instrument shafts that are straight or have preformed rigid shapes, including C-shaped and S-shaped portions.

Figure 68:
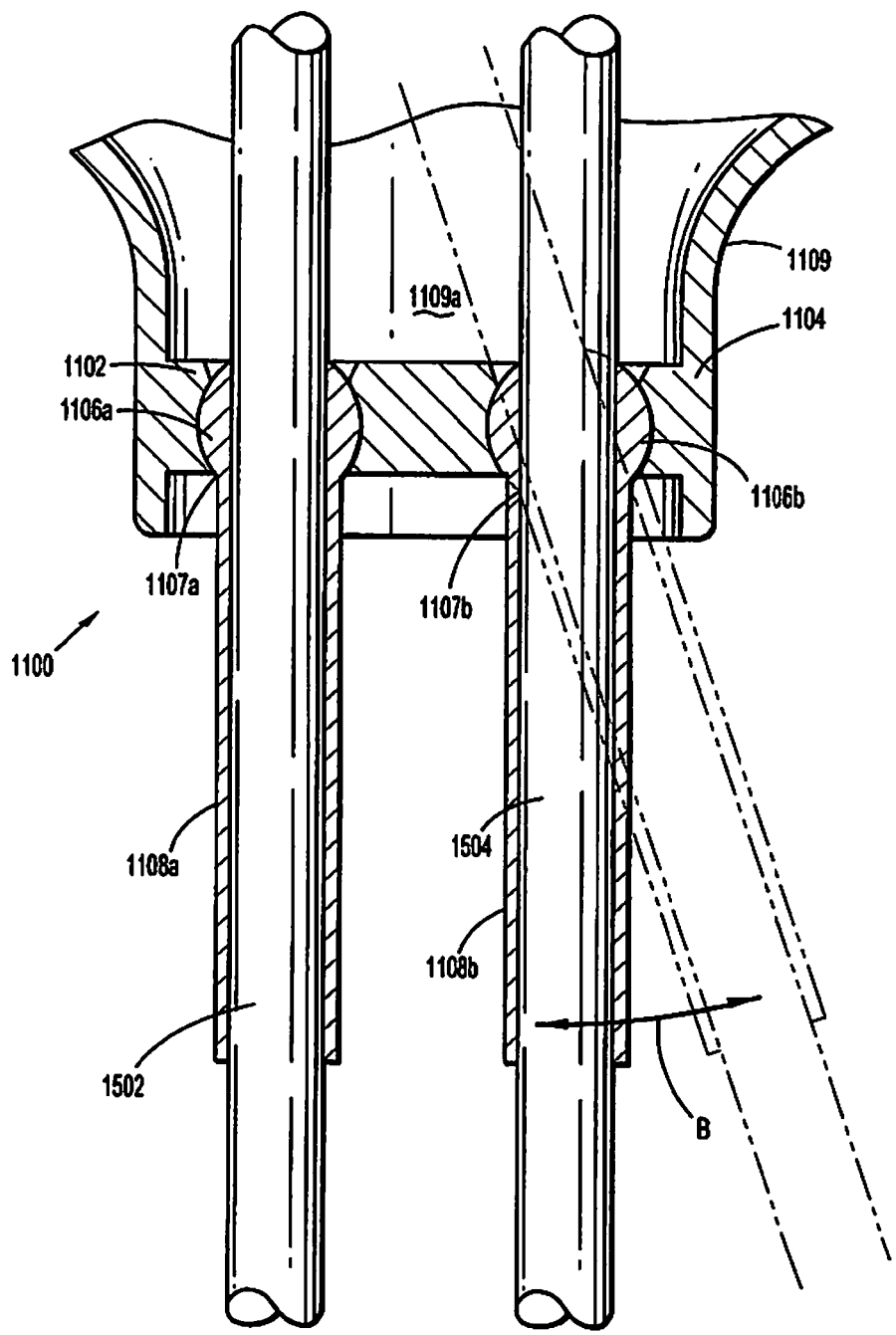
FIG. 68 is a cross-sectional view of an alternate embodiment of the port assembly of the present invention and showing an instrument inserted through the cannulas.
Figure 69:
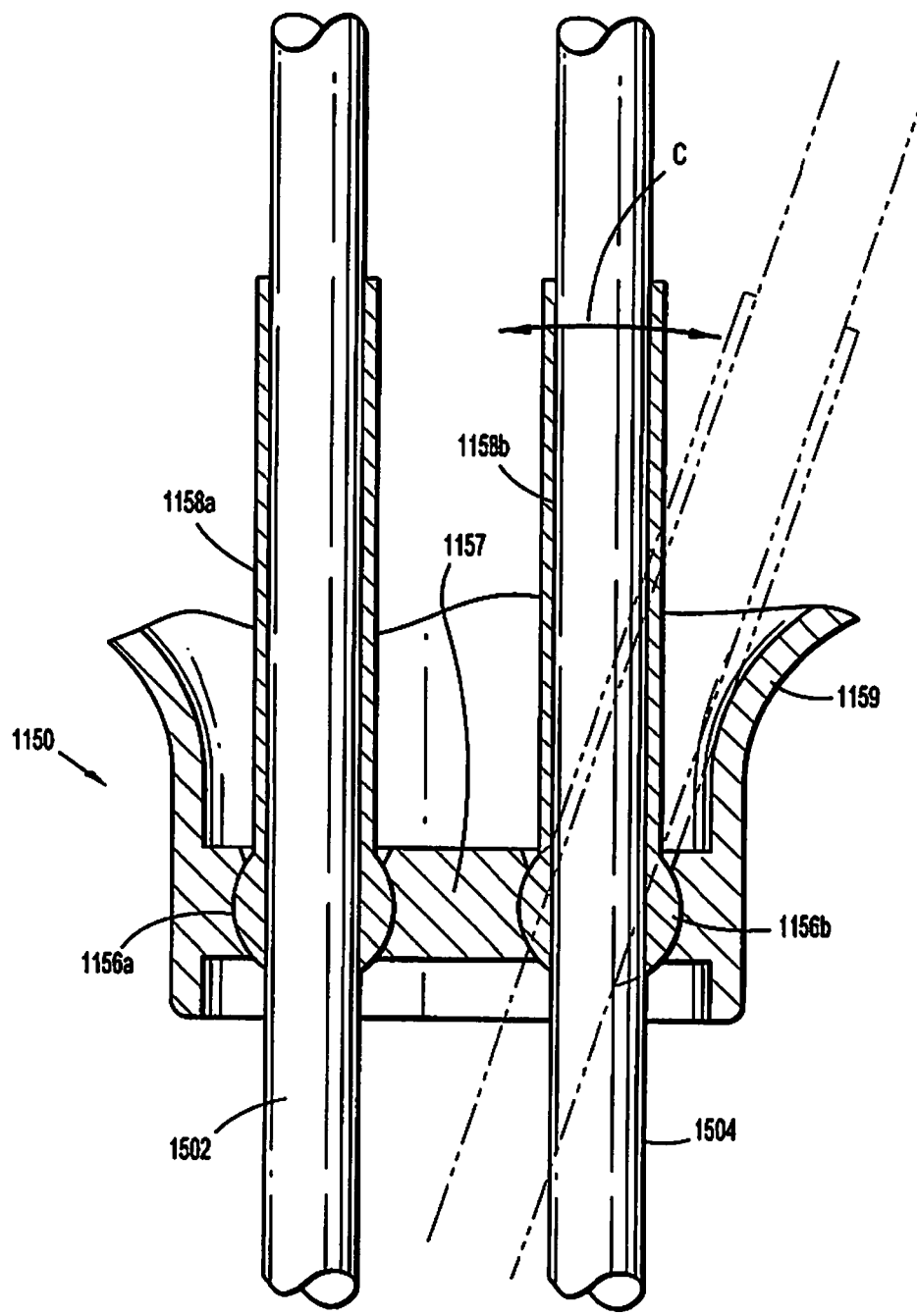
FIG. 69 is a cross-sectional view of another alternate embodiment of the port assembly of the present invention and showing an instrument inserted through the cannulas.
Figure 70:
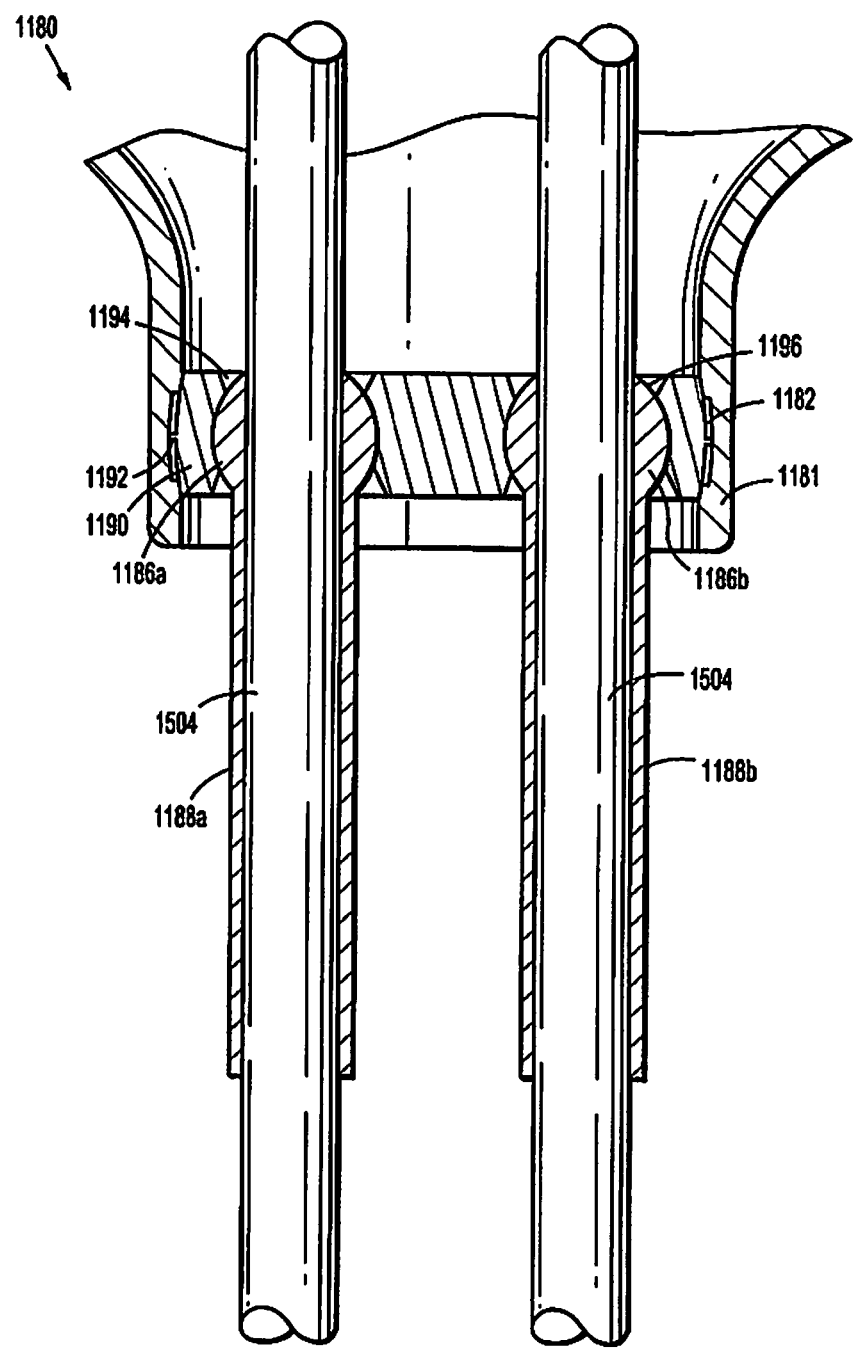
FIG. 70 is a cross-sectional view of yet another alternate embodiment of the port assembly of the present invention and showing an instrument inserted through the cannulas.

FIGS. 68-70 illustrate alternate embodiments of the port assembly having a ball joint to enable pivoting of the cannulas to provide for freedom of movement of the surgical instruments inserted therethrough. More specifically, in the embodiment of FIG. 68, the port assembly 1100 includes a support 1102, preferably in the form of a substantially rigid plate and preferably composed at least in part of metal, and preferably extending substantially transversely within the body member 1104. The support 1102 can be a separate component attached to the inner wall of the body member 1104 or integral therewith. Support 1102 has a plurality or recesses to receive pivoting ball portions 1106a and 1106b therein. Each of the ball portions 1106a, 1106b has an opening extending therethrough to receive a surgical instrument. Extending downwardly (distally) from each of the ball portions 1106a, 1106b is a respective cannula portion 1108a, 1108b, shown integrally formed with the ball portions 1106a, 1106b. Thus, the proximal opening in each cannula 1108a, 1108b is adjacent the bottom surface 1107a, 1107b of the respective ball portion 1106a, 1106b. The cannula and ball portion can be integrally formed or alternatively be separate attached components.

The ball joint provides for pivoting movement of the cannula which in turn enables pivoting movement of the instrument inserted therethrough. Consequently, when an instrument is inserted through the cannula, the user can maneuver the instrument to thereby pivot the cannula (see arrow B) to facilitate access to and performance of the surgical procedure.

Although two cannula members with ball joints are shown in FIG. 68 (as well as in the embodiments of FIGS. 69 and 70 discussed below), three or more cannula members with such joints, or only one cannula member with such joint, can be provided in these embodiments. Also, all of the cannulas can be pivotable via ball joints or one or more can be rigidly attached while the others are pivotable. Additionally, hinges or other connections to provide the movement of the ball and socket joints can be utilized.

Figure 60:
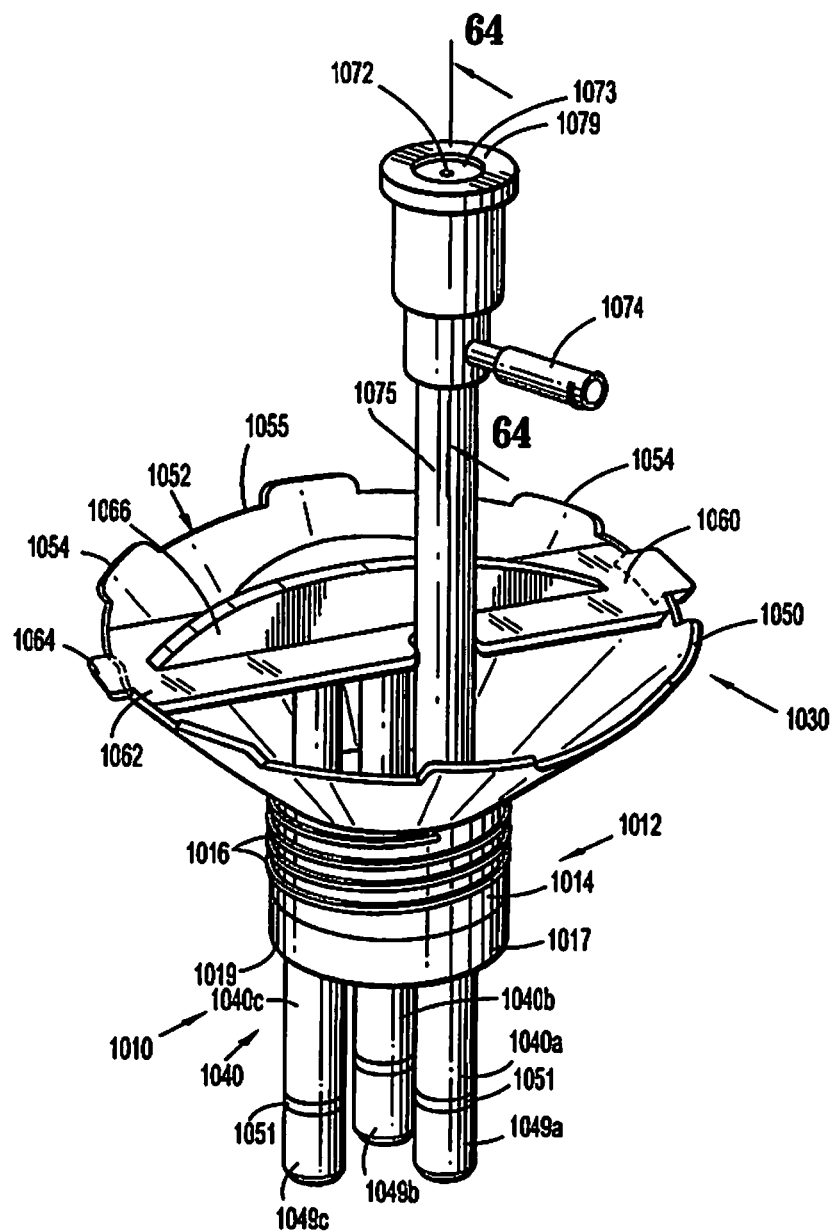
FIG. 60 is a perspective view of a first embodiment of the port assembly of the present invention shown with an obturator positioned therein to aid insertion.
Figure 60A:
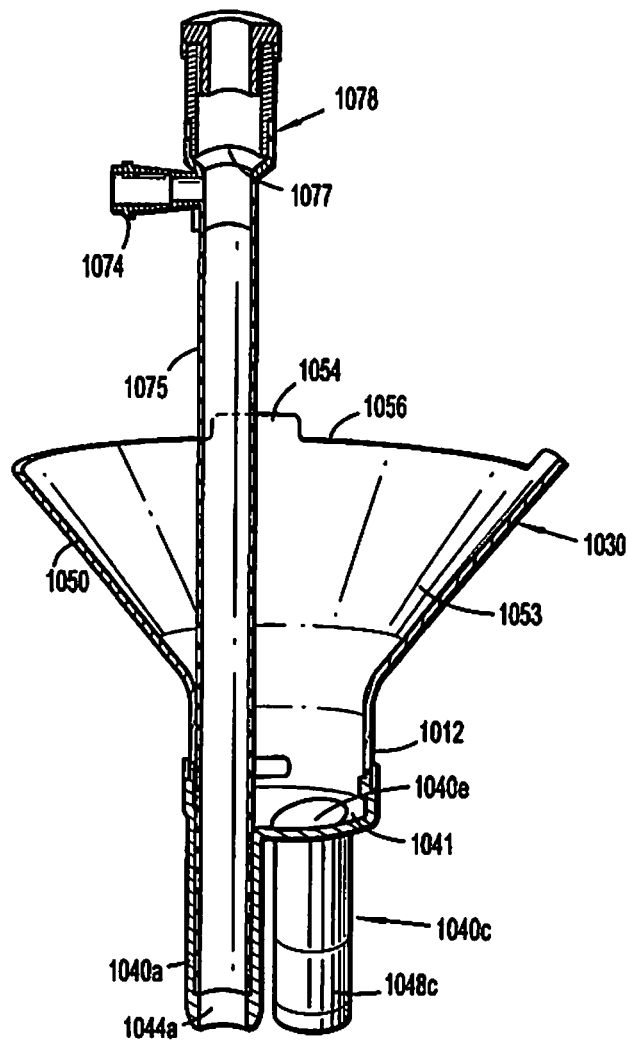
FIG. 60A is a perspective view, partially cut away, of the port assembly of FIG. 60 with the obturator removed.
Figure 61:
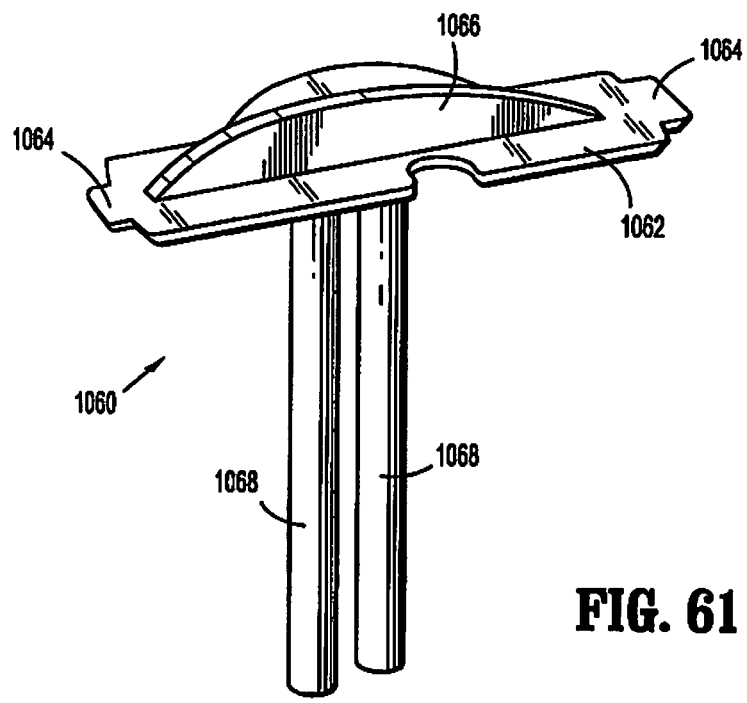
FIG. 61 is a perspective view of the obturator.
Figure 62:
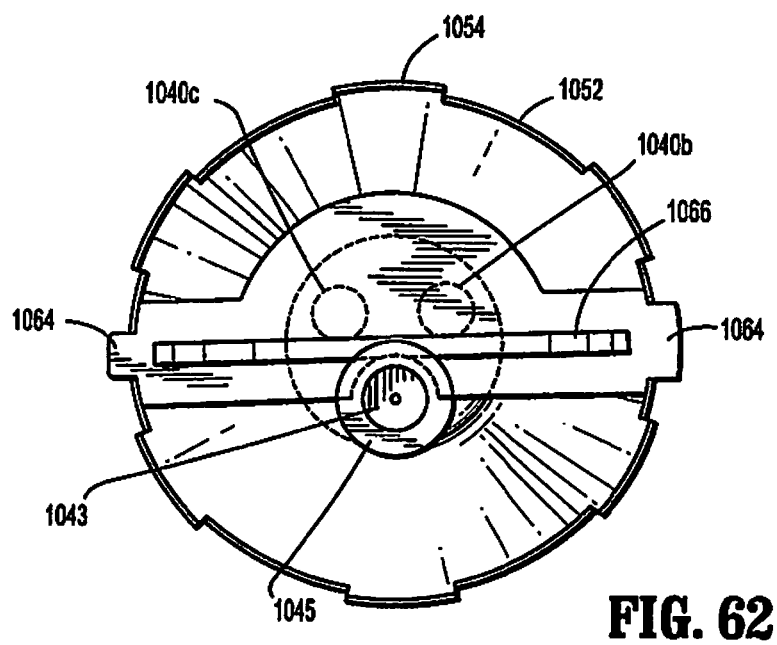
FIG. 62 is a top view of the port assembly and obturator of FIG. 60.
Figure 63:
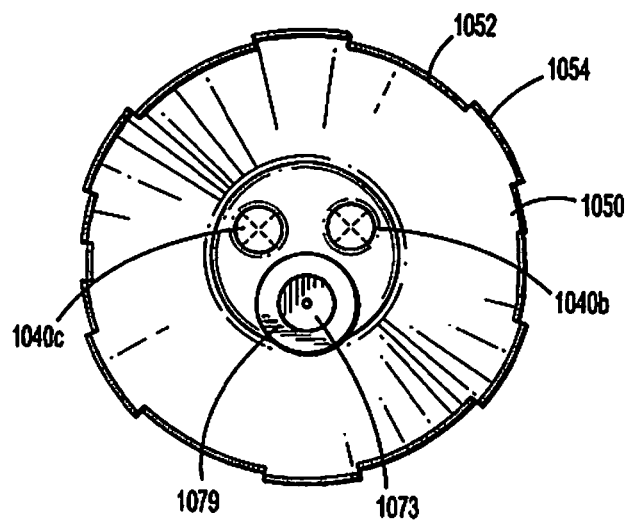
FIG. 63 is a top view of the port assembly with the obturator removed.

Body portion 1104 preferably flares outwardly at its proximal portion 1109, similar to the flare of the port assembly 1010 of FIG. 60, to provide a conical or funnel shape with space 1109a to increase the range of movement of the instruments. An instrument shaft 1502, 1504 is shown extending through the cannulas 1108a, 1108b, respectively, with a pivoting motion of instrument 1504 in one of the myriad directions shown in phantom.

In the alternative embodiment of FIG. 69, the cannula members 1158a, 1158b of port assembly 1150 extend upwardly (proximally) from ball portions 1156a, 1156b, rather than downwardly as in the embodiment of FIG. 68. Thus, a distal opening of the cannula members 1158a, 1158b is adjacent the proximal opening in the respective ball portion 1156a, 1156b. Ball portions 1156a, 1156b are seated within recesses in support 1157. This ball joint enables pivoting of the instruments 1502, 1504 as shown by the arrow C. In all other respects port assembly 1150 is the same as port assembly 1100 of FIG. 68, e.g. funnel shaped proximal portion 1159, substantially transverse support 1157, etc. and therefore for brevity is not further described herein.

Figure 70A:
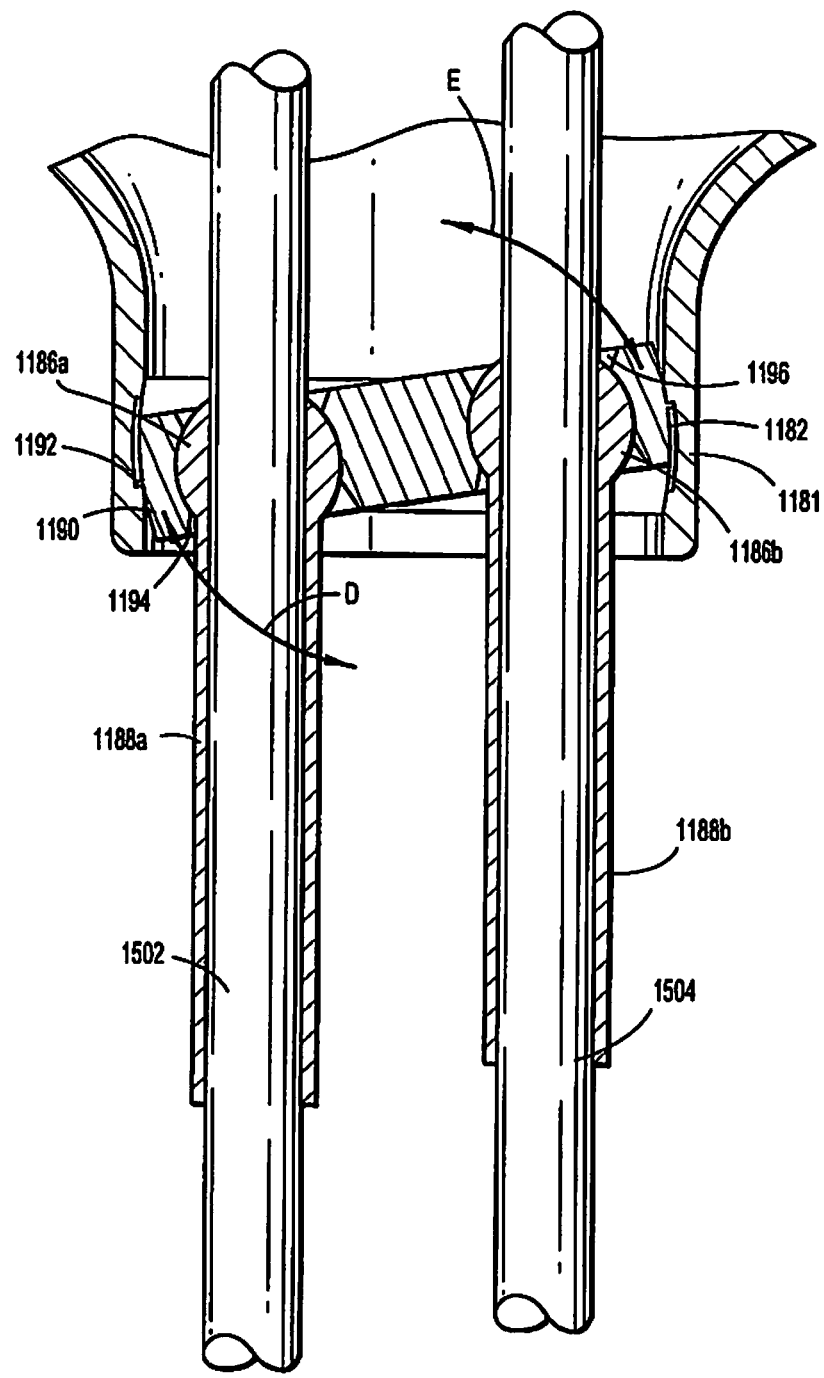
FIG. 70A is a cross-sectional view similar to FIG. 70 showing pivoting of the cannula support plate.

Increased mobility of the cannula members, and thereby the surgical instruments inserted therethrough, is provided in the port assembly 1180 of FIGS. 70, 70A. In this embodiment, ball joints are provided as in the embodiment of FIG. 68, with the cannula members 1188a, 1188b, extending distally from ball portions 1186a, 1186b. However, in this version, the transverse support 1190 supporting the cannulas 1186a, 1186b is in the form of a movable rigid plate 1190. Plate 1190, which has recesses 1194, 1196 to receive ball portions 1186a, 1186b, is positioned within body portion 1181 and has a circumferential ridge or lip 1192 extending from an outer surface. The ridge 1192 travels within groove 1182 formed in an inner wall of the body portion 1181. As a result, the plate 1194 can rotate 360 degrees to change the position of the cannulas 1188a, 1188b as well as float or pivot within body portion 1181 as depicted by the arrows D and E of FIG. 70A. Thus, the instrument can be manipulated within the respective cannulas with an increased freedom of movement.

It should be appreciated, that although not shown, seals can be provided in the cannula members of FIGS. 68-70 to prevent passage of insufflation gas. The seal can be similar for example to those described with respect to the embodiment of FIG. 60. The plates of the embodiments of FIGS. 68-71 are preferably composed at least in part of metal.

Figure 71:
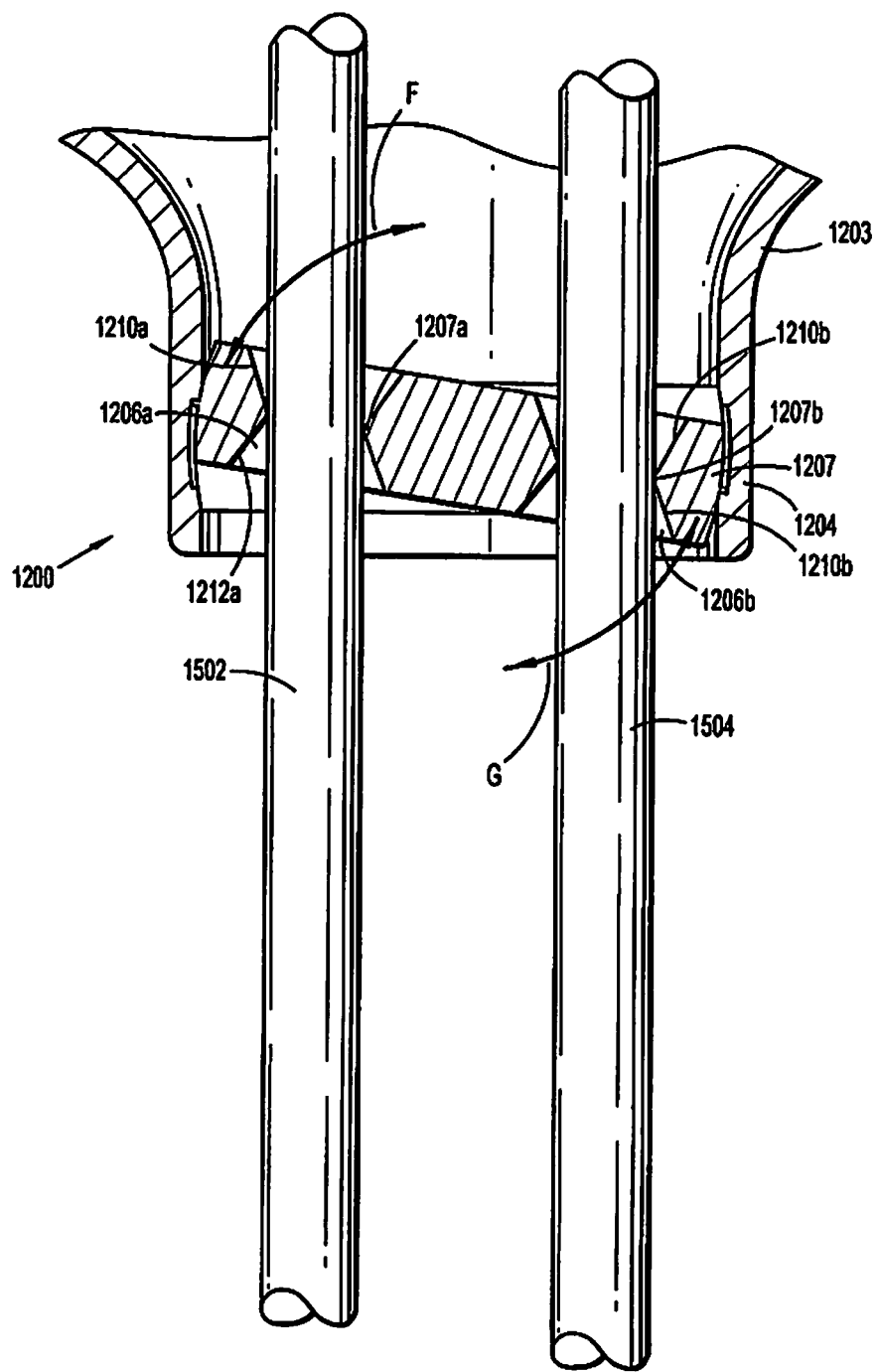
FIG. 71 is a cross-sectional view of another alternate embodiment of the port assembly of the present invention and showing two instruments inserted through the plate.

In the embodiment of FIG. 71, the port assembly 1200 has a floating plate 1202 extending substantially transversely within body portion 1204. The plate has recesses 1206a, 1206b with inwardly directed walls 1207a, 1207b to frictionally engage the surgical instruments inserted therethrough. Recess 1206a has upper and lower chamfered surfaces 1210a, 1212a to enable the instrument 1502 to pivot therein as shown by the arrow F. Similarly, recess 1206b has upper and lower chamfered surfaces 1210b, 1212b to enable the instrument 1504 to pivot therein as shown by the arrow G. More than two recesses can be provided to receive two or more cannulas. Additionally, gaseous seals can be provided in the recesses to prevent the escape of gas through the port assembly for certain surgical procedures. Body portion 1204 has a flared proximal portion 1203 as in the embodiments of FIGS. 68-70.

Another alternate embodiment is illustrated in FIGS. 72 and 72A-72C. In this embodiment, port assembly 1300 has a support ring 1302 and a lower plate 1304 and an upper plate 1310 supported within ring 1302 with cannulas 1330a, 1330b and 1330c attached thereto. Lower plate 1304 has two kidney-like shaped openings 1306a and 1306b and a circular opening 1307. Similarly, upper plate 1310 has two kidney-like shaped openings 1316a, 1316b and a circular opening 1317. The plates 1304, 1310 are mounted in a substantially transverse orientation within ring 1302 which is mounted within body portion 1320.

Body portion 1320 is similar to the body portion of the port of FIG. 60, having for example a flared proximal portion 1322, suture anchors 1325, obturator receiving recesses 1326 and a substantially cylindrical body 1324 with annular ridges 1328 on an outer surface of portion 1320. The openings in the plates have upper and lower chamfered surfaces, forming an inwardly extending wall (see e.g. walls 1317a and 1319a of respective openings 1317 and 1316a of upper plate 1310 and walls 1309b and 1307a of respective openings 1306b, 1307 of lower plate 1304) for frictional engagement of the cannula members 1330a, 1330b and 1330c while enabling pivoting movement of the cannula members as shown by arrow H in FIG. 72C. Cannula 1330b is shown with an insufflation port 1340 similar to that of the embodiment of FIG. 60. To prevent the egress of insufflation gas, the cannula members can include seals such as those described herein. Cannula 1330b is shown having a larger diameter than the other cannulas, although as in the other embodiments described herein, various differing diameter cannulas or same diameter cannulas can be provided.

Figure 72:
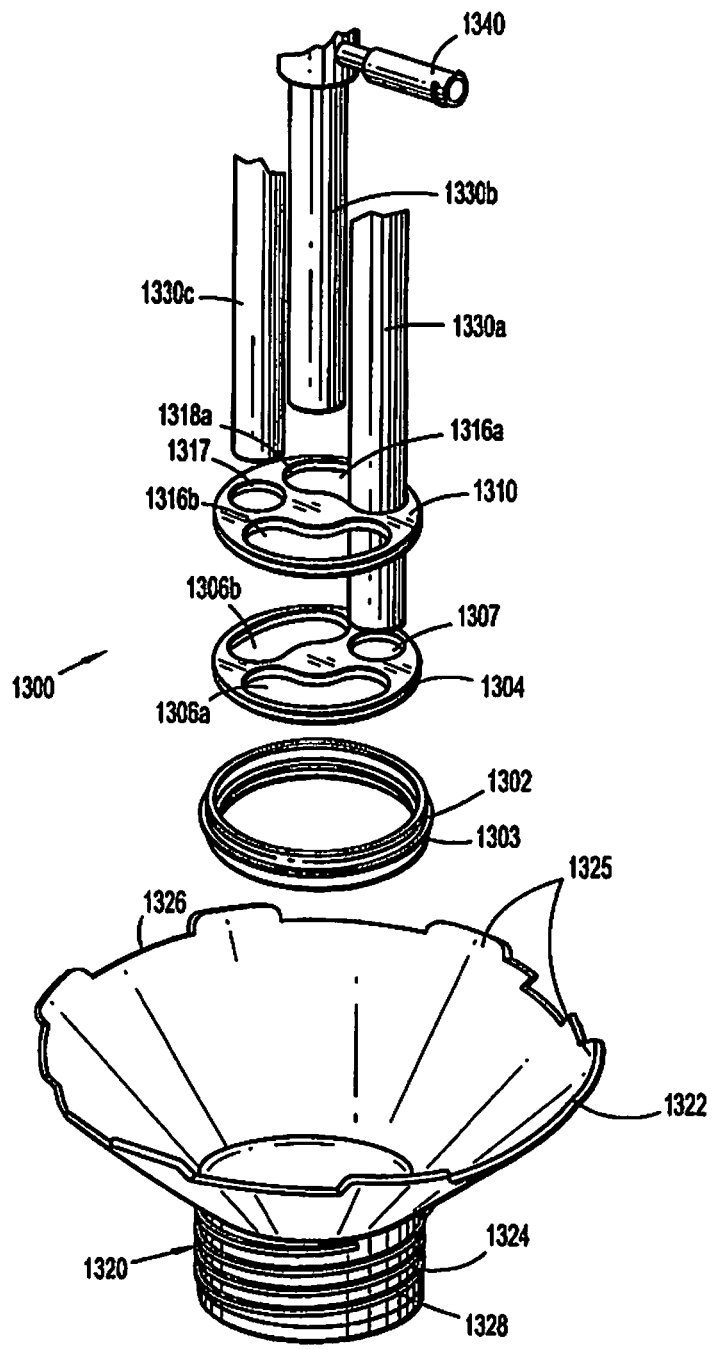
FIG. 72 is an exploded perspective of an alternate embodiment of the port assembly of the present invention having a pair of rotatable and pivotable plates.
Figure 72A:
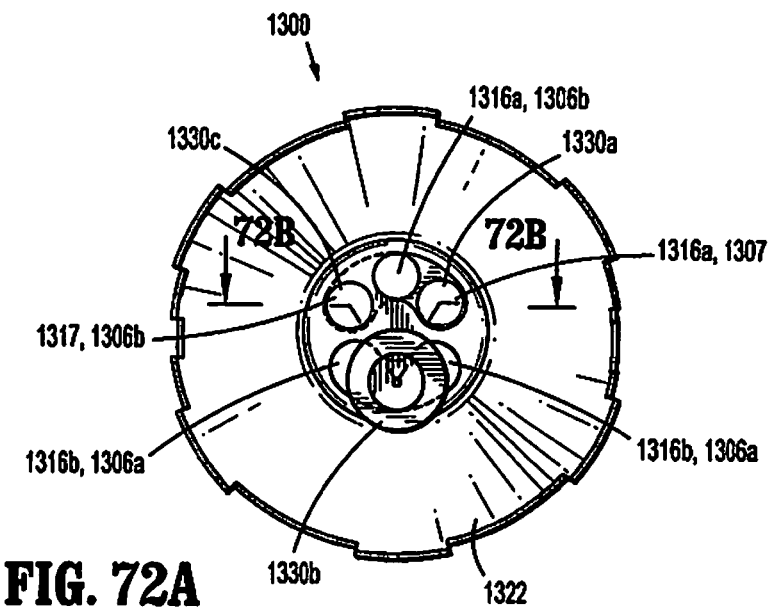
FIG. 72A is a top plan view of the port assembly of FIG. 72.
Figure 72B:
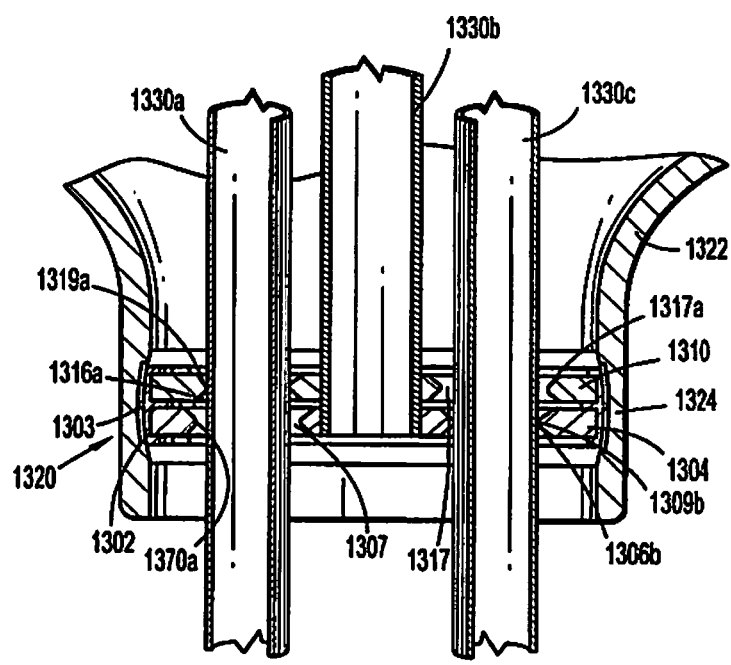
FIG. 72B is a cross-sectional view of the port assembly of FIG. 72 taken along line 72B-72B of FIG. 72A.
Figure 72C:
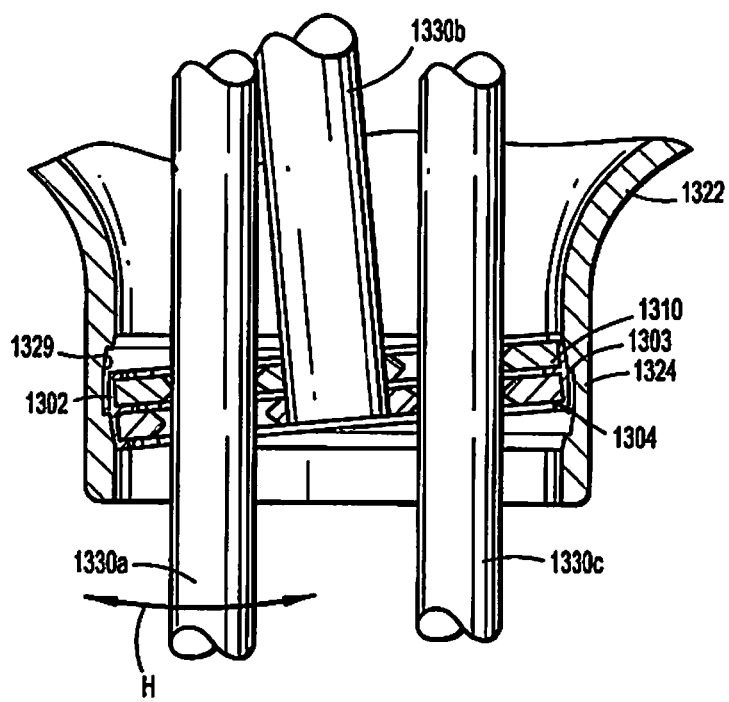
FIG. 72C is a cross-sectional view similar to FIG. 72B showing pivotal movement of the plates.

Ring 1302 has a circumferential flange or lip 1303 which moves within recess 1329 formed in an inner wall of body 1324 as shown in FIG. 72B. This enables both pivotable movement (see FIG. 72C) and rotational movement of the ring 1302 and attached plates 1304, 1310 to change the orientation of the cannula members 1330a, 1330b and 1330c fixedly attached to the plates by movement of the instruments extending therethrough. Moreover, each of the plates 1304, 1310, is rotatable independent of the other plate about an axis substantially parallel to the longitudinal axis of the body portion 1320 to change the position of the cannula members 1330a-1330c with respect to outer circumferential portion of the body portion 1324. Such rotation of the plates is limited by the outer edges of the kidney-like shaped openings 1316a, 1316b and 1306a, 1306b. For example, if plate 1310 is rotated clockwise, edge 1318a of opening 1316a would abut cannula 1330a, thereby limiting the rotational movement. In the illustrated embodiment, about 30 degrees of rotation of the plates can be achieved. However, different shaped openings enabling different degrees of rotation are also contemplated.

Figure 73:
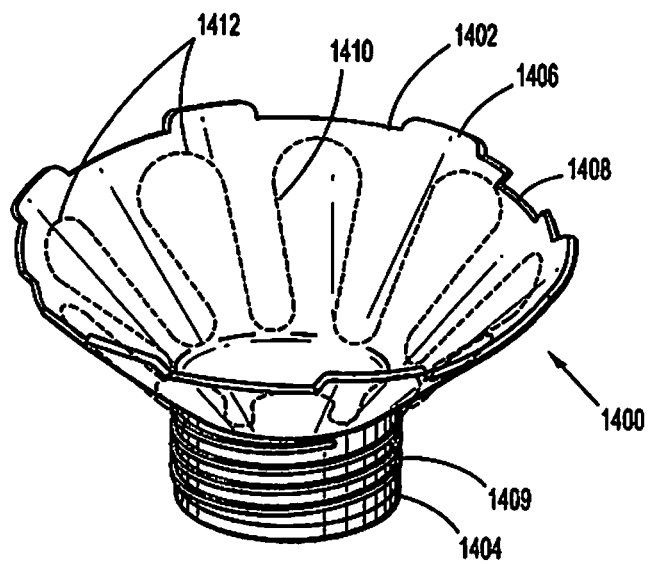
FIG. 73 is a perspective view of another alternate embodiment of the port assembly.
Figure 73A:
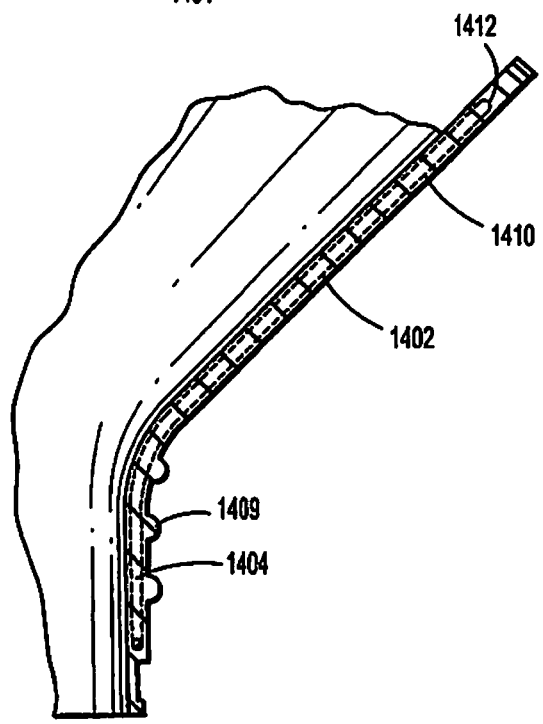
FIG. 73A is a partial cross-sectional view of the port assembly of FIG. 73.

FIGS. 73 and 73A illustrate an alternate port assembly. Port assembly is substantially the same as the port assembly of FIG. 60 except for the material and the provision of a wire which provides for an expandable port. More specifically, port assembly 1400 has a flared proximal portion 1402 forming a substantially conical or funnel shape with suture anchors 1406, obturator receiving recesses 1408 and a substantially cylindrical distal portion 1404. As in the embodiment of FIG. 60, suture anchors 1406 and obturator supporting recesses 1408 are provided in proximal portion 1402. Tissue engaging ribs 1409 can be provided on an outer surface of portion 1404. Port assembly 1400 differs from port assembly 1010 of FIG. 60 in that the proximal portion is formed of more flexible material such as thermoplastic elastomers. This enables the portion 1402 (or a portion thereof) to be placed in an opening in a collapsed (reduced profile) configuration. By providing a port which is foldable or deformable by an external force into a configuration with a smaller outer diameter (e.g. a cylinder), insertion into a body opening could be aided in certain applications and smaller packaging can be achieved as the port can be packaged, for example, in a cylindrical sleeve.

Additionally, the more flexible material allows the proximal portion 1402 to be stretched which could increase the range of motion of the surgical instruments inserted through the cannula members (not shown) extending from the port 1400 as the instruments can be bent at an angle exceeding the transverse dimension of the flared portion in the expanded, but not stretched, position. That is, the port will be "giving" by deformation of its walls by the pressure applied by the instruments during the surgical procedure. A flexible membrane and cannula members and extensions with seals such as those described with respect to the port assembly of FIG. 60 are preferably part of the port assembly 1400 but for brevity the description is not repeated herein (and the components are not shown in the drawings).

Embedded in the wall of the proximal portion 1402 is an expandable wire 1410. Multiple wires could also be utilized. The wire 1410 in some embodiments is made of a metal with sufficient springiness to automatically move to an expanded configuration when not stressed. It could alternatively be made of a shape memory material such as Nitinol with an expanded memorized position. In use, the wire would provide a mechanism for expanding the proximal portion 1402 and a support for increasing the rigidity of the portion 1402. The wire 1410 as shown has a series of loops 1412. Although shown embedded in the wall, alternatively the wire can be covered fully or in part by the material on one or both sides. It is contemplated that the wire in its entirety, or in parts thereof, could be deformable and expandable, symmetrically or asymmetrically (non-uniformly). In other words, the dimensions and shapes of the cross-sections at different portions (or levels—e.g. proximal, distal, most proximal, etc.) of the port can be substantially different and dynamic during the operation to facilitate movements of the instruments within the port.

It is also contemplated that instead of the wire(s) providing the expansion of the proximal portion 1402, the wires can be provided just to add some rigidity to the material of the proximal portion 1402 to provide some support. In such embodiments, the material of the proximal portion can be flexible and stretchable or alternatively it can itself be expandable either by self expansion or expansion by another instrument such as a mechanical expander. The expander could also be used to expand the embedded wire.

The surgical port assemblies described herein may be provided with a built-in or integrated endoscope which can incorporate digital chip technology. The built-in camera is maneuverable via cables (not shown) in the shaft, which could be bendable. Alternatively, orientation control may be effectuated wirelessly with a wireless receiver integrated into the port body member or the distal end portion of the scope arm or shaft. Flexible endoscopes could also be utilized, as well as other ways to visualize the remote surgical site.

When flexible endoscopes are utilized (endoscopes entirely flexible or endoscopes with flexible sections) it may be useful to provide a way to angle the cannula to maintain the scope in an angled position directed to the surgical site. If the cannula through which the flexible scope is inserted is flexible, the scope may not have sufficient rigidity to angle the cannulas. In this case, a tube can be inserted into the cannula to increase the rigidity of the cannula and then manipulated to direct the cannula to a desired angle so that the scope inserted through the tube and cannula is at a desired angle. The tube can then be secured to the port, e.g. by a hook or wire, to maintain the cannula and scope in position. With rigid cannulas, it may also be desirable to provide a hook, wire or other structure to maintain the cannula in position to free the user's hands.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A surgical port for positioning within an opening in a patient formed via a surgical incision comprising:
   a body defining a proximal end and a distal end and composed at least in part of a first material, the body including:
      a proximal portion defining a funnel shape flaring outwardly towards the proximal end of the body and flaring inwardly towards the distal end of the body transitioning directly into
      a distal portion defining a cylindrical shape, a maximum diameter of the proximal end being greater than a maximum diameter of the distal end; and
      a wire embedded in the funnel shape of the proximal portion, at least portions of the wire positioned in the vicinity of the distal portion,
   the wire extending in a multiple looped configuration of non-intersecting curved portions positioned in the vicinity of the proximal portion.

2. The port of claim 1, wherein the wire is embedded within the proximal portion or embedded within the proximal portion and the distal portion.

3. The port of claim 1, wherein the proximal portion defines an inner wall surface and an outer wall surface, and wherein at least a portion of the wire is covered by the first material on the inner wall surface or on the outer wall surface or on both the inner wall surface and on the outer wall surface.

4. The port of claim 1, wherein the wire is automatically expandable.

5. The port of claim 1, wherein the wire is expandable by engagement by an expandable member.

6. The port of claim 1, wherein the wire is flexible and symmetrically expandable.

7. The port of claim 1, wherein the wire is flexible and asymmetrically expandable.

8. The port of claim 1, further comprising a membrane composed at least in part of a second different material and supported by the distal portion of the body and disposed at the distal end thereof, at least a portion of the membrane being flexible.

9. The port of claim 8, further comprising first and second cannulas extending distally from the membrane and being movable with respect to the body via movement of an instrument inserted therethrough,
the surgical port configured such that the first and second cannulas extend distally from the membrane a distance sufficient such that, when operably disposed within tissue, the membrane and the first and second cannulas are disposed beneath the surgical incision in the opening in the patient.

10. The port of claim 1, wherein the cylindrically shaped distal portion defines an outer surface that includes a tissue engaging portion having an irregular shape, and
wherein the tissue engaging portion is configured to engage tissue adjacent to the opening in the patient via the irregular shape.

11. The port of claim 1, wherein the proximal portion is formed from a material which has a greater flexibility than a material from which the distal portion is formed.

12. The port of claim 11, wherein the proximal portion defines a perimeter at a proximal end of the proximal portion, the perimeter defining a transverse dimension when the proximal portion is in a non-deformed condition, and
wherein the proximal portion is deformable such that the perimeter is expandable to a dimension that is greater than the transverse dimension when the proximal portion is in the non-deformed condition.

13. The port of claim 1, wherein the funnel shape is configured such that first and second cannulas can extend distally from the distal portion and such that a first instrument can be inserted through the first cannula and a second instrument can be inserted concurrently through the second cannula.

14. A surgical port comprising:
a body having a wall, the body including:
a proximal portion defining a funnel shape flaring outwardly towards a proximal end of the body and flaring inwardly towards a distal end of the body transitioning directly into
a distal portion defining a cylindrical shape, a maximum diameter of the proximal end being greater than a maximum diameter of the distal end, first and second cannulas extending from the body and being movable with respect to the body via movement of an instrument inserted therethrough, wherein at least portions of the body wall are deformable by pressure exerted by the instrument thereon; and
a support embedded in the funnel shape of the proximal portion wherein the support comprises a wire that extends in a multiple looped configuration of non-intersecting curved portions positioned in the vicinity of the proximal portion and opposing non-intersecting curved portions positioned in the vicinity of the distal portion, the support engageable with the body to increase the rigidity of at least portions of the body.

15. The port of claim 14, wherein the wire is asymmetrically expandable.

16. The port of claim 14, wherein the proximal portion is formed from a first material, the body further comprising a membrane composed at least in part of a second different material and supported by the distal portion of the body and disposed at the distal end thereof, at least a portion of the membrane being flexible.

17. The port of claim 14, wherein the cylindrically shaped distal portion defines an outer surface that includes a tissue engaging portion having an irregular shape, and
wherein the tissue engaging portion is configured to engage tissue adjacent to an opening in a patient via the irregular shape.

18. The port of claim 14, wherein the proximal portion is deformable into a collapsed configuration by an external force such that at least a portion of the proximal portion is insertable into a body opening.

* * * * *